US012667650B2

(12) United States Patent
Shfaram et al.

(10) Patent No.: US 12,667,650 B2
(45) Date of Patent: Jun. 30, 2026

(54) BREAST MILK EXTRACTION KIT COMPRISING A BREAST MILK PUMP AND A PUMPING DEVICE

(71) Applicant: Annabella Tech Ltd., Kfar Saba (IL)

(72) Inventors: Adi Shfaram, Herzliya (IL); Andres Wainstein, Ramat Gan (IL); Gustavo Turkieltaub, Tel Aviv (IL); Oded Halawani, Ra'anana (IL)

(73) Assignee: Annabella Tech Ltd., Kfar Saba (IL)

( * ) Notice: Subject to any disclaimer, the term of this patent is extended or adjusted under 35 U.S.C. 154(b) by 118 days.

(21) Appl. No.: 18/019,056

(22) PCT Filed: Aug. 11, 2021

(86) PCT No.: PCT/IL2021/050985
§ 371 (c)(1),
(2) Date: Jan. 31, 2023

(87) PCT Pub. No.: WO2022/034594
PCT Pub. Date: Feb. 17, 2022

(65) Prior Publication Data
US 2023/0293785 A1 Sep. 21, 2023

Related U.S. Application Data

(63) Continuation of application No. 16/990,111, filed on Aug. 11, 2020, now abandoned.
(Continued)

(51) Int. Cl.
*A61M 1/00* (2006.01)
*A61M 1/06* (2006.01)

(52) U.S. Cl.
CPC .............. *A61M 1/064* (2014.02); *A61M 1/67* (2021.05); *A61M 2210/1007* (2013.01)

(58) Field of Classification Search
CPC ........ A61M 1/06; A61M 1/062; A61M 1/064; A61M 1/066; A61M 1/067; A61M 1/068;
(Continued)

(56) References Cited

U.S. PATENT DOCUMENTS 6,004,288 A 12/1999 Hochstedler et al.
6,579,258 B1 6/2003 Atkin et al.
(Continued)

FOREIGN PATENT DOCUMENTS

CN 107007893 A 8/2017
EP 2111882 A1 10/2009
(Continued)

OTHER PUBLICATIONS

International Search Report and Written Opinion dated Dec. 15, 2021 for PCT/IL2021/050985.

*Primary Examiner* — Kevin C Sirmons
*Assistant Examiner* — William R Frehe
(74) *Attorney, Agent, or Firm* — Ballard Spahr LLP

(57) ABSTRACT

A pumping device configured to be used in conjunction with a breast milk pump, said breast milk pump including at least one electrically operable component and a vacuum assembly, the pumping device being connectable to the breast milk pump via a cable including a cable first end connectable to the breast milk pump, an opposite cable second end connectable to the pumping device, and an electrical wiring and an air flow conduit extending between the cable first end and the cable second end.

9 Claims, 33 Drawing Sheets

Related U.S. Application Data

(60) Provisional application No. 63/212,768, filed on Jun. 21, 2021, provisional application No. 63/123,599, filed on Dec. 10, 2020.

(58) Field of Classification Search
CPC ................ A61M 1/069; A61M 1/0693; A61M 1/06935; A61M 1/0697; A61M 1/007; A61M 2210/1007; A61B 2018/00333; A61J 13/00
USPC .......................................... 439/668–669, 192
See application file for complete search history.

(56) References Cited

U.S. PATENT DOCUMENTS

| | | | | |
|---|---|---|---|---|
| 2003/0073951 | A1* | 4/2003 | Morton | .............. A61B 10/0041 604/73 |
| 2004/0087898 | A1 | 5/2004 | Weniger | |
| 2005/0154348 | A1 | 7/2005 | Lantz et al. | |
| 2007/0078383 | A1 | 4/2007 | Tashiro et al. | |
| 2010/0130921 | A1 | 5/2010 | Kobayashi et al. | |
| 2014/0330200 | A1 | 11/2014 | Scheidegger et al. | |
| 2015/0065994 | A1 | 3/2015 | Fridman et al. | |
| 2016/0058928 | A1 | 3/2016 | Nowroozi et al. | |
| 2018/0078687 | A1 | 3/2018 | Alvarez et al. | |
| 2018/0147331 | A1 | 5/2018 | Liu | |
| 2019/0336661 | A1 | 11/2019 | Berkhof et al. | |
| 2019/0365971 | A1* | 12/2019 | Miller | .................. A61M 1/064 |
| 2020/0016307 | A1 | 1/2020 | Edelman et al. | |
| 2021/0268159 | A1 | 9/2021 | Schwarz et al. | |
| 2021/0361837 | A1 | 11/2021 | Bijoor | |

FOREIGN PATENT DOCUMENTS

| | | |
|---|---|---|
| JP | 2012522614 A | 9/2012 |
| WO | 2018229782 A1 | 12/2018 |

\* cited by examiner

305

307

306B

306A

301

BREAST MILK EXTRACTION KIT COMPRISING A BREAST MILK PUMP AND A PUMPING DEVICE

TECHNOLOGICAL FIELD

The presently disclosed subject matter relates to a breast milk extraction kit comprising a breast milk pump and a pumping device.

BACKGROUND

Breastfeeding is the best source of nutrition for a baby and provides health benefits to the nursing mother. Sometimes a nursing mother needs to use a breast pump to collect milk. A variety of breast pumps are available, such as hand-operated pumps and electric pumps. The electric pumps may be battery and/or AC powered. Even though there are many breast pumps available, the need still exists for an improved user-friendly breast pump.

GENERAL DESCRIPTION

Generally, the presently disclosed subject matter is related to a breast milk extraction kit including a breast milk pump, a pumping device and a cable configured to establish a connection therebetween. The aspects detailed below are related to various manners of operations of the kit and the breast milk pump. The breast milk pump is configured to be engaged with a breast and operated in order to extract milk therefrom. The below description of the aspects includes reference to the directions, which have been, for the purposes of this description, defined with respect to the body of a user when the user is standing in an upright position and is using the breast milk pump oriented in its upright orientation in which the milk collection container is positioned upright as well, and are intended to be understood accordingly. For instance, a direction along a height of the user is intended to be understood as a direction along the height of the user when the user is standing upright. Any reference to upper, lower, and sideways directions are intended to be understood with respect to the height of the user standing upright.

The various aspects described herein below are to be understood as implementable in any combinations, i.e., any or all of the features of one aspect can be used with any one of the other aspects.

According to a first aspect of the presently disclosed subject matter there is provided a breast milk pump comprising:

a milk extraction assembly comprising a funnel configured to engage a breast of a user, said funnel comprising a flexible portion having a flexible portion inner surface for facing the breast and an opposite flexible portion outer surface;

a stimulating mechanism facing the flexible portion outer surface and configured to manipulate the flexible portion; and a position adjustment mechanism configured to adjust a position of the stimulating mechanism with respect to the funnel, said position adjustment mechanism comprising at least one lever member articulated to the stimulating mechanism, the lever member being pivotable about a lever pivot axis, to move the stimulating mechanism.

The position of the stimulating mechanism can at least partially define a size of an opening of the funnel configured to receive the breast, thus, by adjusting the position of the stimulating mechanism, a dimension of the opening of the funnel is controlled, thereby controlling a fit of the breast milk pump onto the breast during use of the breast milk pump. For instance, for different sizes and shapes of breasts, the position of the stimulating mechanism can be adjusted to adjust the size of the opening to fit the breast accordingly. Further, the fit of the breast milk pump onto the breast can be adjusted to adapt for a sensitivity of the breast to any kind of stimulation that may vary from user to user. For instance, a user with a very sensitive breast would prefer comparatively lesser extent of stimulation and a user with lesser sensitive breasts would prefer a higher extent of stimulation for the milk to be extracted therefrom. The position of the stimulating mechanism also effects the extent of stimulation that would be experienced by the breast when the stimulating mechanism is operated. Furthermore, a user might want to adjust the fit of the funnel onto the breast based on a physical condition of the breast such as pain, swelling, soreness, etc.

The stimulating mechanism can have any structure described herein with respect to some of the aspects or can be a structure known in the art as being configured to manipulate the flexible portion of the funnel to serve a general purpose of imitating tongue movements of a baby so as to stimulate the breast for extraction of milk therefrom.

The position adjustment mechanism can be configured to move the stimulating mechanism between an initial position at which the stimulating mechanism causes the flexible portion to have a first shape at least prior to operation of the stimulating mechanism, and a final position at which the stimulating mechanism causes the flexible portion to have a second shape different from the first shape at least prior to operation of the stimulating mechanism. In some examples, at the initial position, the stimulating mechanism causes a first tension in the flexible portion and at the final position, the stimulating mechanism causes a second tension, greater than the first tension, in the flexible portion. The first tension can be zero at least when the stimulating mechanism is not being operated. The initial position can be a lowermost position of the stimulating mechanism when the breast milk pump is held upright with a milk collection container being in an upright position as well, and the final position can be an uppermost position of the stimulating mechanism.

The position adjustment mechanism can be configured to move the stimulating mechanism from the initial position to the final position thereof at least partially in a direction extending along a height of the user.

In some examples, the position adjustment mechanism can be configured to move the stimulating mechanism in an arcuate path.

In some examples, the position adjustment mechanism can be configured to move the stimulating mechanism majorly in a vertical path taken with respect to the breast milk pump being held upright with a milk collection container being in an upright position as well. The vertical movement of the stimulating mechanism results in more effective and quick adjustment of the grip of the breast milk pump with respect to the breast.

The lever member can comprise a lever first portion articulated to the stimulating mechanism and a lever second portion, the lever member being configured to be pivoted in response to actuation of the lever second portion. In some examples, the lever second portion can be actuated by the user directly holding the lever second portion.

The position adjustment mechanism can comprise an actuator articulated to the lever second portion, the lever member being pivotable by the actuator.

The breast milk pump can comprise a proximal portion configured to be positioned towards the breast, a distal portion configured to be positioned away from the breast, and a main axis extending therebetween, wherein the actuator is positioned distant from the stimulating mechanism at least in a direction along the main axis. The actuator being distant from the stimulating mechanism, which most generally would be under the breast, renders the use of the actuator easier and more effective. Thus, the actuator can be positioned at a location on the breast milk pump which is most convenient for the user to use while using the breast milk pump and is also visible to the user as to provide visual indications to the user indicating a state of the actuator and hence the position of the stimulating mechanism. For instance, the user can hold the breast milk pump by a first hand and using the second hand for conveniently using the actuator without intervening the area of the funnel. In some examples, the position adjustment mechanism can comprise two lever members, one on each side of the breast milk pump, and a respective actuator for each of the two lever members. The user can use any one of the actuators as per the convenience. The two lever members can be connected to each other such that actuating one of them causes the other one to follow the same path. The actuator is configured to move the lever second portion. The movement of the second lever portion can cause the lever first portion to pivot about the lever pivot axis.

In some examples, the lever member can comprise a lever first arm extending between the lever first portion and the lever pivot axis, and a lever second arm extending between the lever pivot axis and the lever second portion, and the lever first arm can be longer than the lever second arm. The relative length of the lever arms effects the extent of movement of the lever first portion relative to the movement of the lever second portion. The lever first arm being longer than the lever second arm causes the lever first portion to move comparatively more than the lever second portion is moved by the actuator. This results in requiring the user to do a lesser effort in adjusting the position of the stimulating mechanism.

The position adjustment mechanism can be configured for a coarse adjustment of the position of the stimulating mechanism and for a fine adjustment of the position of the stimulating mechanism. The position adjustment mechanism can allow a user for a big movement of the stimulating mechanism by a particular extent of actuation of the actuator at the beginning of the adjustment and a relatively smaller movement of the stimulating mechanism by the same extent of actuation of the actuator as the adjustment proceeds. This allows the user to more accurately adjust the position of the stimulating mechanism. For instance, when the stimulating mechanism is far off from the desired position, a coarse adjustment can be done, and as the stimulating mechanism approaches the desired position and approaches the breast, a fine adjustment would be preferable by the user.

The actuator can comprise a rotatable wheel. The position adjustment mechanism is configured to convert said rotation of the wheel into said movement of the stimulating mechanism articulated to the lever first portion. In other examples, the actuator can comprise a linearly moveable element configured to move the lever second portion.

The actuator and the lever second portion can constitute at least a part of a cam follower arrangement. The actuator can comprise a cam and the second lever portion being articulated to the cam via a follower. The follower can be a separate member or can be a part of the lever second portion. The cam can comprise a spiral path extending between a radially outermost end and a radially innermost end thereof. The follower can be biased to retain the spiral path when the cam is rotated, thereby following the variation in radius of the spiral path. When the follower is at one of the radially innermost end and the radially outermost end, the stimulating mechanism is at the initial position, and when the follower is at other one of the radially innermost end and the radially outermost end, the stimulating mechanism is at the final position.

The spiral path can comprise an initial portion including the radially innermost end and a terminating portion including the radially outermost end, wherein a curvature of the path is greater at one of the initial and the terminating portion than a curvature of the path at other one of the initial and the terminating portion. When the follower is at one of the initial and the final portions, the position adjustment mechanism can be configured for a coarse adjustment of the position of the stimulating mechanism, and when the follower is at other one of the initial and the final portions the position adjustment mechanism can be configured for a fine adjustment of the position of the stimulating mechanism. In some examples, when the follower is at the initial portion, the position adjustment mechanism can be configured for a coarse adjustment of the position of the stimulating mechanism, and when the follower is at the final portion, the position adjustment mechanism can be configured for a fine adjustment of the position of the stimulating mechanism.

The cam can be configured to lock the follower at one or more locations between the radially outermost end and the radially innermost end. The cam can be configured to prevent a movement of the follower by the lever member. The slope of the spiral path is so configured that the follower can be moved only by the rotation of the cam. When the cam is not rotated, the follower retains its location and does not move by a force exerted by the stimulating mechanism via the lever member. The cam arrangement can comprise any other follower locking means to lock the follower at any location along the spiral path.

The breast milk pump can further comprise a body and a stabilizing mechanism configured for controlling stabilizing of the lever member with respect to the body. The stabilizing mechanism can comprise a stabilizing biasing member configured for controlling an extent of the stabilizing of the lever member with respect to the body. The stabilizing biasing member can be a spring. The tension of the spring effects the extent of stabilizing of the lever member, i.e., more tense the spring would be, the more stabilized the lever member would be to the body. The stabilizing mechanism comprises a controlling member configured for changing a tension of the stabilizing biasing member. The controlling member can comprise a stabilizing cam configured to be rotated about an axle of the lever member to change the tension in the spring. The stabilizing cam can comprise a teeth member configured to lock the stabilizing cam in a plurality of positions, each position defining a corresponding tension in the spring. In order to increase or decrease the tension in the spring, the stabilizing cam can be rotated by the user, which in turn controls the extent of stabilizing of the lever member.

According to a second aspect of the presently disclosed subject matter there is provided a breast milk pump comprising:

a milk extraction assembly configured to engage a breast of a user, said milk extraction assembly comprising a pressure interface passage configured to allow passage of air therethrough; and a vacuum chamber comprising an orifice and configured to be detachably attachable to the breast milk pump for establishing a fluid communication between the orifice and the pressure interface passage.

The vacuum chamber being detachable from the breast milk pump enhances the modularity of the breast milk pump, and enables a user to wash the vacuum chamber. Although, generally, at some point a milk flow path is separated from an air flow path in a breast milk pump so as not to allow the milk to enter a vacuum chamber, yet some milk particles, especially in the form of fumes or vapors or the small particles mixed with the air, enter the vacuum chamber and get accumulated therewithin over time. Thus, the vacuum chamber needs to be washed. However, if the vacuum chamber is not detachable, especially in the breast milk pumps comprising electrically operable components (e.g. motor, sensors, display units, controllers, connectors, etc.), washing the same is difficult. Thus, the vacuum chamber being detachable allows a user to wash the vacuum chamber without risking the electrically operable components.

The vacuum chamber can be configured to generate a negative pressure within the milk extraction assembly through the orifice and the pressure interface passage. The pressure interface passage constitutes at least a part of the air flow path extending between the vacuum chamber (when the vacuum chamber is connected to the breast milk pump) and the milk extraction assembly. The air flow path and the milk flow path can have a common portion at least in the beginning, and can be separated from each other thereafter. The breast milk pump can further comprise a sealing member configured to seal the fluid communication between the pressure interface passage and the orifice. The sealing member can be configured to prevent leakage of air at the connection of the orifice and the pressure interface passage.

The breast milk pump can further comprise a body and said milk extraction assembly can be detachably connectable to the body. The body can comprise a chamber supporting wall configured to support the vacuum chamber at least when the vacuum chamber is attached to the breast milk pump. The vacuum chamber can be connectable to the chamber supporting wall. The orifice and the pressure interface passage are configured to be in fluid communication through a chamber supporting wall opening formed in the chamber supporting wall.

The chamber supporting wall can comprise at least one guiding element configured to guide the vacuum chamber into its designated position during attachment thereof to the breast milk pump. The vacuum chamber can comprise a guidable element configured to be guided by the guiding element during attachment of the vacuum chamber to the breast milk pump. The guiding element can be a depression formed in the chamber supporting wall and the guidable element can be a projection formed in the vacuum chamber configured to be received within the depression. In some examples, the guiding element can be a projection formed in the chamber supporting wall and the guidable element can be a depression formed in the vacuum chamber configured to receive therewithin the projection. The orifice and the pressure interface passage can be configured to be in communication through the guiding element.

The chamber supporting wall can further comprise at least one chamber locking means configured to detachably lock the vacuum chamber when connected to the breast milk pump thereby connecting the vacuum chamber with the body. The vacuum chamber can be configured to be connected to the breast milk pump and to be locked at the chamber locking means simultaneously by a single action.

The milk extraction assembly can be connectable to and/or detachable from the body irrespective of whether the vacuum chamber is connected to or detached from the body. The vacuum chamber can be connectable to and/or detachable from the body irrespective of whether the milk extraction assembly is connected to or detached from the body. The milk extraction assembly can be configured to be at least partially received within the body and can be configured to be extracted in a first extraction direction. The vacuum chamber can be configured to be received at least partially within the body and can be configured to be extracted in a second extraction direction. The vacuum chamber and the milk extraction assembly can be configured to be attached to each other at a particular angle based on an angle between the first extraction direction and the second extraction direction, such that the milk extraction assembly and the vacuum chamber can be detached from the body independently of each other.

The breast milk pump can further comprise a vacuum assembly comprising the vacuum chamber, a membrane configured to be removably articulated to the vacuum chamber, and a cap configured to close the vacuum chamber at least with the membrane articulated thereto. The membrane can be a diaphragm configured to deform when a pressure difference is created on two sides of the diaphragm. The vacuum chamber can comprise a chamber rim and the membrane can comprise a membrane rim corresponding to the chamber rim and configured to be positioned on the chamber rim. The cap can comprise a lip, the cap being configured to sealingly close the vacuum chamber while sealing the membrane rim between the lip and the chamber rim. The connection of the chamber rim, the membrane rim, and the lip can be leakage proof, i.e., does not allow any leakage of air therefrom.

The cap can be configured to be removably locked to the chamber supporting wall. The cap can be configured to be removably locked to the chamber supporting wall via the at least one chamber locking means. In some examples, the vacuum assembly can be configured to be connected to the body while locking the vacuum chamber and the cap to the chamber locking means simultaneously in a single action. The vacuum chamber can comprise a chamber locking portion and the cap can comprise a cap locking portion, wherein the at least one locking means comprises a snap connector configured to receive the chamber locking portion and cap locking portion. The snap connector can comprise a first snapping portion configured to engage with and to lock the chamber locking portion, and a second snapping portion configured to engage with and to lock the cap locking portion. The cap can be configured to be detached from the chamber supporting wall together with the vacuum chamber. The cap can be configured to be connected to the chamber supporting wall independently of the vacuum chamber. When the cap is extracted from the body, the detachment of the cap from the chamber supporting wall causes detachment of the cap locking portion from the second snapping portion, which in turn displaces the snap connector and causes disengagement of the chamber locking portion from the first snapping portion.

The cap can further comprise a flange configured to engage with the membrane, wherein the cap is configured to tightly receive at least a portion of the membrane between the flange and the vacuum chamber when closed on the vacuum assembly. The frictional association between the flange, the membrane, and the vacuum chamber causes the vacuum chamber, the membrane, and the cap to be extracted from the body together in a single action. The vacuum assembly being extractable as a whole from the body by a single action results in easy and quick disassembly of the washable parts from the breast milk pump.

The vacuum chamber can have a chamber outer surface configured to face the breast milk pump and an opposite chamber inner surface, and the membrane can have a membrane first surface configured to face the chamber inner surface and an opposite membrane second surface configured to face the cap. The vacuum chamber can comprise a chamber first region defined by the chamber inner surface and the membrane first surface, and a chamber second region defined by the membrane second surface and the cap, the chamber first region configured to be in fluid communication with the milk extraction assembly through the orifice and the pressure interface passage when the vacuum chamber is connected to the breast milk pump. The chamber second region can be configured to be fluidly connected, via the cap, to a pumping device configured to generate a vacuum at the chamber second region. In response to the vacuum, the membrane can be configured to be deformed towards the chamber second region and generate a negative pressure in the chamber first region, and consequently in the milk extraction assembly via the orifice and the pressure interface passage.

According to a third aspect of the presently disclosed subject matter there is provided a body for a breast milk pump comprising a milk extraction assembly configured to be directly connected to a milk collection container to establish a milk flow path, the body comprising:

a component portion configured to accommodate one or more operational components to be used in conjunction with the breast milk pump;

an interface portion configured to be engaged with the milk extraction assembly while embracing the connection of the milk extraction assembly and the milk collection container.

The body can accommodate at least some of the components of the breast milk pump. The body being structured so as to accommodate the parts and components of the breast milk pump in a compact manner while separating the fluid containing parts from fluid free parts. Further, the body is structured so as to facilitate an electrical connection being away from a breast of the user and being connected to components configured to be located near the breast through within the body. The body, thus, providing more safety to the user while operating the breast milk pump having electrically operable components. Furthermore, the body being configured to enhance the modularity of the breast milk pump, i.e., enables the parts of the breast milk pump to be detachably attachable to assemble and disassemble the breast milk pump.

The component portion can be configured to at least partially engage the milk extraction assembly to allow the one or more operational components to be operated in conjunction with the milk extraction assembly. The operational components can be sensors, motor, vacuum assembly, display, controller, etc. The component portion can comprise a front component portion configured to at least partially engage the milk extraction assembly, and a rear component portion, the interface portion being positioned between the front component portion and the rear component portion. The front component portion can be configured to be positioned near the breast of the user while the rear component portion can be configured to be positioned away from the breast of the user.

The operational components can comprise at least one electrically operable component, the front component portion being configured to accommodate the electrically operable component, the rear component portion comprising an electrical connection port configured to facilitate a connection of the breast milk pump with an electrical power source, and the interface portion being configured to at least partially accommodate an electrical connection extending from the electrical connection port to the electrically operable component.

The milk extraction assembly can comprise a funnel and the operational components can comprise a stimulating mechanism configured to manipulate at least a flexible portion of the funnel, the front component portion being configured to accommodate the stimulating mechanism. The stimulating mechanism can be the electrically operable component.

The milk extraction assembly can comprise a cone member configured to engage the body and/or to be connected thereto. The funnel and the cone member can be integrally formed or can be separately manufactured and can be configured to be detachably attachable to each other. The funnel can be connected to the milk collection container as well as the vacuum assembly via the cone member. The cone member further comprises a one-way valve configured to be positioned in the milk flow path at a point downstream of a point of separation of the milk flow path and the air flow path. The one-way valve can be configured to prevent air and/or milk to flow from the milk collection container into the milk extraction assembly at least when a negative pressure is created in the milk extraction assembly. The cone member can comprise the point of separation of the milk flow path and the air flow path. The interface portion of the body can be configured to embrace at least a part of the cone member.

The operational components can further comprise a position adjustment mechanism configured to adjust a position of the stimulating mechanism with respect to the funnel, the front component portion being configured to accommodate at least a first adjustment component of the position adjustment mechanism, the rear component portion being configured to accommodate at least a second adjustment component of the position adjustment mechanism, and the interface portion being configured to at least partially accommodate a connecting component of the position adjustment mechanism connecting the first adjustment component and the second adjustment component. The connecting component can be a lever member, the first adjustment component can be a lever first portion, and the second adjustment component can comprise an actuator articulated to a lever second portion. The body can comprise an access opening configured to allow access therethrough to the actuator.

The breast milk pump can further comprise a vacuum assembly, the rear component portion being configured to accommodate the vacuum assembly and the interface portion being configured to at least partially accommodate an air flow path extending between the vacuum assembly and the milk extraction assembly.

The body can further comprise a chamber supporting wall separating the interface portion and the rear component portion, said chamber supporting wall comprising a chamber supporting wall opening being configured to establish a communication between the interface portion and the rear component portion. The air flow path can extend through the chamber supporting wall opening.

The rear component portion can comprise an air flow connection port configured to facilitate an air flow connection between the vacuum assembly and a pumping device. The pumping device can be configured to pump air in and out of the vacuum assembly. The electrical connection port and the air flow connection port can constitute a hybrid connection port.

The body can further comprise a separating layer configured to isolate the one or more operational components from the milk extraction assembly. The separating layer can be configured to isolate the front component portion from the milk extraction assembly. The separating layer can be flexible. The separating layer can be detachably attachable to the body.

The body can be configured to allow the milk extraction assembly to be detachably connected to the milk collection container through the interface portion. The body can be configured to be detachably connected to the breast milk pump via said connection of the milk extraction assembly and the milk collection container. The body can be configured to be received between at least a part of the milk extraction assembly and at least a part of the milk collection container thereby stabilizing the body together with the milk extraction assembly and the milk collection container when they are connected through the body.

The interface portion can comprise a through-passage configured to allow the milk extraction assembly to be connected to the milk collection container therethrough to establish the milk flow path. The through-passage can comprise a first through opening configured to receive therethrough the milk extraction assembly and a second through opening configured to receive therethrough the milk collection container. Thus, the milk extraction assembly and the milk collection container can be connected to each other within the through-passage. The first through opening has a rim configured to engage the milk extraction assembly and the second through opening has a rim configured to engage the milk collection container. The through-passage can be configured such that the rims of the first through opening the second through opening are configured to be received between the milk extraction assembly and the milk collection container thereby stabilizing the body together with the milk extraction assembly and the milk collection container when they are connected through the body. The body can be configured to constitute a housing for the breast milk pump. The body can constitute at least a part of the outermost surface of the breast milk pump.

According to a fourth aspect of the presently disclosed subject matter there is provided a funnel configured to be used with a breast milk pump, the funnel comprising:
 a rigid portion having an internal surface facing an interior of the funnel and an opposite external surface, the rigid portion having at least one opening formed therewithin; and
 a flexible layer over-molded over at least a portion of the internal surface of the rigid portion, the flexible layer comprising a manipulable portion extending at least partially over the at least one opening and configured to be manipulated by a stimulating mechanism. In some examples, the flexible layer can be over-molded over at least a majority of the internal surface of the rigid portion.

The flexible layer is configured to be manipulated by the stimulating mechanism and hence requires to be strongly connected to the rigid portion. The over-molding of the flexible layer imparts more strength to the connection of the flexible layer and the rigid portion than a connection on the edges only. The surface area of the connection of the flexible layer and the rigid portion increases substantially thereby providing enhanced strength to the funnel, especially to the flexible layer.

The manipulable portion can be configured to be manipulated via the at least one opening. The opening can be positioned in the rigid portion so as to be located towards a lower part of the breast of the user when the breast milk pump is in use. The manipulable can be configured to engage at least a part of the breast at least when manipulated. The part of the breast can be nipple or areola.

The flexible layer can further comprise a remaining flexible portion at least partially surrounding the manipulable portion. The manipulable portion can be more flexible than at least a part of the remaining flexible portion. A thickness of at least a part of the manipulable portion can be lesser than that of at least a part of remaining flexible portion. The manipulable portion can comprise a thinnest portion and a remaining manipulable portion at least partially surrounding the thinnest portion, and a thickness of the manipulable portion increases from the thinnest portion towards at least a part of the remaining manipulable portion. The flexibility layer provides a smoothness to the surface of the funnel that engages the breast. Further, a negative pressure is created in the funnel for the suction effect to extract milk. The variation in thickness and/or flexibility in the flexible layer prevents the flexible layer to deform at the areas which are to engage the breast thereby preventing the funnel from hurting/biting/pinching the breast when the negative pressure is generated in the funnel.

The rigid portion is formed of a first material having first level of rigidity and the flexible layer is formed of a second material having a second level of rigidity lesser than the first level of rigidity. In some examples, the rigid portion can be made up of material comprising plastic and the flexible layer can be made up of a material comprising silicon.

According to a fifth aspect of the presently disclosed subject matter there is provided a funnel configured to be used with a breast milk pump, the funnel comprising:
 a funnel first open end configured to engage a breast of a user;
 a funnel second open end opposite to the funnel first open end; and
 a funnel intermediate portion extending between the funnel first open end and the funnel second open end, the funnel intermediate portion comprising a manipulable portion configured to deform upon being manipulated by a stimulating mechanism of the breast milk pump, and a remaining portion at least partially surrounding the manipulable portion and configured to retain its shape upon operation of the stimulating mechanism, wherein the manipulable portion has a thinnest portion and a remaining manipulable portion, and a thickness of the manipulable portion increases from the thinnest portion towards at least a part of the remaining manipulable portion.

In some examples, the funnel can be made of a single material, thereby reducing the manufacturing cost. The variation in thickness allows a portion of the funnel to be flexible enough to be manipulated by the stimulating mechanism while other portions being configured to retain their shape to prevent the funnel from hurting/biting/pinching the breast when a negative pressure is generated in the funnel for extraction of milk form the breast.

The thickness of the manipulable portion can increase from the thinnest portion towards at least one of: (i) a first direction extending between the funnel first open end and the funnel second open end, (ii) a second direction perpendicular to the first direction, and (iii) a third direction being a combination of the first and the second direction.

The manipulable portion can be flexible. The thinnest portion can be more flexible than the remaining manipulable portion. The first open end can be configured to retain its shape upon operation of the stimulating mechanism. The second open end is configured to retain its shape upon operation of the stimulating mechanism. The funnel can made up of a material comprising silicon.

According to a sixth aspect of the presently disclosed subject matter there is provided a method for manufacturing a funnel configured to be used with a breast milk pump, the method comprising:

providing a rigid portion having an internal surface facing an interior of the funnel and an opposite external surface, the rigid portion having at least one opening formed therewithin;

over-molding a flexible layer over at least a portion of the internal surface of the rigid portion, thereby covering the at least one opening.

In some examples, over-molding the flexible layer comprises over-molding the flexible over at least a majority of the rigid portion.

According to a seventh aspect of the presently disclosed subject matter there is provided a breast milk pump connectable to a pumping device via a cable comprising a cable first end connectable to the breast milk pump, an opposite cable second end at least partially connectable to the pumping device, and an electrical wiring and an air flow conduit extending between the cable first end and the cable second end, said breast milk pump comprising:

at least one electrically operable component;

a vacuum assembly;

a milk extraction assembly configured to have a negative pressure generated therewithin by the pumping device via the vacuum assembly; and a breast milk pump hybrid connection port configured to be connected to the cable first end, the breast milk pump hybrid connection port comprising a breast milk pump electrical connection sub-port configured to provide an electrical interface between the electrical wiring and the at least one electrically operable component, and a breast milk pump air flow connection sub-port configured to establish an air flow interface between the air flow conduit and the vacuum assembly.

The breast milk pump hybrid connection port can be a compact connection port configured to facilitate both the electrical and air connection required for operation of the breast milk pump by a single action.

The breast milk pump hybrid connection port can be configured to be connected to a hybrid connector constituting the cable first end. The breast milk pump electrical connection sub-port and the breast milk pump air flow connection sub-port can be configured to face in opposite directions. In some examples, the breast milk pump electrical connection sub-port and the breast milk pump air flow connection sub-port can be configured to face in same direction.

The breast milk pump can comprise a proximal portion configured to be positioned towards the breast and a distal portion configured to be positioned away from the breast, said breast milk pump hybrid connection port can be positioned at the distal portion. The breast milk pump hybrid connection port being positioned at the distal portion facilitates the electrical connections to be placed away from the breast thereby enhancing safety of the breast milk pump. The breast milk pump hybrid connection port can be positioned adjacent the vacuum assembly.

The vacuum assembly can comprise a cap configured to close the vacuum assembly, said cap being configured to be in fluid communication with the breast milk pump hybrid connection port. In some examples, the cap can comprise the breast milk pump air flow connection sub-port. In some examples, closing the cap onto the vacuum chamber can establishe a fluid communication between the breast milk pump hybrid connection port and the cap. The breast milk pump hybrid connection port can comprise a coupling means configured to couple the first end of the cable to the breast milk pump. The coupling means can be a screw, a snap fit coupler, a frictional engagement mechanism, etc.

According to an eighth aspect of the presently disclosed subject matter there is provided a pumping device configured to be used in conjunction with a breast milk pump comprising at least one electrically operable component and a vacuum assembly, the pumping device being connectable to the breast milk pump via a cable comprising a cable first end connectable to the breast milk pump, an opposite cable second end connectable to the pumping device, and an electrical wiring and an air flow conduit extending between the cable first end and the cable second end, said pumping device comprising:

an air pump configured to create a vacuum in the vacuum assembly via the air flow conduit; and a pumping device hybrid connection port configured to be connected to the cable second end, the pumping device hybrid connection port comprising a pumping device electrical connection sub-port configured to provide an electrical interface between the electrical wiring and the pumping device, and a pumping device air flow connection sub-port configured to establish an air flow interface between the air flow conduit and the air pump, the pumping device being configured to provide an electrical power to the at least one electrically operable component via the electrical wiring.

The pumping device can comprise an electrical power source. In some examples, the pumping device can be connectable to an external electrical power source and is configured to relay the electrical power to the electrical wiring.

The pumping device can comprise a controller configured to control the air pump and/or a flow of the electrical power to the electrical wiring. The pumping device can comprise an input interface configured to receive commands related to operation of the pumping device. The pumping device can comprise a display interface configured to display a data related to operation of the pumping device.

The pumping device being configured to provide the electrical power as well as to generate vacuum in the breast milk pump makes the breast milk pump easy to use and convenient for storage, as lesser number of components needs to be stored. The pumping device hybrid connection port can be a compact connection port configured to facilitate both the electrical and air connection in a single port body.

According to a ninth aspect of the presently disclosed subject matter there is provided a breast milk extraction kit comprising:

a breast milk pump;

a pumping device;

a cable comprising a cable first end connectable to the breast milk pump, an opposite cable second end connectable to the pumping device, and an electrical wiring and an air flow conduit extending between the cable first end and the cable second end.

The cable can comprise a first hybrid connector constituting the cable first end, said first hybrid connector comprising a first sub connector constituting a first end of the electrical wiring and a second sub connector constituting a first end of the air conduit. The cable can comprise a second hybrid connector constituting the cable second end, said second hybrid connector comprising a first sub connector constituting a second end of the electrical wiring and a second sub connector constituting a second end of the air conduit.

The first hybrid connector can be configured to be connectable to a breast milk pump hybrid connection port of the breast milk pump. The second hybrid connector can be configured to be connectable to a pumping device hybrid connection port of the pumping device.

According to a tenth aspect of the presently disclosed subject matter there is provided a breast milk pump comprising:

a milk extraction assembly comprising a funnel configured to engage a breast of a user, said funnel comprising a flexible portion;

a stimulating mechanism configured to manipulate the flexible portion, said stimulating mechanism comprising one or more selectively inflatable and deflatable elements configured to manipulate the flexible portion upon being inflated and deflated.

The inflatable and deflatable elements of the stimulating mechanism provides a feeling of softness to the breast milk pump and more closely and precisely imitates the tongue action a baby, thereby more efficiently extracting milk from the breast. As compared to the mechanical parts, the stimulating mechanism being configured to manipulate the flexible portion by the inflatable and deflatable elements is gentler on the breast and can be even preferable by a user having sensitive breasts.

The flexible portion can comprise a flexible portion inner surface for facing the breast and an opposite flexible portion outer surface for facing the stimulating mechanism, wherein the stimulating mechanism is configured to manipulate the flexible portion outer surface.

The inflatable and deflatable elements can be configured to cause the flexible portion to have a first shape when deflated and a second shape when inflated. In some examples, in the first shape, the flexible portion can have a first tension therewithin and in the second shape, the flexible portion can have a second tension, greater than the first tension, therewithin. In some examples, the first shape can be an original shape of the flexible portion, i.e., when deflated, the stimulating mechanism may not deform the flexible portion at all.

The stimulating mechanism can comprise at least one fluid port configured to be connected to a fluid pump, said fluid port configured to establish a fluid interface between the fluid pump and each one of the inflatable and deflatable elements. The inflatable and deflatable elements are configured to be inflated and deflated by a fluid pumped by the fluid pump via the fluid port.

The inflatable and deflatable elements can be configured to be inflated and deflated according to a predetermined pattern. The predetermined pattern can be determined so as to most closely imitate the tongue movement of a baby while sucking milk from the breast. The predetermined pattern can be realized by a controller of either the breast milk pump or the fluid pump.

According to an eleventh aspect of the presently disclosed subject matter there is provided a breast milk pump comprising:

a milk extraction assembly comprising a funnel configured to engage a breast of a user, said funnel comprising a flexible portion;

a stimulating mechanism configured to manipulate the flexible portion;

a vacuum assembly configured to generate a negative air pressure within the funnel; and a manually operable trigger mechanism articulated to the stimulating mechanism and to the vacuum assembly and configured to simultaneously operate the stimulating mechanism and the vacuum assembly.

The stimulating mechanism and the vacuum assembly being simultaneously operated makes the breast milk pump more efficient and easy to use as compared to other manually operable breast milk pumps. For instance, a user can easily use the breast milk without the need for electricity and by a single manual action operating the stimulating mechanism and the vacuum assembly. A single action on the trigger mechanism can simultaneously stimulate the breast as well as generate a negative pressure to extract the milk from the breast, and a user can perform such actions repetitively to extract the milk continuously. The stimulating mechanism can have any structure described herein with respect to some of the aspects or can be a structure known in the art as being configured to manipulate the flexible portion of the funnel to serve a general purpose of imitating tongue movements of a baby so as to stimulate the breast for extraction of milk therefrom. In some examples, the stimulating mechanism can comprise a rotational assembly comprising at least one roller configured to rotate about a roller axis to stimulate the flexible portion. The trigger mechanism can be configured to cause the rotation of the roller via a ratchet mechanism. In other examples, the stimulating mechanism can comprise stationary members configured to move up and down by the trigger mechanism.

The stimulating mechanism can have an operative state at which the stimulating mechanism manipulates the flexible portion and an inoperative state, wherein the vacuum assembly can have a negative pressure state at which the vacuum assembly generates the negative air pressure within the funnel and a normal pressure state, wherein the trigger mechanism can have a triggered state associated with the final position and the negative pressure state, and a resting state associated with the initial position and the normal pressure state.

The trigger mechanism can be configured to displace the stimulating mechanism into its operative state and the vacuum assembly into its negative pressure state when the trigger mechanism is displaced into its triggered state.

The trigger mechanism can be configured to displace from the resting state to the triggered state upon application of a force by a user. The trigger mechanism can be configured to return to its resting state upon removal of said force. The trigger mechanism can comprise a biasing member configured to displace the trigger mechanism into its resting state upon removal of said force. The biasing member can be a spring.

The trigger mechanism can comprise a handle, a stimulation trigger member connecting the handle and the stimulating mechanism, and a vacuum trigger connector connecting the handle and the vacuum assembly. The handle can be a pushable handle, a pullable handle or a rotatable handle and can comprise a shape, size, orientation to best suit an ease of operation by the user during use of the breast milk pump.

The breast milk pump can comprise a proximal portion configured to be positioned towards the breast and a distal portion configured to be positioned away from the breast, the stimulating mechanism being positioned at the proximal portion, and the handle and the vacuum assembly being positioned at the distal portion. The positioning of the handle away from the breast makes it easier for the user to operate the handle during use of the breast milk pump.

The stimulation trigger member can comprise a member first end articulated to the stimulating mechanism and a member second end articulated to the handle, the stimulation trigger member being pivotable by the handle about a member pivot axis located between the member first end and the member second end, so as to operate the stimulating mechanism articulated to the member first end. The handle is configured to pivot the stimulation trigger member to displace the stimulating mechanism from its inoperative state to its operative state.

The breast milk pump can further comprise a position adjustment mechanism configured to adjust a position of the stimulating mechanism with respect to the funnel.

The stimulation trigger member can comprise a member first arm extending between the member pivot axis and the member first end, and a member second arm extending between the member pivot axis and the member second end, wherein the member second arm comprises an arm first portion extending from the member pivot axis and an arm second portion extending from the member second end.

At least one of the arm first portion and the arm second portion can comprise a plurality of connecting points positioned along a length thereof, the arm first portion and the arm second portion being connectable to each other at any one of the plurality of connecting points. The connecting points can constitute at least a part of the position adjustment mechanism.

The position adjustment mechanism can comprise an actuator and at least one lever member having a lever first portion articulated to the stimulating mechanism and a lever second portion articulated to the actuator, the lever member being pivotable by the actuator about a lever pivot axis, thereby moving the stimulating mechanism articulated to the lever first portion. The position adjustment mechanism can be configured to move the stimulating mechanism between an initial position at which the stimulating mechanism causes the flexible portion to have a first shape at least prior to operation of the stimulating mechanism, and a final position at which the stimulating mechanism causes the flexible portion to have a second shape different from the first shape at least prior to operation of the stimulating mechanism.

The vacuum assembly can comprise a vacuum chamber having a chamber inner surface, and a membrane configured to be sealingly articulated to the vacuum chamber, the membrane comprising a membrane first surface configured to face the chamber inner surface and an opposite membrane second surface. The vacuum chamber can comprise a chamber first region defined by the chamber inner surface and the membrane first surface, the membrane being configured to be deformed by the trigger mechanism away from the chamber inner surface, thereby generating the negative pressure in the chamber first region and consequently in the milk extraction assembly.

The handle can be connected to the membrane second surface and is configured to pull the membrane second surface so as to deform the membrane away from the chamber inner surface. In some examples, the handle can be configured to be connected to the membrane first surface. The membrane can be configured to remain sealingly articulated to the vacuum chamber when pulled by the handle.

The trigger mechanism can be configured to return to its resting state by virtue of the membrane returning to its original shape upon removal of said force. The membrane can be configured to be elastically deformable, and the elasticity of the membrane tends to displace the handle into its initial state.

The handle can comprise a handle first portion articulated to the vacuum assembly via the vacuum trigger connector and a handle second portion articulated to the stimulating mechanism via the stimulation trigger member, said handle being pivotable about a handle pivot axis located between the handle first portion and the handle second portion. The handle is pivotable about the handle pivot axis to displace the trigger mechanism between the resting state and the triggered state.

The stimulating mechanism can comprise a rotatable part configured to manipulate the flexible portion, and a ratchet mechanism having a first ratchet end connected to the rotatable part and a second ratchet end connected to the stimulation trigger member.

According to a twelfth aspect of the presently disclosed subject matter there is provided a breast milk pump comprising:

a milk extraction assembly comprising a funnel configured to engage a breast of a user, said funnel comprising a flexible portion;

a stimulating mechanism configured to manipulate the flexible portion; and a separating layer configured to isolate the stimulating mechanism from at least the flexible portion.

The presence of an additional separating layer between the flexible portion and the stimulating mechanism prevents the stimulating mechanism from directly engaging the flexible portion. The flexible portion being prevented from direct engagement of moving mechanical parts experience much lesser wear and tear thereby increasing a life of the flexible portion. Further, when the milk extraction assembly is detached from the breast milk pump, the additional separating layer covering the stimulating mechanism prevents a user from intentionally or accidentally come in contact with the stimulating mechanism. The additional separating layer also prevents dust from entering into the stimulating mechanism thereby increasing a life of the stimulating mechanism.

In some examples, the separating layer can be flexible. The separating layer can be detachably attachable to the breast milk pump.

The separating layer can comprise a first separating surface facing the stimulating mechanism and an opposite second separating surface facing the flexible portion, the stimulating mechanism being configured to manipulate the flexible portion via the separating layer, wherein the stimulating mechanism engages the first separating surface, and the second separating surface engages the flexible portion at least when the stimulating mechanism operates.

The breast milk pump can further comprise a body having a component portion, said component portion comprising a front component portion and a rear component portion, said front component portion being configured to accommodate the stimulating mechanism. The separating layer is configured to cover at least a portion of the front component portion.

The body can comprise an outer shell and the separating layer can be connected to the outer shell. In some examples, the outer shell can be formed in two parts constituting two sides of the body and configured to connected to each other. In some examples, separating layer can be configured to be connected to the body while being received at least partially within the connection of the two parts of the outer shell.

EMBODIMENTS

A more specific description is provided in the Detailed Description whilst the following are non-limiting examples of different embodiments of the presently disclosed subject matter. It should be appreciated that Embodiments 1 to 24, correspond to the first aspect of the presently disclosed subject matter; Embodiments 25 to 51, correspond to the second aspect of the presently disclosed subject matter; Embodiments 52 to 73, correspond to the third aspect of the presently disclosed subject matter; Embodiments 74 to 82, correspond to the fourth aspect of the presently disclosed subject matter; Embodiments 83 to 89, correspond to the fifth aspect of the presently disclosed subject matter; Embodiment 90, correspond to the sixth aspect of the presently disclosed subject matter; Embodiments 91 to 99, correspond to the seventh aspect of the presently disclosed subject matter; Embodiments 100 to 105, correspond to the eighth aspect of the presently disclosed subject matter; Embodiments 106 to 108, correspond to the ninth aspect of the presently disclosed subject matter; Embodiments 109 to 114, correspond to the tenth aspect of the presently disclosed subject matter; Embodiments 115 to 138, correspond to the eleventh aspect of the presently disclosed subject matter; Embodiments 139 to 144, correspond to the twelfth aspect of the presently disclosed subject matter;

1. A Breast Milk Pump Comprising:
   a milk extraction assembly comprising a funnel configured to engage a breast of a user, said funnel comprising a flexible portion having a flexible portion inner surface for facing the breast and an opposite flexible portion outer surface;
   a stimulating mechanism facing the flexible portion outer surface and configured to manipulate the flexible portion; and
   a position adjustment mechanism configured to adjust a position of the stimulating mechanism with respect to the funnel, said position adjustment mechanism comprising at least one lever member articulated to the stimulating mechanism, the lever member being pivotable about a lever pivot axis, to move the stimulating mechanism.

2. The breast milk pump according to Embodiment 1, wherein the position adjustment mechanism is configured to move the stimulating mechanism between an initial position at which the stimulating mechanism causes the flexible portion to have a first shape at least prior to operation of the stimulating mechanism, and a final position at which the stimulating mechanism causes the flexible portion to have a second shape different from the first shape at least prior to operation of the stimulating mechanism.

3. The breast milk pump according to Embodiment 2, wherein the position adjustment mechanism is configured to move the stimulating mechanism from the initial position to the final position thereof at least partially in a direction extending along a height of the user.

4. The breast milk pump according to Embodiment 3, wherein the position adjustment mechanism is configured to move the stimulating mechanism from the initial position to the final position thereof majorly in the direction extending along the height of the user.

5. The breast milk pump according to any one of Embodiments 1 to 4, wherein the position adjustment mechanism is configured to move the stimulating mechanism in an arcuate path.

6. The breast milk pump according to any one of Embodiments 1 to 5, wherein the lever member comprises a lever first portion articulated to the stimulating mechanism and a lever second portion, the lever member being configured to be pivoted in response to actuation of the lever second portion.

7. The breast milk pump according to Embodiment 6, wherein the position adjustment mechanism comprises an actuator articulated to the lever second portion, the lever member being pivotable by the actuator.

8. The breast milk pump according to Embodiments 7, wherein the breast milk pump comprises a proximal portion configured to be positioned towards the breast, a distal portion configured to be positioned away from the breast, and a main axis extending therebetween, wherein the actuator is positioned distant from the stimulating mechanism at least in a direction along the main axis.

9. The breast milk pump according to Embodiment 8, wherein the actuator is configured to move the lever second portion.

10. The breast milk pump according to Embodiment 9, wherein said movement of the lever second portion causes the lever first portion to pivot about the lever pivot axis.

11. The breast milk pump according to any one of Embodiments 7 to 10, wherein the position adjustment mechanism is configured for a coarse adjustment of the position of the stimulating mechanism as well as for a fine adjustment of the position of the stimulating mechanism.

12. The breast milk pump according to any one of Embodiments 7 to 11, wherein the actuator comprises a rotatable wheel.

13. The breast milk pump according to Embodiment 12, wherein the position adjustment mechanism is configured to convert said rotation of the wheel into said movement of the stimulating mechanism articulated to the lever first portion.

14. The breast milk pump according to any one of Embodiments 7 to 13, wherein the actuator and the lever second portion constitute at least a part of a cam follower arrangement.

15. The breast milk pump according to Embodiment 14, wherein the actuator comprises a cam and the lever second portion being articulated to the cam via a follower.

16. The breast milk pump according to Embodiment 15, wherein the cam comprises a spiral path extending between a radially outermost end and a radially innermost end thereof.

17. The breast milk pump according to Embodiment 16, when dependent on Embodiment 2, wherein when the follower is at one of the radially innermost end and the radially outermost end, the stimulating mechanism is at the initial position, and when the follower is at other one of the radially innermost end and the radially outermost end, the stimulating mechanism is at the final position.

18. The breast milk pump according to Embodiment 16 or 17, wherein the spiral path comprises an initial portion including the radially innermost end and a terminating portion including the radially outermost end, wherein a curvature of the path is greater at one of the initial and the terminating portion than a curvature of the path at other one of the initial and the terminating portion.

19. The breast milk pump of Embodiment 18, when dependent on Embodiment 11, wherein when the follower is at one of the initial and the final portions, the position adjustment mechanism is configured for a coarse adjustment of the position of the stimulating mechanism, and when the follower is at other one of the initial and the final portions the position adjustment mechanism is configured for a fine adjustment of the position of the stimulating mechanism.

20. The breast milk pump according to any one of Embodiments 15 to 19, wherein the cam is configured to lock the follower at one or more locations between the radially outermost end and the radially innermost end.

21. The breast milk pump according to any one of Embodiments 15 to 20, wherein the cam is configured to prevent a movement of the follower by the lever member.

22. The breast milk pump according to Embodiment 5, further comprising a body and a stabilizing mechanism configured for controlling stabilizing of the lever member with respect to the body.

23. The breast milk pump according to Embodiment 22, wherein the stabilizing mechanism comprises a stabilizing biasing member configured for controlling an extent of the stabilizing of the lever member with respect to the body.

24. The breast milk pump according to Embodiment 23, wherein the stabilizing mechanism comprises a controlling member configured for changing a tension of the stabilizing biasing member.

25. A breast milk pump comprising:
   a milk extraction assembly configured to engage a breast of a user, said milk extraction assembly comprising a pressure interface passage configured to allow passage of air therethrough; and
   a vacuum chamber comprising an orifice and configured to be detachably attachable to the breast milk pump for establishing a fluid communication between the orifice and the pressure interface passage.

26. The breast milk pump according to Embodiment 25, wherein the vacuum chamber is configured to generate a negative pressure within the milk extraction assembly through the orifice and the pressure interface passage.

27. The breast milk pump according to Embodiment 26 or 27, wherein the breast milk pump further comprises a sealing member configured to seal the fluid communication between the pressure interface passage and the orifice.

28. The breast milk pump according to any one of Embodiments 25 to 27, further comprising a body, said milk extraction assembly being detachably connectable to the body.

29. The breast milk pump according to Embodiment 28, wherein the body comprises a chamber supporting wall configured to support the vacuum chamber at least when the vacuum chamber is attached to the breast milk pump.

30. The breast milk pump according to Embodiment 29, wherein the orifice and the pressure interface passage are configured to be in fluid communication through a chamber supporting wall opening formed in the chamber supporting wall.

31. The breast milk pump according to Embodiment 29 or 30, wherein the chamber supporting wall comprises at least one guiding element configured to guide the vacuum chamber into its designated position during attachment thereof to the breast milk pump.

32. The breast milk pump according to Embodiment 31, wherein the vacuum chamber comprises a guidable element configured to be guided by the guiding element during attachment of the vacuum chamber to the breast milk pump.

33. The breast milk pump according to Embodiment 32, wherein the orifice and the pressure interface passage are configured to be in communication through the guiding element.

34. The breast milk pump according to any one of Embodiments 29 to 33, wherein the chamber supporting wall further comprises at least one chamber locking means configured to detachably lock the vacuum chamber when connected to the breast milk pump thereby connecting the vacuum chamber with the body.

35. The breast milk pump according to Embodiment 34, wherein the milk extraction assembly being connectable to and/or detachable from the body irrespective of whether the vacuum chamber is connected to or detached from the body.

36. The breast milk pump according to Embodiment 34 or 35, wherein the vacuum chamber being connectable to and/or detachable from the body irrespective of whether the milk extraction assembly is connected to or detached from the body.

37. The breast milk pump according to any one of Embodiments 25 to 36, further comprising a vacuum assembly comprising the vacuum chamber, a membrane configured to be removably articulated to the vacuum chamber, and a cap configured to close the vacuum chamber at least with the membrane articulated thereto.

38. The breast milk pump according to Embodiment 37, wherein the vacuum chamber comprises a chamber rim and the membrane comprises a membrane rim corresponding to the chamber rim and configured to be positioned on the chamber rim.

39. The breast milk pump according to Embodiment 38, wherein the cap comprises a lip, the cap being configured to sealingly close the vacuum chamber while sealing the membrane rim between the lip and the chamber rim.

40. The breast milk pump according to Embodiment 39, when dependent on Embodiment 29, wherein the cap is configured to be removably locked to the chamber supporting wall.

41. The breast milk pump according to Embodiment 40, when dependent on Embodiment 34, wherein the cap is configured to be removably locked to the chamber supporting wall via the at least one locking means.

42. The breast milk pump according to Embodiment 41, wherein the vacuum chamber comprises a chamber locking portion and the cap comprises a cap locking portion, wherein the at least one locking means comprises a snap connector configured to receive the chamber locking portion and the cap locking portion.

43. The breast milk pump according to Embodiment 42, wherein the snap connector comprises a first snapping portion configured to engage with and to lock the chamber locking portion, and a second snapping portion configured to engage with and to lock the cap locking portion.

44. The breast milk pump according to Embodiment 43, wherein the cap is configured to be detached from the chamber supporting wall together with the vacuum chamber.

45. The breast milk pump according to Embodiment 43, wherein detachment of the cap from the chamber supporting wall causes detachment of the cap locking portion from the second snapping portion, which in turn displaces the snap connector and causes disengagement of the chamber locking portion from the first snapping portion.

46. The breast milk pump according to any one of Embodiments 43 to 45, wherein the cap is configured to be connected to the chamber supporting wall independently of the vacuum chamber.

47. The breast milk pump according to any one of Embodiments 37 to 46, wherein the vacuum chamber has a chamber outer surface configured to face the breast milk pump and an opposite chamber inner surface, and the membrane has a membrane first surface configured to face the chamber inner surface and an opposite membrane second surface configured to face the cap.

48. The breast milk pump according to Embodiment 47, wherein the vacuum chamber comprises a chamber first region defined by the chamber inner surface and the membrane first surface, and a chamber second region defined by the membrane second surface and the cap, the chamber first region configured to be in fluid communication with the milk extraction assembly through the orifice and the pressure interface passage when the vacuum chamber is connected to the breast milk pump.

49. The breast milk pump according to Embodiment 48, wherein the chamber second region is configured to be fluidly connected, via the cap, to a pumping device configured to generate a vacuum at the chamber second region.

50. The breast milk pump according to Embodiment 49, wherein in response to the vacuum, the membrane is configured to be deformed towards the chamber second region and generate a negative pressure in the chamber first region, and consequently in the milk extraction assembly via the orifice and the pressure interface passage.

51. The breast milk pump according to any one of Embodiments 37-50, wherein the cap further comprises a flange configured to engage with the membrane, wherein the cap is configured to tightly receive at least a portion of the membrane between the flange and the vacuum chamber when closed.

52. A body for a breast milk pump comprising a milk extraction assembly configured to be directly connected to a milk collection container to establish a milk flow path, the body comprising:
   a component portion configured to accommodate one or more operational components to be used in conjunction with the breast milk pump;

an interface portion configured to be engaged with the milk extraction assembly while embracing the connection of the milk extraction assembly and the milk collection container.

53. The body according to Embodiment 52, wherein the component portion is configured to at least partially engage the milk extraction assembly to allow the one or more operational components to be operated in conjunction with the milk extraction assembly.

54. The body according to Embodiment 52 or 53, wherein the component portion comprises a front component portion configured to at least partially engage the milk extraction assembly, and a rear component portion, the interface portion being positioned between the front component portion and the rear component portion.

55. The body according to Embodiment 54, wherein the operational components comprise at least one electrically operable component, the front component portion being configured to accommodate the electrically operable component, the rear component portion comprising an electrical connection port configured to facilitate a connection of the breast milk pump with an electrical power source, and the interface portion being configured to at least partially accommodate an electrical connection extending from the electrical connection port to the electrically operable component.

56. The body according to Embodiment 54 or 55, wherein the milk extraction assembly comprises a funnel and the operational components comprise a stimulating mechanism configured to manipulate at least a flexible portion of the funnel, the front component portion being configured to accommodate the stimulating mechanism.

57. The body according to Embodiment 56, when dependent on Embodiment 55, wherein the stimulating mechanism is the electrically operable component.

58. The body according to Embodiment 56 or 57, wherein the operational components further comprise a position adjustment mechanism configured to adjust a position of the stimulating mechanism with respect to the funnel, the front component portion being configured to accommodate at least a first adjustment component of the position adjustment mechanism, the rear component portion being configured to accommodate at least a second adjustment component of the position adjustment mechanism, and the interface portion being configured to at least partially accommodate a connecting component of the position adjustment mechanism connecting the first adjustment component and the second adjustment component.

59. The body according to Embodiment 58, wherein the connecting component is a lever member, the first adjustment component is a lever first portion, and the second adjustment component comprises an actuator articulated to a lever second portion.

60. The body according to Embodiment 59, wherein the body comprises an access opening configured to allow access therethrough to the actuator.

61. The body according to any one of Embodiments 54 to 60, wherein the breast milk pump further comprises a vacuum assembly, the rear component portion being configured to accommodate the vacuum assembly and the interface portion being configured to at least partially accommodate an air flow path extending between the vacuum assembly and the milk extraction assembly.

62. The body according to Embodiment 61, further comprising a chamber supporting wall separating the interface portion and the rear component portion, said chamber supporting wall comprising a chamber supporting wall opening being configured to establish a communication between the interface portion and the rear component portion.

63. The body according to Embodiment 62, wherein the air flow path extends through the chamber supporting wall opening.

64. The body according to any one of Embodiments 61 to 63, wherein the rear component portion comprises an air flow connection port configured to facilitate an air flow connection between the vacuum assembly and a pumping device.

65. The body according to Embodiment 64, when dependent on Embodiment 55, wherein the electrical connection port and the air flow connection port constitute a hybrid connection port.

66. The body according to any one of Embodiments 52 to 65, wherein the body further comprises a separating layer configured to isolate the one or more operational components from the milk extraction assembly.

67. The body according to Embodiment 66, when dependent on Embodiment 54, wherein the separating layer is configured to isolate the front component portion from the milk extraction assembly.

68. The body according to Embodiment 66 or 67, wherein the separating layer is flexible.

69. The body according to any one of Embodiments 66 to 68, wherein the separating layer is detachably attachable to the body.

70. The body according to any one of Embodiments 52 to 69, wherein the body is configured to allow the milk extraction assembly to be detachably connected to the milk collection container through the interface portion.

71. The body according to Embodiment 70, wherein the body is configured to be detachably connected to the breast milk pump via said connection of the milk extraction assembly and the milk collection container.

72. The body according to Embodiments 70 or 71, wherein the interface portion comprises a through-passage configured to allow the milk extraction assembly to be detachably connected to the milk collection container therethrough.

73. The body according to any one of Embodiments 52 to 72, wherein the body is configured to constitute a housing for the breast milk pump.

74. A funnel configured to be used with a breast milk pump, the funnel comprising:
a rigid portion having an internal surface facing an interior of the funnel and an opposite external surface, the rigid portion having at least one opening formed therewithin; and
a flexible layer over-molded over at least a portion of the internal surface of the rigid portion, the flexible layer comprising a manipulable portion extending at least partially over the at least one opening and configured to be manipulated by a stimulating mechanism.

75. The funnel according to Embodiment 74, wherein the flexible layer is over-molded over at least a majority of the internal surface of the rigid portion.

76. The funnel according to Embodiment 74 or 75, wherein the manipulable portion is configured to be manipulated via the at least one opening.

77. The funnel according to any one of Embodiment 74 to 76, wherein the manipulable portion is configured to engage at least a part of the breast at least when manipulated.

78. The funnel according to any one of Embodiments 74 to 77, wherein the flexible layer further comprises a remaining flexible portion at least partially surrounding the manipulable portion.

79. The funnel according to Embodiment 78, wherein the manipulable portion is more flexible than at least a part of the remaining flexible portion.

80. The funnel according to Embodiment 78 or 79, wherein a thickness of at least a part of the manipulable portion is lesser than that of at least a part of remaining flexible portion.

81. The funnel according to any one of Embodiments 78 to 80, wherein the manipulable portion comprises a thinnest portion and a remaining manipulable portion at least partially surrounding the thinnest portion, and a thickness of the manipulable portion increases from the thinnest portion towards at least a part of the remaining manipulable portion.

82. The funnel according to any one of Embodiments 74 to 81, wherein the rigid portion is formed of a first material having first level of rigidity and the flexible layer is formed of a second material having a second level of rigidity lesser than the first level of rigidity.

83. A funnel configured to be used with a breast milk pump, the funnel comprising:
a funnel first open end configured to engage a breast of a user;
a funnel second open end opposite to the funnel first open end; and
a funnel intermediate portion extending between the funnel first open end and the funnel second open end, the funnel intermediate portion comprising a manipulable portion configured to deform upon being manipulated by a stimulating mechanism of the breast milk pump, and a remaining portion at least partially surrounding the manipulable portion and configured to retain its shape upon operation of the stimulating mechanism, wherein the manipulable portion has a thinnest portion and a remaining manipulable portion, and a thickness of the manipulable portion increases from the thinnest portion towards at least a part of the remaining manipulable portion.

84. The funnel according to Embodiment 83, wherein the thickness of the manipulable portion increases from the thinnest portion towards at least one of:
(i) a first direction extending between the funnel first open end and the funnel second open end,
(ii) a second direction perpendicular to the first direction, and
(iii) a third direction being a combination of the first and the second direction.

85. The funnel according to Embodiment 83 or 84, wherein the manipulable portion is flexible.

86. The funnel according to any one of Embodiments 83 to 85, wherein the thinnest portion is more flexible than of the remaining manipulable portion.

87. The funnel according to any one of Embodiments 83 to 86, wherein the first open end is configured to retain its shape upon operation of the stimulating mechanism.

88. The funnel according to any one of Embodiments 83 to 87, wherein the second open end is configured to retain its shape upon operation of the stimulating mechanism.

89. The funnel according to any one of Embodiments 83 to 88, wherein the funnel is made up of a material comprising silicon.

90. A method for manufacturing a funnel configured to be used with a breast milk pump, the method comprising:
   providing a rigid portion having an internal surface facing an interior of the funnel and an opposite external surface, the rigid portion having at least one opening formed therewithin; and
   over-molding a flexible layer over at least a portion of the internal surface of the rigid portion, thereby covering the at least one opening.

91. A breast milk pump connectable to a pumping device via a cable comprising a cable first end connectable to the breast milk pump, an opposite cable second end at least partially connectable to the pumping device, and an electrical wiring and an air flow conduit extending between the cable first end and the cable second end, said breast milk pump comprising:
   at least one electrically operable component;
   a vacuum assembly;
   a milk extraction assembly configured to have a negative pressure generated therewithin by the pumping device via the vacuum assembly; and
   a breast milk pump hybrid connection port configured to be connected to the cable first end, the breast milk pump hybrid connection port comprising a breast milk pump electrical connection sub-port configured to provide an electrical interface between the electrical wiring and the at least one electrically operable component, and a breast milk pump air flow connection sub-port configured to establish an air flow interface between the air flow conduit and the vacuum assembly.

92. The breast milk pump according to Embodiment 91, wherein the breast milk pump hybrid connection port is configured to be connected to a hybrid connector constituting the cable first end.

93. The breast milk pump according to Embodiment 91 or 92, wherein the breast milk pump electrical connection sub-port and the breast milk pump air flow connection sub-port are configured to face in opposite directions.

94. The breast milk pump according to any one of Embodiments 91 to 93, wherein the breast milk pump comprises a proximal portion configured to be positioned towards the breast and a distal portion configured to be positioned away from the breast, said breast milk pump hybrid connection port being positioned at the distal portion.

95. The breast milk pump according to any one of Embodiments 91 to 94, wherein the breast milk pump hybrid connection port is positioned adjacent the vacuum assembly.

96. The breast milk pump according to Embodiment 95, wherein the vacuum assembly comprises a cap configured to close the vacuum assembly, said cap being configured to be in fluid communication with the breast milk pump hybrid connection port.

97. The breast milk pump according to Embodiment 96, wherein the cap comprises the breast milk pump air flow connection sub-port.

98. The breast milk pump according to Embodiment 95 or 96, wherein closing the cap onto the vacuum chamber establishes a fluid communication between the breast milk pump hybrid connection port and the cap.

99. The breast milk pump according to any one of Embodiments 91 to 98, wherein the breast milk pump hybrid connection port comprises a coupling means configured to couple the first end of the cable to the breast milk pump.

100. A pumping device configured to be used in conjunction with a breast milk pump comprising at least one electrically operable component and a vacuum assembly, the pumping device being connectable to the breast milk pump via a cable comprising a cable first end connectable to the breast milk pump, an opposite cable second end connectable to the pumping device, and an electrical wiring and an air flow conduit extending between the cable first end and the cable second end, said pumping device comprising:
   an air pump configured to create a vacuum in the vacuum assembly via the air flow conduit; and
   a pumping device hybrid connection port configured to be connected to the cable second end, the pumping device hybrid connection port comprising a pumping device electrical connection sub-port configured to provide an electrical interface between the electrical wiring and the pumping device, and a pumping device air flow connection sub-port configured to establish an air flow interface between the air flow conduit and the air pump, the pumping device being configured to provide an electrical power to the at least one electrically operable component via the electrical wiring.

101. The pumping device according to Embodiment 100, wherein the pumping device comprises an electrical power source.

102. The pumping device according to Embodiment 100, wherein the pumping device is connectable to an external electrical power source and is configured to relay the electrical power to the electrical wiring.

103. The pumping device according to any one of Embodiments 100 to 102, wherein the pumping device comprises a controller configured to control the air pump and/or a flow of the electrical power to the electrical wiring.

104. The pumping device according to any one of Embodiments 100 to 103, wherein the pumping device comprises an input interface configured to receive commands related to operation of the pumping device.

105. The pumping device according to any one of Embodiments 100 to 104, wherein the pumping device comprises a display interface configured to display a data related to operation of the pumping device.

106. A breast milk extraction kit comprising:
   a breast milk pump according to any one of Embodiments 91 to 99;
   a pumping device according to any one of Embodiments 100 to 105; and
   a cable comprising a cable first end connectable to the breast milk pump, an opposite cable second end connectable to the pumping device, and an electrical wiring and an air flow conduit extending between the cable first end and the cable second end.

107. The breast milk extraction kit according to Embodiment 106, wherein the cable comprises a first hybrid connector constituting the cable first end, said first hybrid connector comprising a first sub connector constituting a first end of the electrical wiring and a second sub connector constituting a first end of the air conduit.

108. The breast milk extraction kit according to Embodiment 106 or 107, wherein the cable comprises a second hybrid connector constituting the cable second end, said second hybrid connector comprising a first sub connector constituting a second end of the electrical wiring and a second sub connector constituting a second end of the air conduit.

109. A breast milk pump comprising:

a milk extraction assembly comprising a funnel configured to engage a breast of a user, said funnel comprising a flexible portion;

a stimulating mechanism configured to manipulate the flexible portion, said stimulating mechanism comprising one or more selectively inflatable and deflatable elements configured to manipulate the flexible portion upon being inflated and deflated.

110. The breast milk pump according to Embodiment 109, wherein the flexible portion comprises a flexible portion inner surface for facing the breast and an opposite flexible portion outer surface for facing the stimulating mechanism, wherein the stimulating mechanism is configured to manipulate the flexible portion outer surface.

111. The breast milk pump according to Embodiment 109 or 110, wherein the inflatable and deflatable elements are configured to cause the flexible portion to have a first shape when deflated and a second shape when inflated.

112. The breast milk pump according to any one of Embodiments 109 to 111, wherein the stimulating mechanism comprises at least one fluid port configured to be connected to a fluid pump, said fluid port configured to establish a fluid interface between the fluid pump and each one of the inflatable and deflatable elements.

113. The breast milk pump according to Embodiment 112, wherein the inflatable and deflatable elements are configured to be inflated and deflated by a fluid pumped by the fluid pump via the fluid port.

114. The breast milk pump according to any one of Embodiments 109 to 113, wherein the inflatable and deflatable elements are configured to be inflated and deflated according to a predetermined pattern.

115. A breast milk pump comprising:

a milk extraction assembly comprising a funnel configured to engage a breast of a user, said funnel comprising a flexible portion;

a stimulating mechanism configured to manipulate the flexible portion;

a vacuum assembly configured to generate a negative air pressure within the funnel; and a manually operable trigger mechanism articulated to the stimulating mechanism and to the vacuum assembly, and configured to simultaneously operate the stimulating mechanism and the vacuum assembly.

116. The breast milk pump according to Embodiment 115, wherein the stimulating mechanism has an operative state at which the stimulating mechanism manipulates the flexible portion and an inoperative state, wherein the vacuum assembly has a negative pressure state at which the vacuum assembly generates the negative air pressure within the funnel and a normal pressure state, wherein the trigger mechanism has a triggered state associated with the final position and the negative pressure state, and a resting state associated with the initial position and the normal pressure state.

117. The breast milk pump according to Embodiment 116, wherein the trigger mechanism is configured to displace the stimulating mechanism into its operative state and the vacuum assembly into its negative pressure state when the trigger mechanism is displaced into its triggered state.

118. The breast milk pump according to Embodiment 116 or 117, wherein the trigger mechanism is configured to displace from the resting state to the triggered state upon application of a force by a user.

119. The breast milk pump according to Embodiment 118, wherein the trigger mechanism is configured to return to its resting state upon removal of said force.

120. The breast milk pump according to Embodiment 119, wherein the trigger mechanism comprises a biasing member configured to displace the trigger mechanism into its resting state upon removal of said force.

121. The breast milk pump according to any one of Embodiments 115 to 120, wherein the trigger mechanism comprises a handle, a stimulation trigger member connecting the handle and the stimulating mechanism, and a vacuum trigger connector connecting the handle and the vacuum assembly.

122. The breast milk pump according to Embodiment 121, wherein the breast milk pump comprises a proximal portion configured to be positioned towards the breast and a distal portion configured to be positioned away from the breast, the stimulating mechanism being positioned at the proximal portion, and the handle and the vacuum assembly being positioned at the distal portion.

123. The breast milk pump according to Embodiment 121 or 122, wherein the stimulation trigger member comprises a member first end articulated to the stimulating mechanism and a member second end articulated to the handle, the stimulation trigger member being pivotable by the handle about a member pivot axis located between the member first end and the member second end, so as to operate the stimulating mechanism articulated to the member first end.

124. The breast milk pump according to Embodiment 123, when dependent on Embodiment 116, wherein the handle is configured to pivot the stimulation trigger member to displace the stimulating mechanism from its inoperative state to its operative state.

125. The breast milk pump according to any one of Embodiments 115 to 124, further comprising a position adjustment mechanism configured to adjust a position of the stimulating mechanism with respect to the funnel.

126. The breast milk pump according to Embodiment 125, when dependent on Embodiment 123, wherein the stimulation trigger member comprises a member first arm extending between the member pivot axis and the member first end, and a member second arm extending between the member pivot axis and the member second end, wherein the member second arm comprises an arm first portion extending from the member pivot axis and an arm second portion extending from the member second end.

127. The breast milk pump according to Embodiment 126, wherein at least one of the arm first portion and the arm second portion comprises a plurality of connecting points positioned along a length thereof, the arm first portion and the arm second portion being connectable to each other at any one of the plurality of connecting points.

128. The breast milk pump according to Embodiment 127, wherein the connecting points constitute at least a part of the position adjustment mechanism.

129. The breast milk pump according to Embodiment 125, wherein said position adjustment mechanism comprises an actuator and at least one lever member having a lever first portion articulated to the stimulating mechanism and a lever second portion articulated to the actuator, the lever member being pivotable by the actuator about a lever pivot axis, thereby moving the stimulating mechanism articulated to the lever first portion.

130. The breast milk pump according to Embodiment 129, wherein the position adjustment mechanism is configured to move the stimulating mechanism between an initial position at which the stimulating mechanism causes the flexible portion to have a first shape at least prior to operation of the stimulating mechanism, and a final position at which the stimulating mechanism causes the flexible portion to have a second shape different from the first shape at least prior to operation of the stimulating mechanism.

131. The breast milk pump according to any one of Embodiments 115 to 130, wherein the vacuum assembly comprises a vacuum chamber having a chamber inner surface, and a membrane configured to be sealingly articulated to the vacuum chamber, the membrane comprising a membrane first surface configured to face the chamber inner surface and an opposite membrane second surface.

132. The breast milk pump according to Embodiment 131, wherein the vacuum chamber comprises a chamber first region defined by the chamber inner surface and the membrane first surface, the membrane being configured to be deformed by the trigger mechanism away from the chamber inner surface, thereby generating the negative pressure in the chamber first region and consequently in the milk extraction assembly.

133. The breast milk pump according to Embodiment 132, when dependent on Embodiment 121, wherein the handle is connected to the membrane second surface and is configured to pull the membrane second surface so as to deform the membrane away from the chamber inner surface.

134. The breast milk pump according to Embodiment 133, wherein the membrane is configured to remain sealingly articulated to the vacuum chamber when pulled by the handle.

135. The breast milk pump according to Embodiment 134, when dependent on Embodiment 119, wherein the trigger mechanism is configured to return to its resting state by virtue of the membrane returning to its original shape upon removal of said force.

136. The breast milk pump according to Embodiment 121 or any one of Embodiments 122 to 135, when dependent on Embodiment 121, wherein the handle comprises a handle first portion articulated to the vacuum assembly via the vacuum trigger connector and a handle second portion articulated to the stimulating mechanism via the stimulation trigger member, said handle being pivotable about a handle pivot axis located between the handle first portion and the handle second portion.

137. The breast milk pump according to Embodiment 136, when dependent on Embodiment 116, wherein the handle is pivotable about the handle pivot axis to displace the trigger mechanism between the resting state and the triggered state.

138. The breast milk pump according to Embodiment 121, wherein the stimulating mechanism comprises a rotatable part configured to manipulate the flexible portion, and a ratchet mechanism having a first ratchet end connected to the rotatable part and a second ratchet end connected to the stimulation trigger member.

139. A breast milk pump comprising:
    a milk extraction assembly comprising a funnel configured to engage a breast of a user, said funnel comprising a flexible portion;
    a stimulating mechanism configured to manipulate the flexible portion; and
    a separating layer configured to isolate the stimulating mechanism from at least the flexible portion.

140. The breast milk pump according to Embodiment 139, wherein the separating layer is flexible.

141. The breast milk pump according to Embodiment 139 or 140, wherein the separating layer is detachably attachable to the breast milk pump.

142. The breast milk pump according to any one of Embodiments 139 to 141, wherein the separating layer comprises a first separating surface facing the stimulating mechanism and an opposite second separating surface facing the flexible portion, the stimulating mechanism being configured to manipulate the flexible portion via the separating layer, wherein the stimulating mechanism engages the first separating surface, and the second separating surface engages the flexible portion at least when the stimulating mechanism operates.

143. The breast milk pump according to any one of Embodiments 139 to 142, wherein the breast milk pump further comprises a body having a component portion, said component portion comprising a front component portion and a rear component portion, said front component portion being configured to accommodate the stimulating mechanism.

144. The breast milk pump according to Embodiment 143, wherein the separating layer is configured to cover at least a portion of the front component portion.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1A:
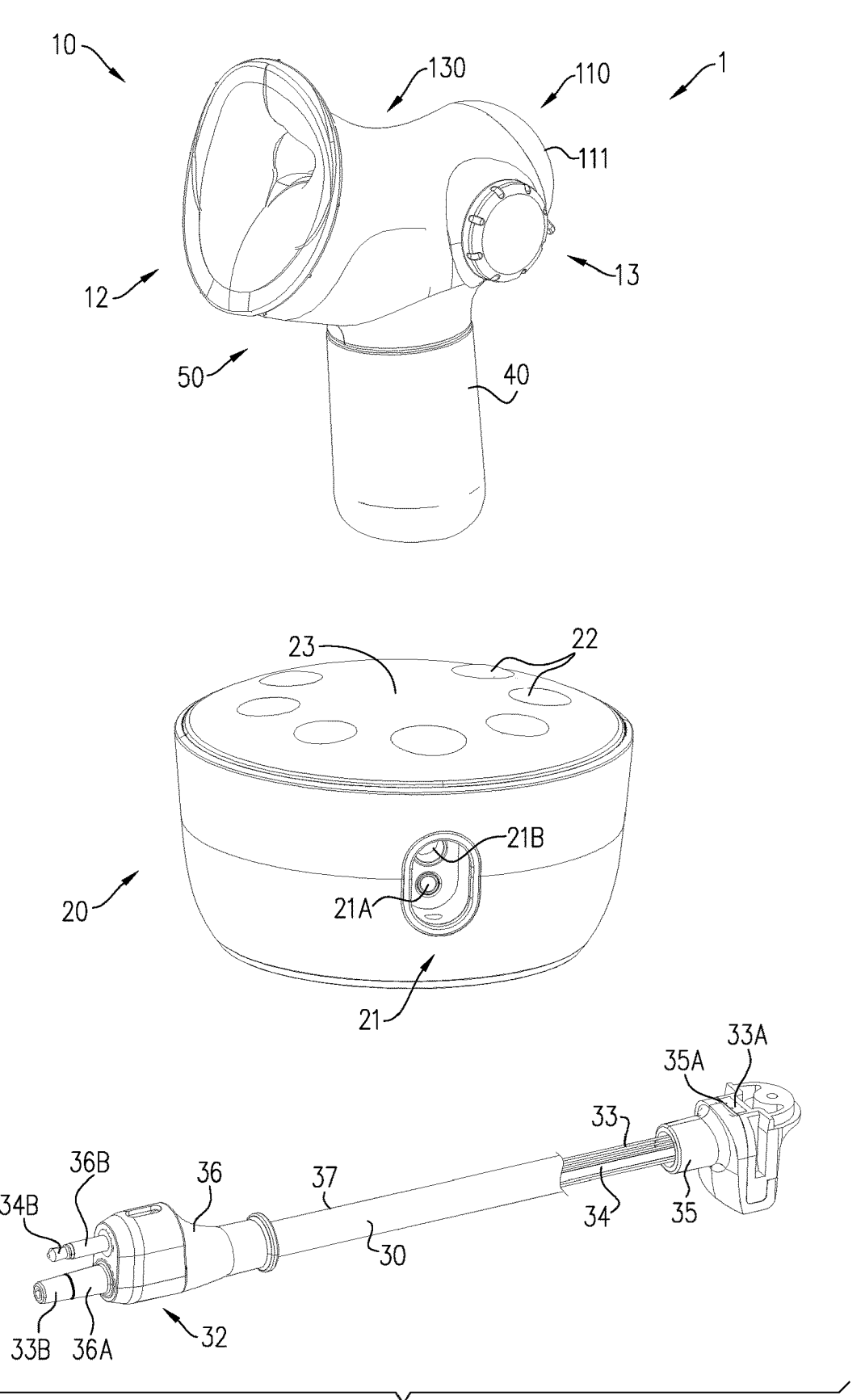
FIG. 1A illustrates a breast milk extraction kit according to certain aspects of the presently disclosed subject matter in a disconnected manner.

Attention is first directed to FIGS. 1A to 1F of the drawings illustrating a breast milk extraction kit 1 comprising a breast milk pump 10, a pumping device 20, and a cable 30. The breast milk pump 10 can be a breast milk pump of any of the several aspects detailed herein above or can include some or all features of the breast milk pump of any of these aspects. The cable 30 has a cable first end 31 connectable to the breast milk pump 10, an opposite cable second end 32 connectable to the pumping device 20, and an electrical wiring 33 and an air flow conduit 34 extending between the cable first end 31 and the cable second end 32. The cable first end 31 is constituted by a first hybrid connector 35 having a first sub connector 35A constituting a first end 33A of the electrical wiring 33 and a second sub connector 35B constituting a first end 34A of the air conduit. The cable 30 comprises a second hybrid connector 36 constituting the cable second end 32, and including a first sub connector 36A constituting a second end 33B of the electrical wiring 33 and a second sub connector 36B constituting a second end 34B of the air conduit 34.

The first hybrid connector 35 is configured to be connectable to a breast milk pump hybrid connection port 11 of the breast milk pump 10. The second hybrid connector 36 is configured to be connectable to a pumping device hybrid connection port 21 of the pumping device 20. The cable 30 comprises a cable shell 37 including the electrical wiring 33 and the air flow conduit 34 therewithin. Additionally, the first hybrid connector 35 has a coupling means 38 configured to be coupled to a corresponding coupling means 14 of the breast milk pump (best seen in FIG. 1D).

The pumping device 20 comprises an air pump (internal to the pumping device 20) configured to pump air out of the breast milk pump 10 to create a vacuum therewithin via the air flow conduit 34. The pumping device 20 has a pumping device hybrid connection port 21 configured to be connected to the cable second end 32. The pumping device hybrid connection port 21 comprises a pumping device electrical connection sub-port 21A configured to provide an electrical interface between the electrical wiring 33 and the pumping device 20, and a pumping device air flow connection sub-port 21B configured to establish an air flow interface between the air flow conduit 34 and the air pump. The pumping device 20 is configured to provide an electrical power to the breast milk pump 10 via the electrical wiring 33.

In some examples, the pumping device 20 can include an electrical power source. In other examples, the pumping device 20 can be connectable to an external electrical power source and is configured to relay the electrical power to the electrical wiring 33.

The pumping device has a controller (internal to the pumping device) configured to control the air pump and/or a flow of the electrical power to the electrical wiring 33. The pumping device 20 comprises an input interface 22 configured to receive commands related to operation of the pumping device 20. The pumping device 20 includes a display interface 23 configured to display a data related to operation of the pumping device 20. The data can be an air pressure, a value indicating the electrical power, operational state of the pumping device, etc.

The breast milk pump 10 comprises an electrically operable component 100 (best seen in FIGS. 3C and 3D), a vacuum assembly 110, a milk extraction assembly 130 configured to have a negative pressure generated therewithin by the pumping device 20 via the vacuum assembly 110, and a breast milk pump hybrid connection port 11 configured to be connected to the cable first end 31. In the illustrated examples, the electrically operable component is the stimulating mechanism 100. In other examples, the electrically operable component 100 can be any other component that is electrically operated such as sensors, controller, actuators, rechargeable power sources, etc. The breast milk pump hybrid connection port 11 comprises a breast milk pump electrical connection sub-port 11A (best seen in FIG. 1E) configured to provide an electrical interface between the electrical wiring 33 and the at least one electrically operable component 100, and a breast milk pump air flow connection sub-port 11B configured to establish an air flow interface between the air flow conduit 34 and the vacuum assembly 110.

The breast milk pump hybrid connection port 11 is configured to be connected to the first hybrid connector 35. In the illustrated example, the breast milk pump electrical connection sub-port 11A and the breast milk pump air flow connection sub-port 11B are configured to face in opposite directions. In some examples, the breast milk pump electrical connection sub-port 11A and the breast milk pump air flow connection sub-port 11B can be configured to face in same direction.

Figure 1B:
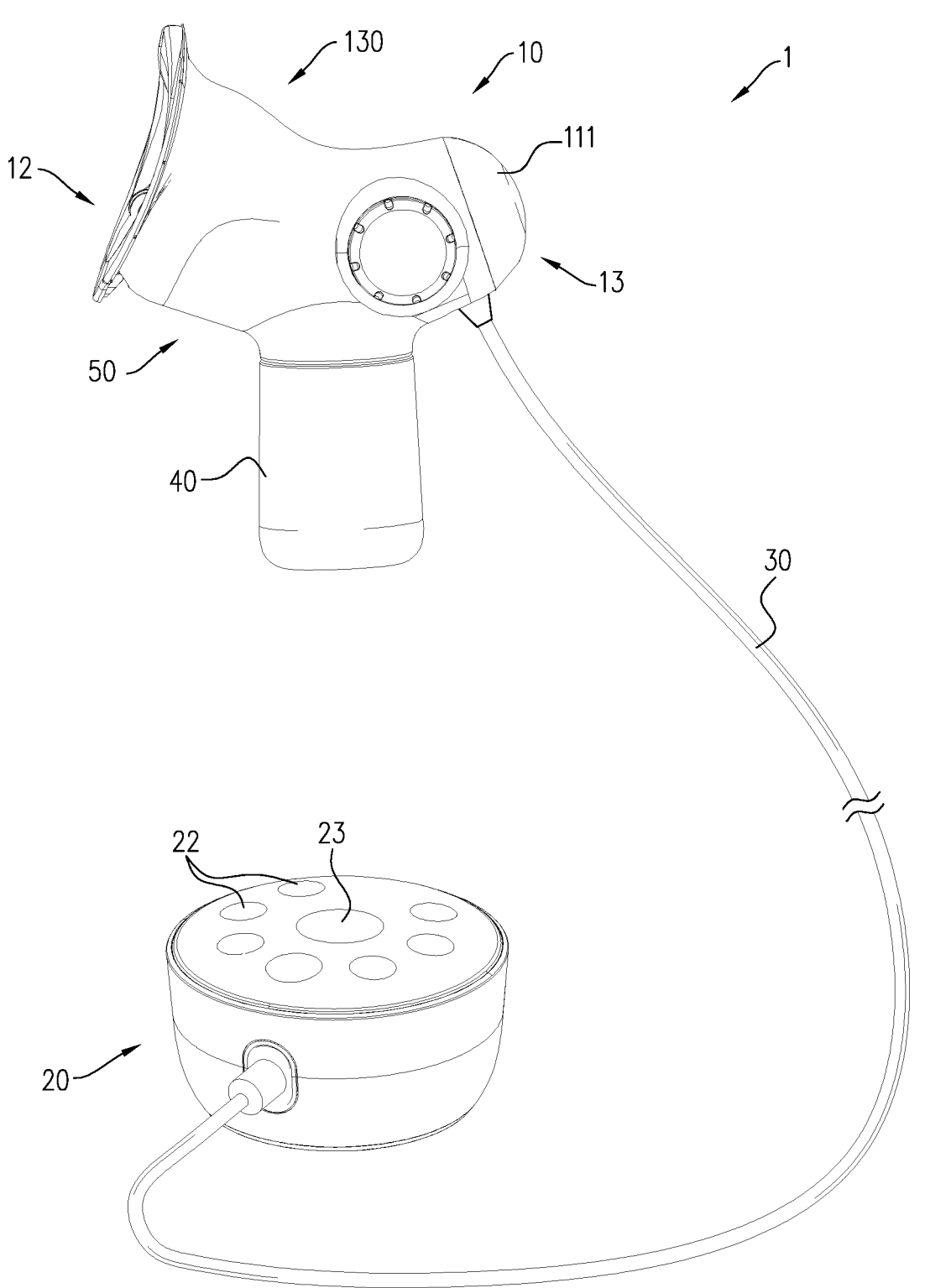
FIG. 1B illustrates the breast milk extraction kit of FIG. 1A with breast milk pump and pumping device connected via cable.
Figure 1C:
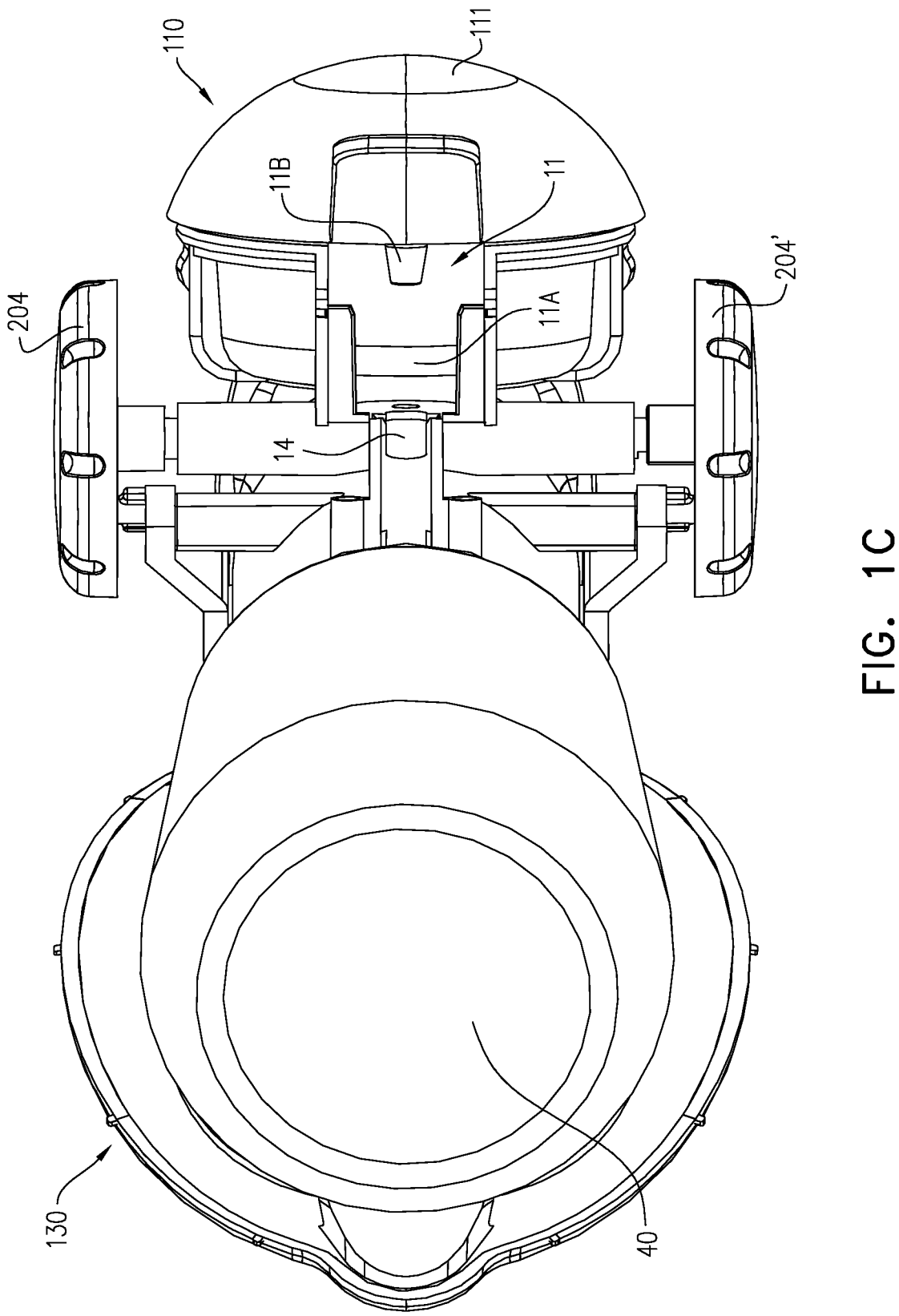
FIG. 1C illustrates a bottom view of a breast milk pump according to certain aspects of the presently disclosed subject matter with a body removed for illustration purposes.
Figure 1D:
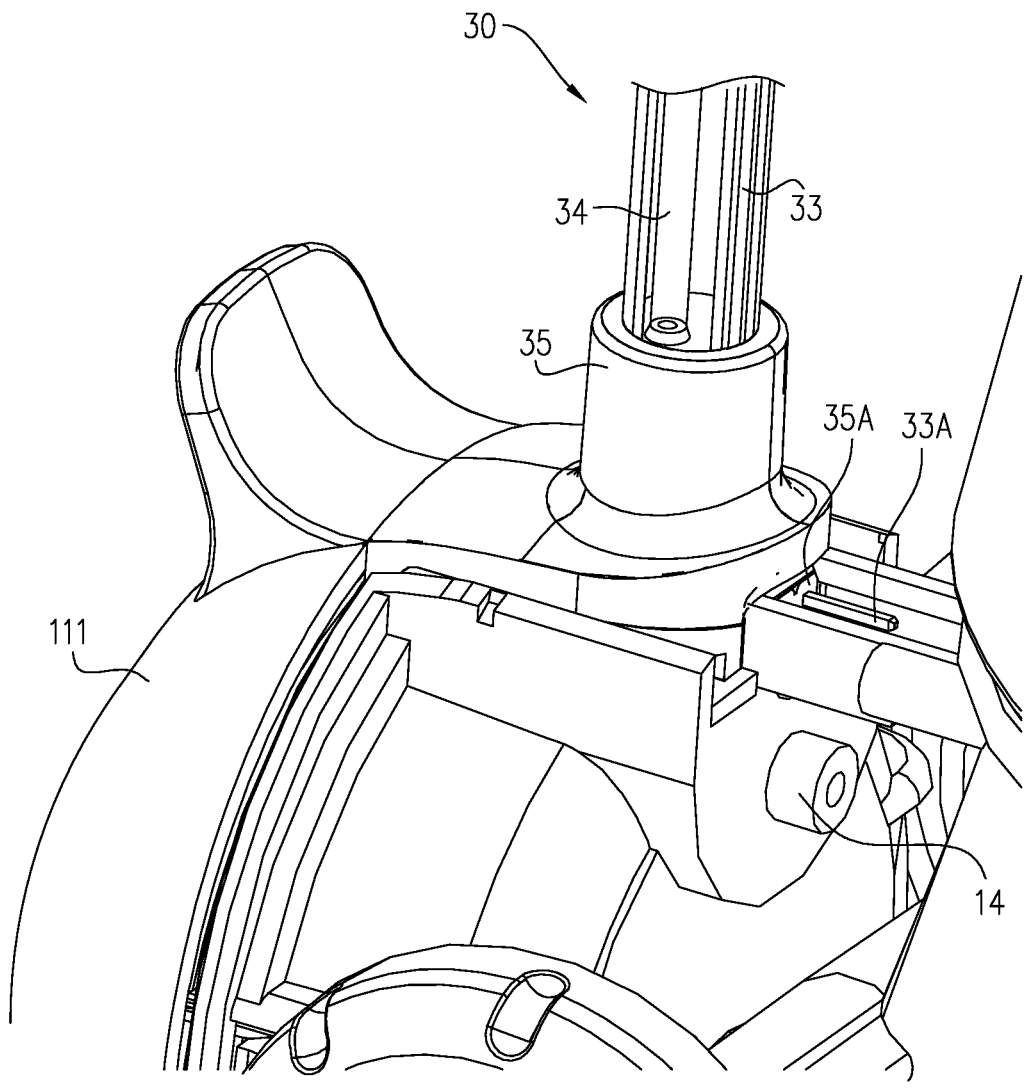
FIG. 1D illustrates an enlarged view of a bottom perspective view of the breast milk pump illustrated in FIG. 1B with a cable connected thereto.
Figure 1E:
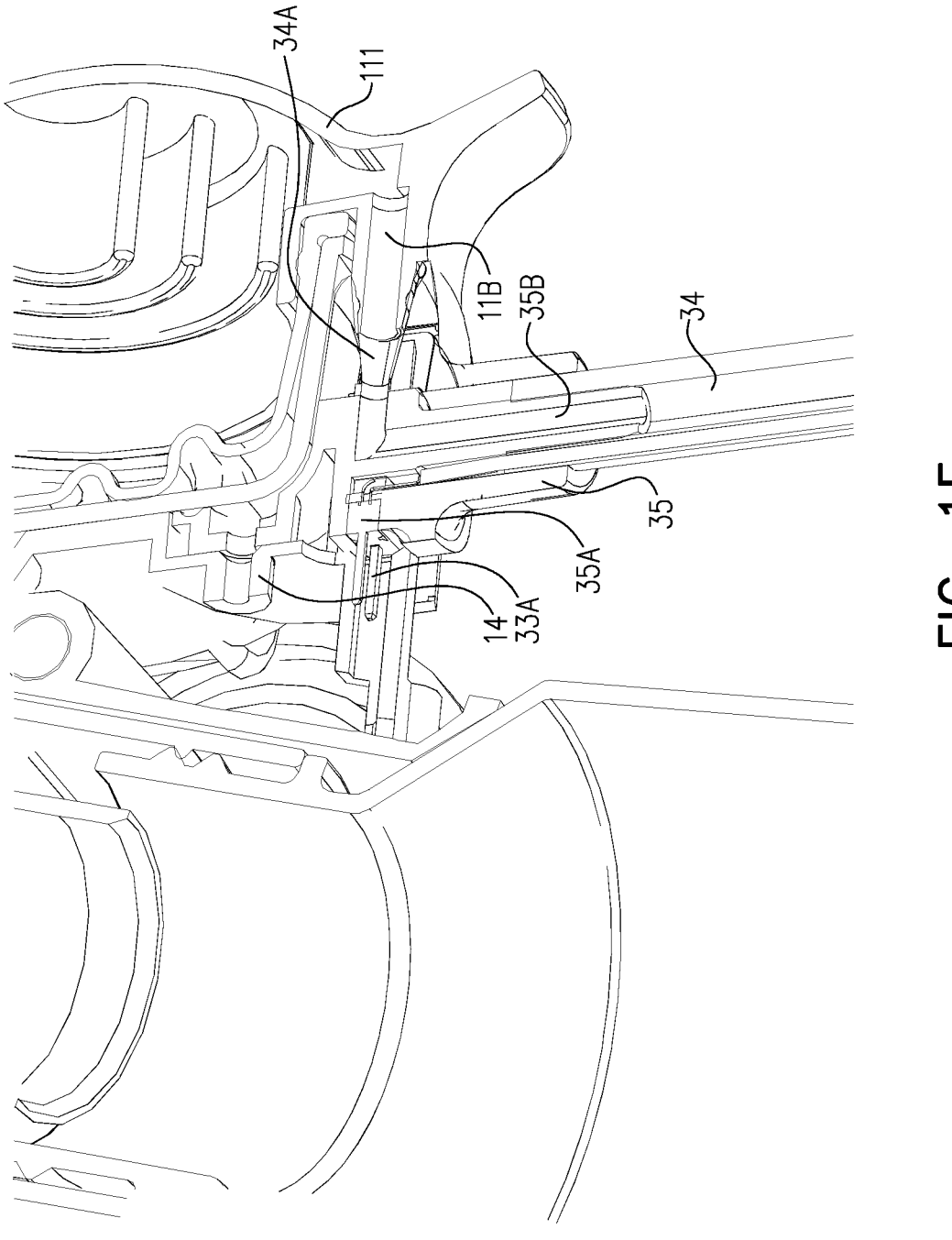
FIG. 1E illustrates a cross-section of FIG. 1C.
Figure 1F:
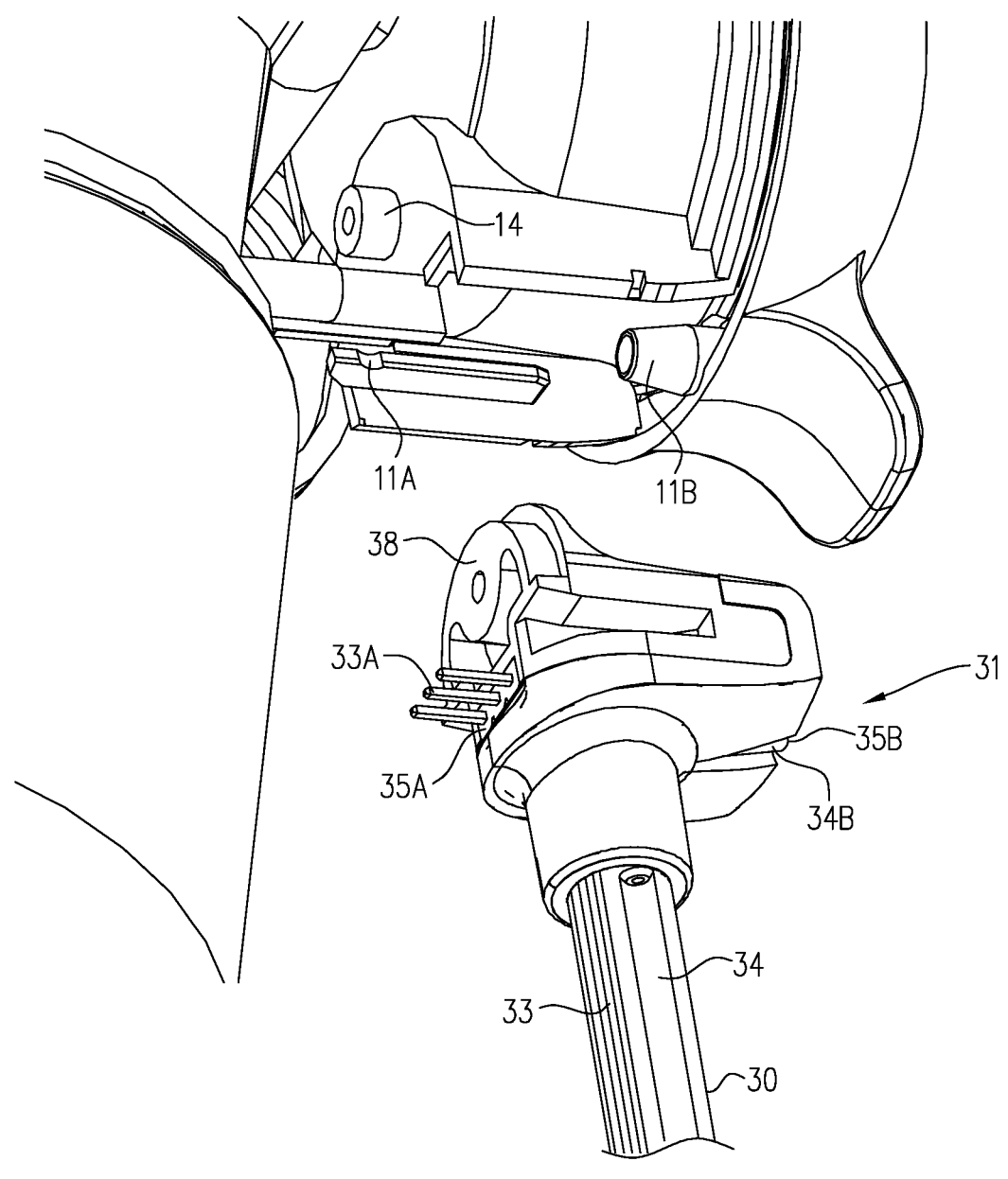
FIG. 1F illustrates an enlarged view of a bottom perspective view of the breast milk pump illustrated in FIG. 1B with the cable disconnected therefrom.
Figure 1G:
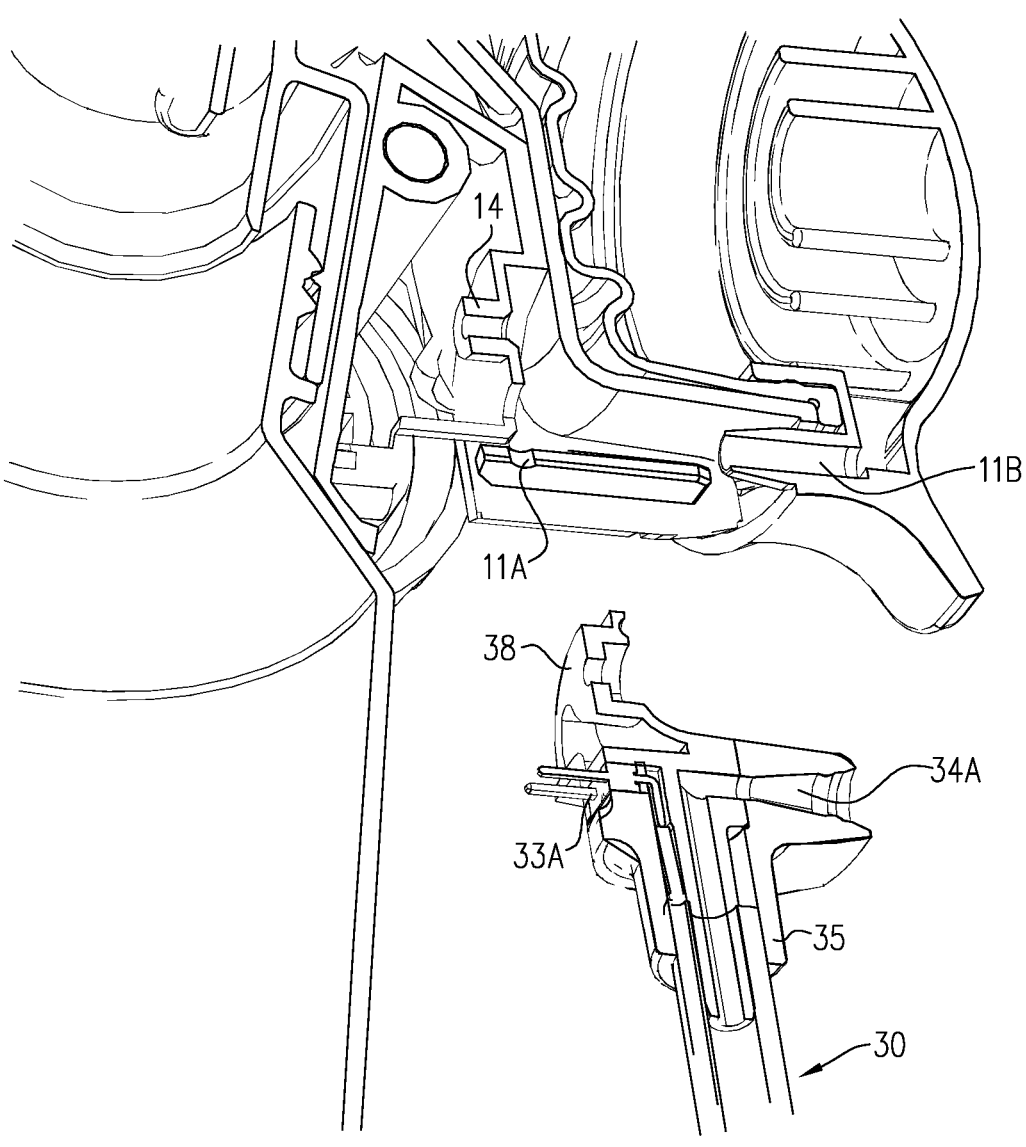
FIG. 1G illustrates a cross-section of FIG. 1E.

The breast milk pump 10 comprises a proximal portion 12 configured to be positioned towards the breast and a distal portion 13 configured to be positioned away from the breast. As can be seen in FIG. 1B, the breast milk pump hybrid connection port 11 is positioned at the distal portion 13. In some examples, the breast milk pump hybrid connection port 11 can be positioned at the proximal portion or any other location between the proximal portion and the distal portion.

The vacuum assembly 110 can comprise a cap 111 configured to close the vacuum assembly 110. The cap is configured to be in fluid communication with the breast milk pump hybrid connection port 11. In the illustrated example, the cap comprises the breast milk pump air flow connection sub-port 11B. As can be seen in 1D, closing the cap 111 onto the vacuum chamber 112 establishes the fluid communication between the breast milk pump hybrid connection port 11 and the cap 111. The breast milk pump hybrid connection port 11 comprises a coupling means 14 configured to couple the coupling means 38 of the cable 30 to the breast milk pump 10. The coupling means can be a screw, a snap fit coupler, a frictional engagement mechanism, etc.

Figure 2A:
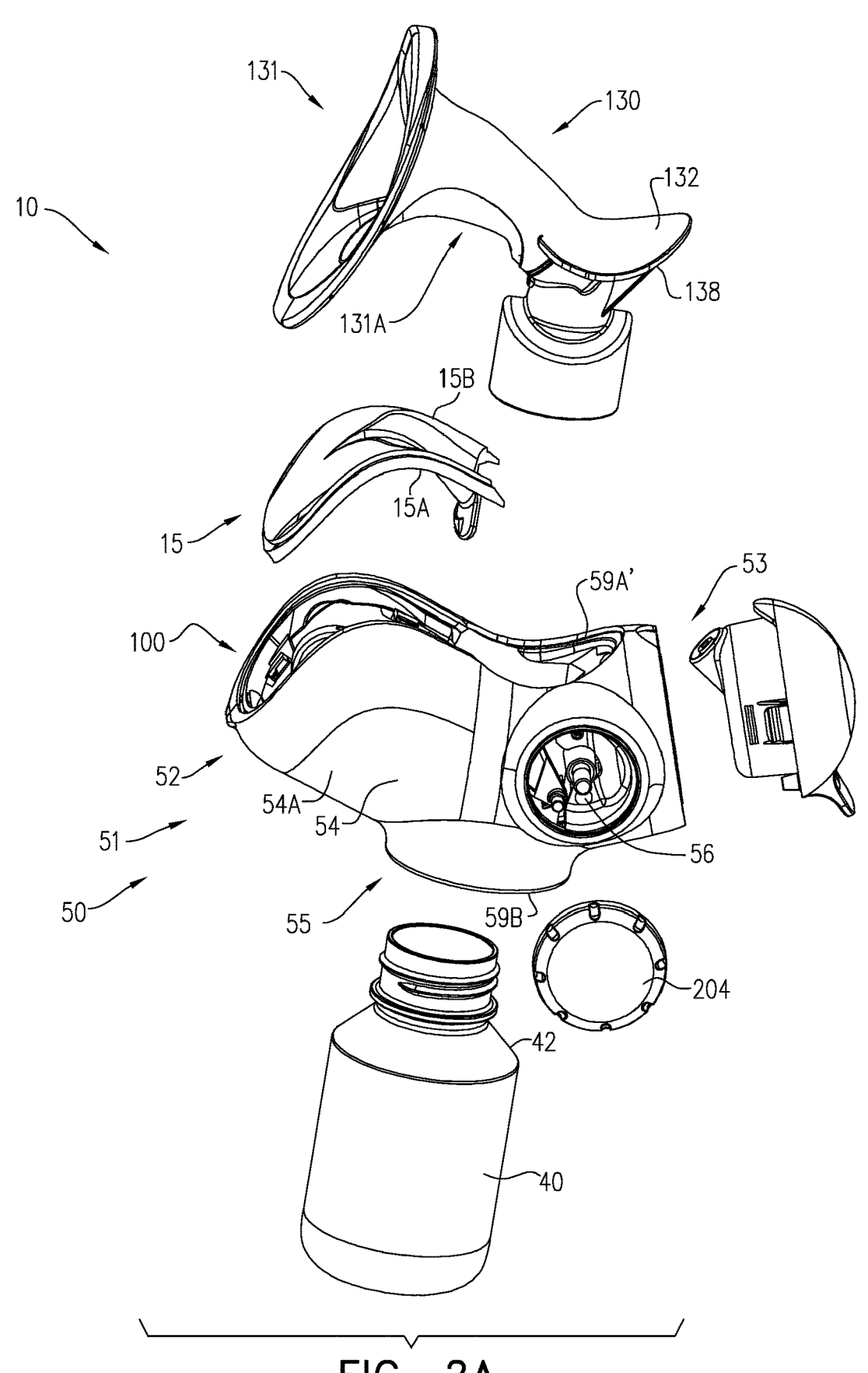
FIG. 2A illustrates a partially exploded view of a breast milk pump according to certain aspects of the presently disclosed subject matter.
Figure 2B:
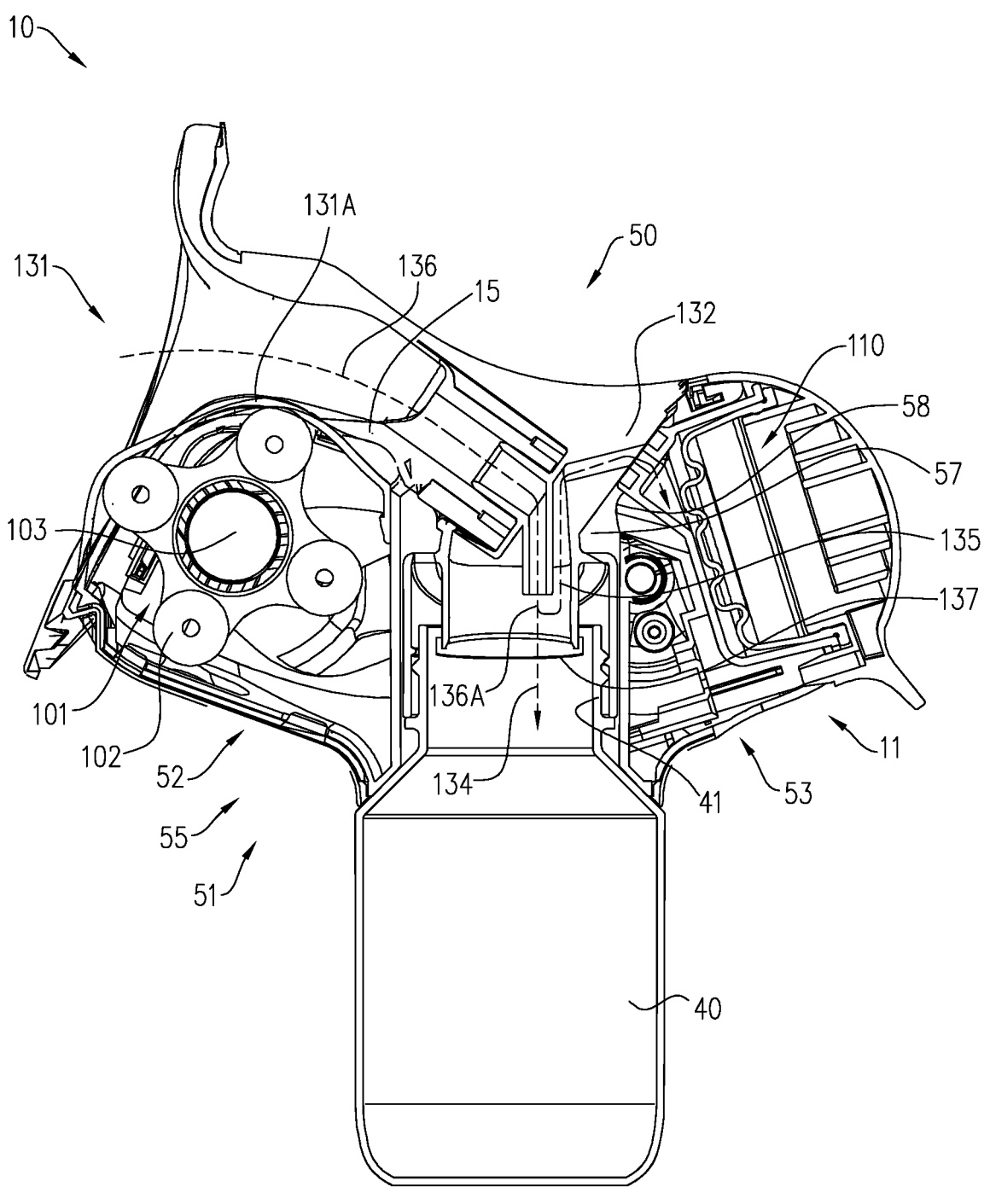
FIG. 2B illustrates a cross-section of the assembled breast milk pump illustrated in FIG. 2A.
Figure 2C:
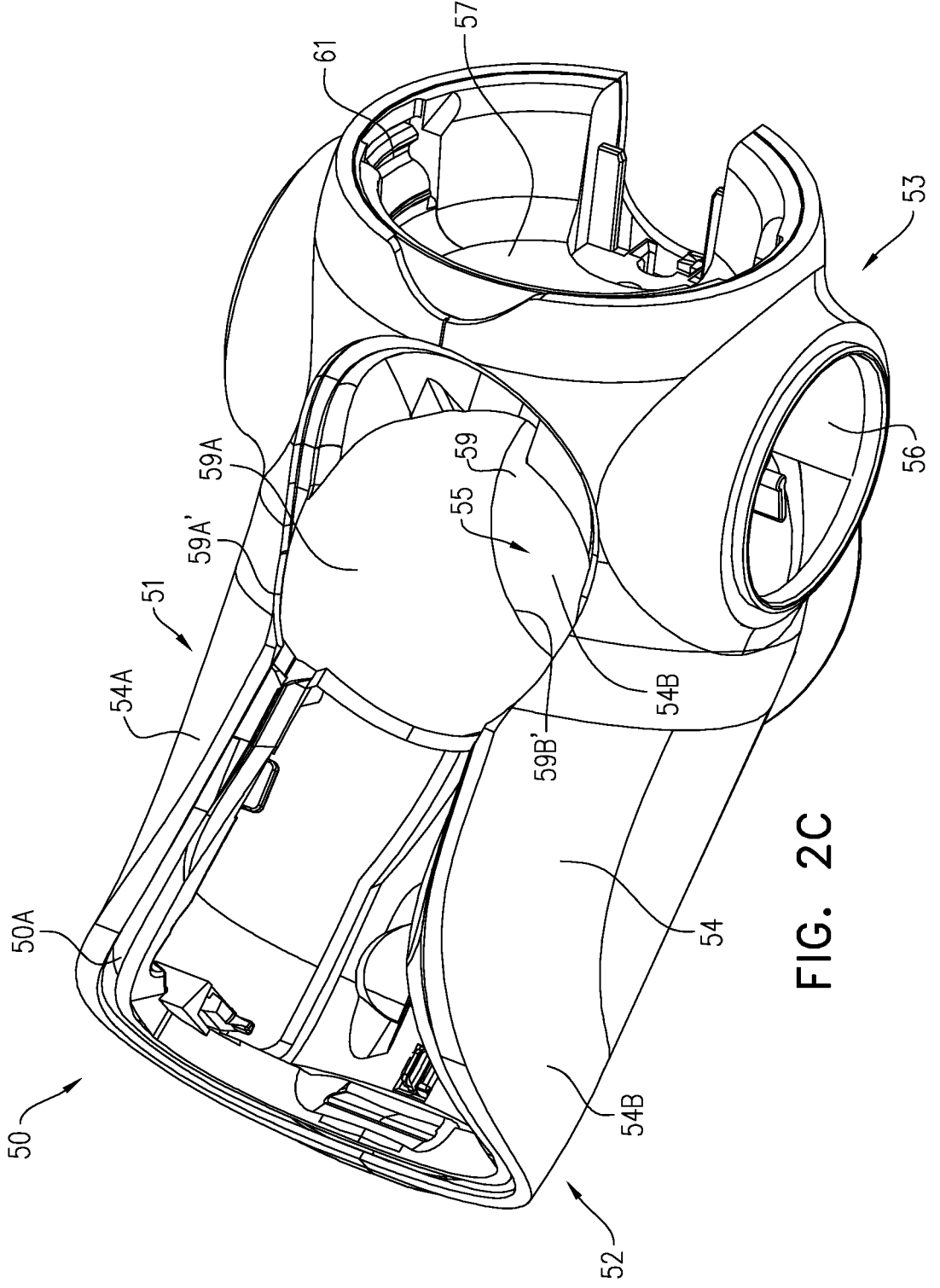
FIG. 2C illustrates a top perspective view of a body configured to be used with the breast milk pump illustrated in FIG. 2A.

FIGS. 2A-2C illustrate the breast milk pump 10 according to certain aspects of the presently disclosed subject matter. The breast milk pump 10 comprises the milk extraction assembly 130 comprising a funnel 131 configured to engage a breast of a user. The funnel has a flexible portion 131A. The breast milk pump has the stimulating mechanism 100 configured to manipulate the flexible portion 131A. A separating layer 15 is configured to isolate the stimulating mechanism 100 from the flexible portion 131A. In some examples, the separating layer 15 can be flexible. The separating layer 15 is detachably attachable to the breast milk pump 10.

The separating layer 15 comprises a first separating surface 15A facing the stimulating mechanism 100 and an opposite second separating surface 15B facing the flexible portion 131A. The stimulating mechanism 100 is configured to manipulate the flexible portion 131A via the separating layer 15. The stimulating mechanism 100 engages the first separating surface 15A and the second separating surface 15B engages the flexible portion 131A at least when the stimulating mechanism 100 operates.

In the illustrated example, the stimulating mechanism comprises a rotational assembly 101 comprising rollers 102 being rotatable by a motor 103. The rollers 102 manipulate the flexible portion 131A at least when rotated. In other examples, the stimulating mechanism 100 can have any structure described herein with respect to some of the aspects or can be a structure known in the art as being configured to manipulate the flexible portion of the funnel to serve a general purpose of imitating tongue movements of a baby so as to stimulate the breast for extraction of milk therefrom.

The breast milk pump 10 further comprises a body 50 having a component portion 51 comprising a front component portion 52 and a rear component portion 53. The front component portion is configured to accommodate the stimulating mechanism 100. The separating layer 15 is configured to cover the front component portion 52 so as to isolate the stimulating mechanism 100 from the flexible portion 131A.

The body 50 comprises an outer shell 54 and the separating layer 15 is configured to be connected to the outer shell 54. In the illustrated example, the outer shell 54 is formed in two parts 54A and 54B, each constituting a side of the body 50 and are configured to be connected to each other while receiving a chassis 50A of the body 50 therebetween. The separating layer 15 is configured to be connected to the body 50 by being clamped between the two parts of the outer shell 54 and the chassis 50A.

The component portion 51 is configured to accommodate one or more operational components, such as the stimulating mechanism 100, the breast milk pump hybrid connection port 11, the vacuum assembly 110, etc., to be used in conjunction with the breast milk pump 10. The body 50 further comprises an interface portion 55 configured to be engaged with the milk extraction assembly 130 while embracing the connection 41 of the milk extraction assembly 130 and the milk collection container 40.

The component portion 51 is configured to at least partially engage the milk extraction assembly 130. The interface portion 55 is positioned between the front component portion 52 and the rear component portion 53. The front component portion 52 is configured to be positioned near the breast of the user while the rear component portion 53 is configured to be positioned away from the breast of the user.

The front component portion 52 is configured to accommodate the electrically operable component 100 and the rear component portion comprises an electrical connection port, which in the illustrated example is the breast milk pump electrical connection sub-port 11A, configured to facilitate a connection of the breast milk pump 10 with an electrical power source, such as the pumping device 20. The interface portion is configured to at least partially accommodate an electrical connection extending from the electrical connection port 11A to the electrically operable component 100.

The milk extraction assembly further comprises a cone member 132 configured to engage the body 50 and/or to be connected thereto. The funnel 131 and the cone member 132 can be integrally formed or can be separately manufactured and can be configured to be detachably attachable to each other. The funnel 131 is connected to the milk collection container 40 as well as to the vacuum assembly 110 via the cone member 132. The cone member 132 at least partially comprises a milk flow path 134 extending between the milk extraction assembly 130 and the milk collection container 40, and an air flow path 135 extending between the milk extractions assembly 130 and the vacuum assembly 110. The milk flow path 134 and the air flow path 135 comprise a common portion 136 and separate at a path separating point 136A. The cone member 132 further comprises a one-way valve 137 configured to be positioned in the milk flow path 134 at a point downstream of the path separating point 136A. The one-way valve 137 is positioned at an opening of the cone member 132 configured to be connected to the milk collection container 40. The one-way valve 137 prevents air and/or milk to flow from the milk collection container 40 into the milk extraction assembly 130 at least when a negative pressure is created in the milk extraction assembly 130. The interface portion 55 of the body 50 embraces at least a part of the cone member 132 and the connection 41 of the milk extraction assembly 130 and the milk collection container 40.

The operational components can further comprise a position adjustment mechanism 200 (explained in greater details herein below with reference to FIGS. 3A-3E) configured to adjust a position of the stimulating mechanism 100 with respect to the funnel 131. The front component portion 52 is configured to accommodate at least a first adjustment component of the position adjustment mechanism 200, the rear component portion 53 being configured to accommodate at least a second adjustment component of the position adjustment mechanism 200. The interface portion 55 is configured to at least partially accommodate a connecting component of the position adjustment mechanism 200 connecting the first adjustment component and the second adjustment component. The connecting component is a lever member 201, the first adjustment component is a lever first portion 202, and the second adjustment component comprises an actuator 204 articulated to a lever second portion 203. The body 50 comprises an access opening 56 configured to allow access therethrough to the actuator 204.

The rear component portion 53 is configured to accommodate the vacuum assembly 110 and the interface portion 55 is configured to at least partially accommodate the air flow path 135 extending between the vacuum assembly 110 and the milk extraction assembly 130.

The body 50 further comprises a chamber supporting wall 57 separating the interface portion 55 and the rear component portion 53. The chamber supporting wall 57 comprises a chamber supporting wall opening 58 configured to establish a communication between the interface portion 55 and the rear component portion 53. The air flow path 135 extends through the chamber supporting wall opening 58.

The rear component portion 53 comprises the air flow connection port, which in the illustrated example is the breast milk pump air flow connection sub-port 11B, configured to facilitate an air flow connection between the vacuum assembly 110 and the pumping device 20.

The body 50 is configured to allow the milk extraction assembly 130 to be detachably connected to the milk collection container 40 through the interface portion 55. The body 50 is configured to be detachably connected to the breast milk pump 10 via said connection 41 of the milk extraction assembly 130 and the milk collection container 40. The body 50 is configured to be received between at least a part 138 of the milk extraction assembly 130 and at least a part 42 of the milk collection container 40 thereby stabilizing the body 40 together with the milk extraction assembly 130 and the milk collection container 40 when they are connected through the body 40.

The interface portion 55 comprises a through-passage 59 configured to allow the milk extraction assembly 130 to be connected to the milk collection container 40 therethrough to establish the milk flow path 134. The through-passage 59 comprises a first through opening 59A configured to receive therethrough the milk extraction assembly 130 and a second through opening 59B configured to receive therethrough the milk collection container 40. Thus, the milk extraction assembly 130 and the milk collection container 40 are connected to each other within the through-passage 59. The first through opening 59A has a rim 59A' configured to engage the milk extraction assembly 130, at the part 138, and the second through opening 59B has a rim 59B' configured to engage the milk collection container 40, at the part 42. The through-passage 59 is configured such that the rims 59A' and 59B' of the first through opening 59A and the second through opening 59B are configured to be received between the milk extraction assembly 130 and the milk collection container 40 thereby stabilizing the body 50 together with the milk extraction assembly 130 and the milk collection container 40 when they are connected through the body 50. The body 50 is configured to constitute a housing 16 for the breast milk pump 10. The body 50 constitutes at least a part of the outermost surface of the breast milk pump 10.

FIGS. 3A-3E illustrate the breast milk pump 10 according to certain aspects of the presently disclosed subject matter. The breast milk pump 10 comprises the milk extraction assembly 130 comprising the funnel 131 configured to engage the breast of the user. The funnel 131 comprises the flexible portion 131A having a flexible portion inner surface 131A' for facing the breast and an opposite flexible portion outer surface 131A" facing the stimulating mechanism 100.

The position adjustment mechanism 200 is configured to adjust a position of the stimulating mechanism with respect to the funnel 131. The position adjustment mechanism comprises the lever member 201 articulated to the stimulating mechanism 100, the lever member is pivotable about a lever pivot axis LPA to move the stimulating mechanism 100.

The position of the stimulating mechanism 100 at least partially defines a size of an opening 131B of the funnel configured to receive the breast, thus, by adjusting the position of the stimulating mechanism, a dimension of the opening of the funnel 131 is controlled.

The stimulating mechanism 100 comprises a rotational assembly 101 comprising rollers 102 being rotatable by a motor 103. The rollers 102 manipulate the flexible portion 131A at least when rotated. In other examples, the stimulating mechanism 100 can have any structure described herein with respect to some of the aspects or can be a structure known in the art as being configured to manipulate the flexible portion of the funnel to serve a general purpose of imitating tongue movements of a baby so as to stimulate the breast for extraction of milk therefrom. can have any structure described herein with respect to some of the aspects or can be a structure known in the art as being configured to manipulate the flexible portion of the funnel to serve a general purpose of imitating tongue movements of a baby so as to stimulate the breast for extraction of milk therefrom.

Figure 3A:
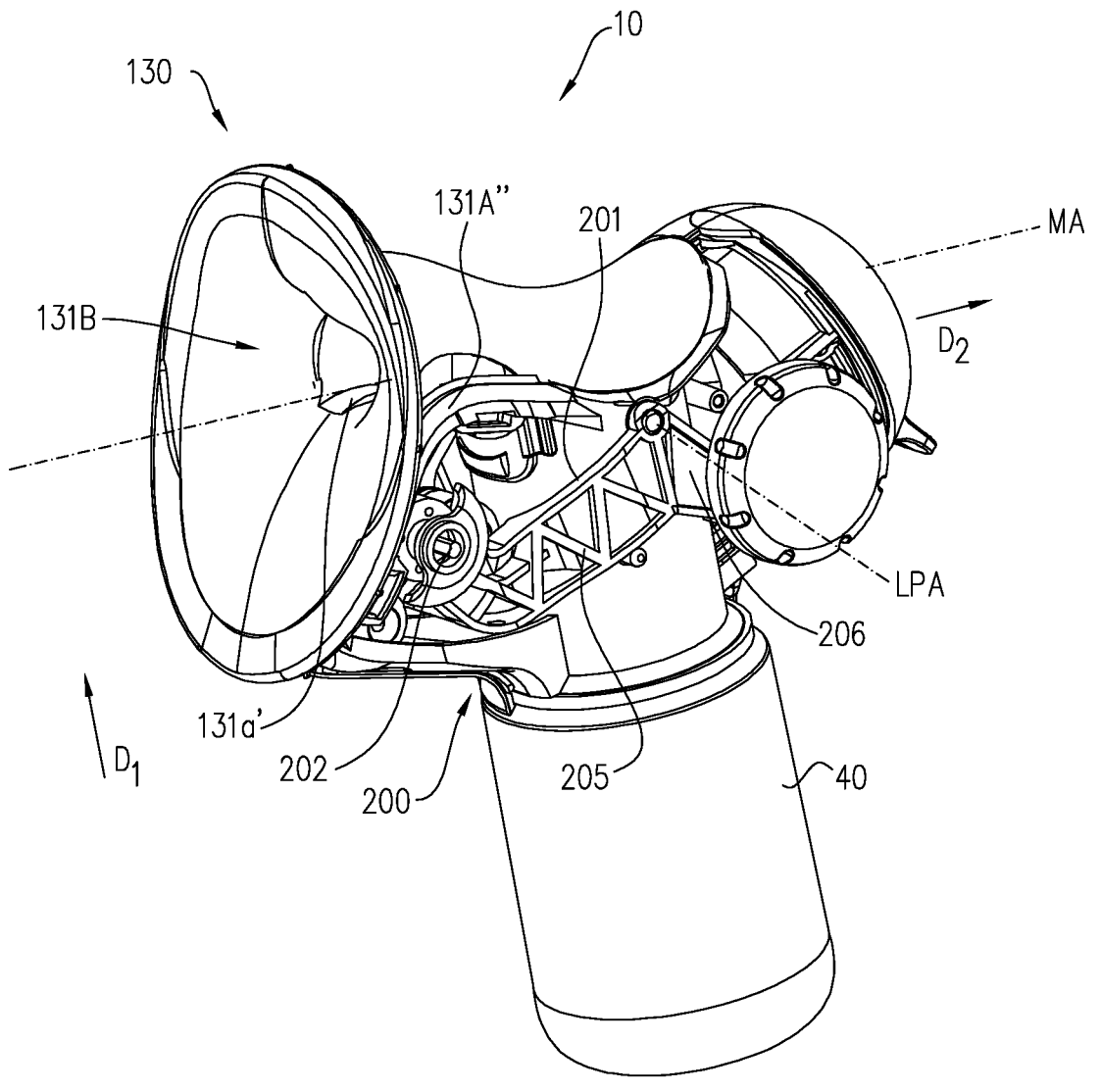
FIG. 3A illustrates a side perspective view of a breast milk pump according to certain aspects of the presently disclosed subject matter with an outer shell removed for illustration purposes.
Figure 3B:
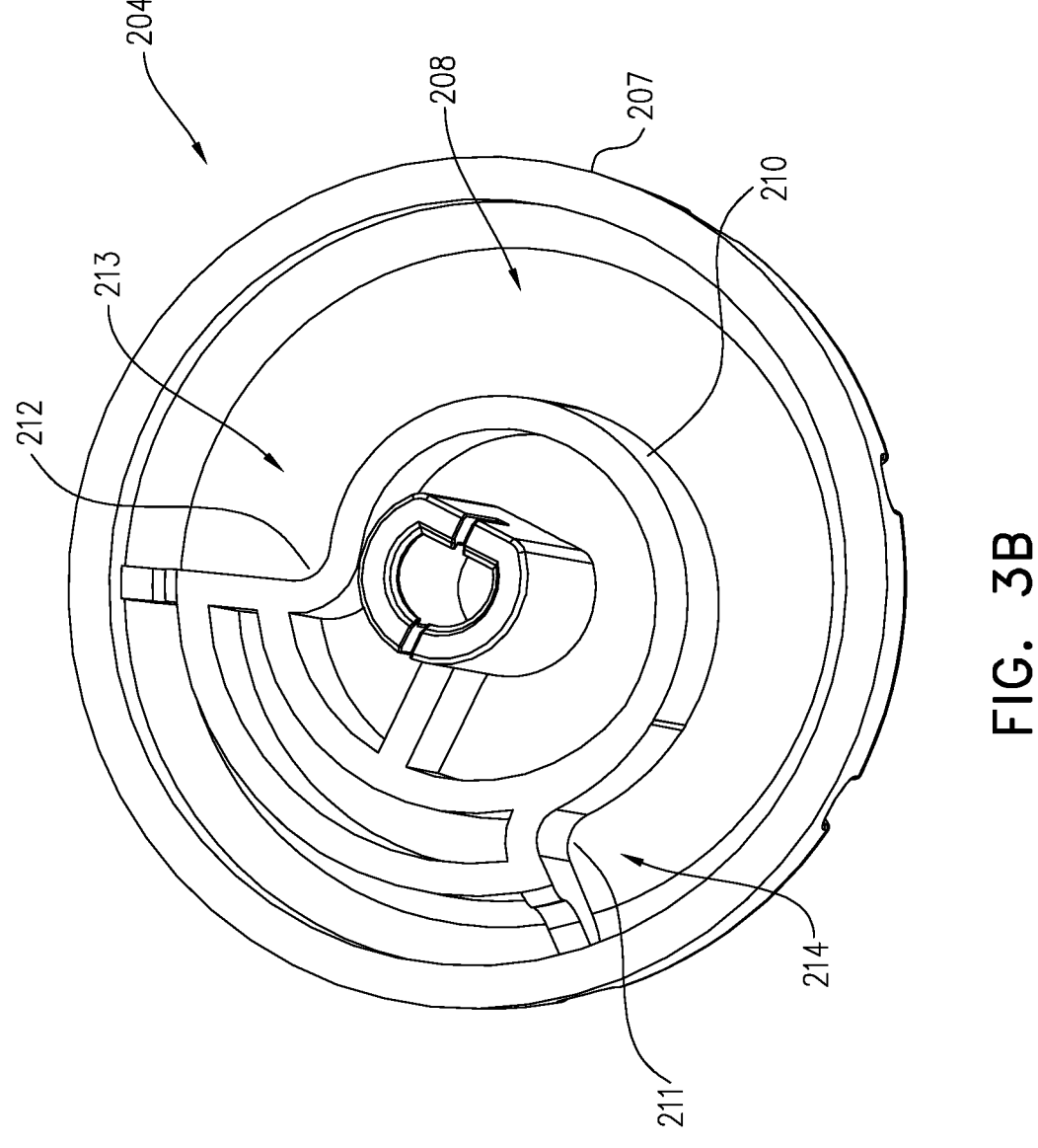
FIG. 3B illustrates an inner view of an actuator of a position adjustment mechanism according to certain aspects of the presently disclosed subject matter.
Figure 3C:
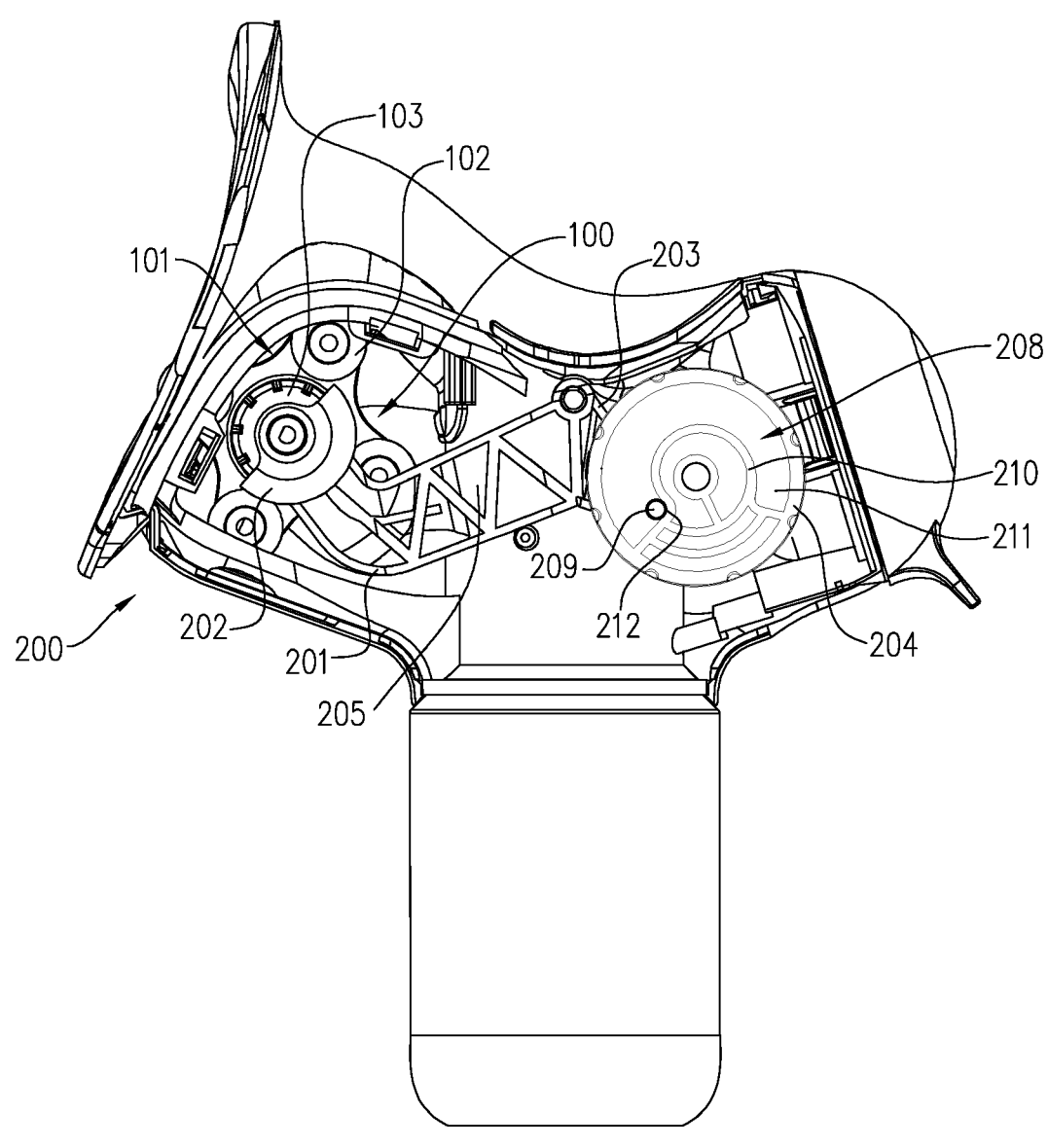
FIG. 3C illustrates a cross-section of FIG. 3A depicting a stimulating mechanism in its initial position.
Figure 3D:
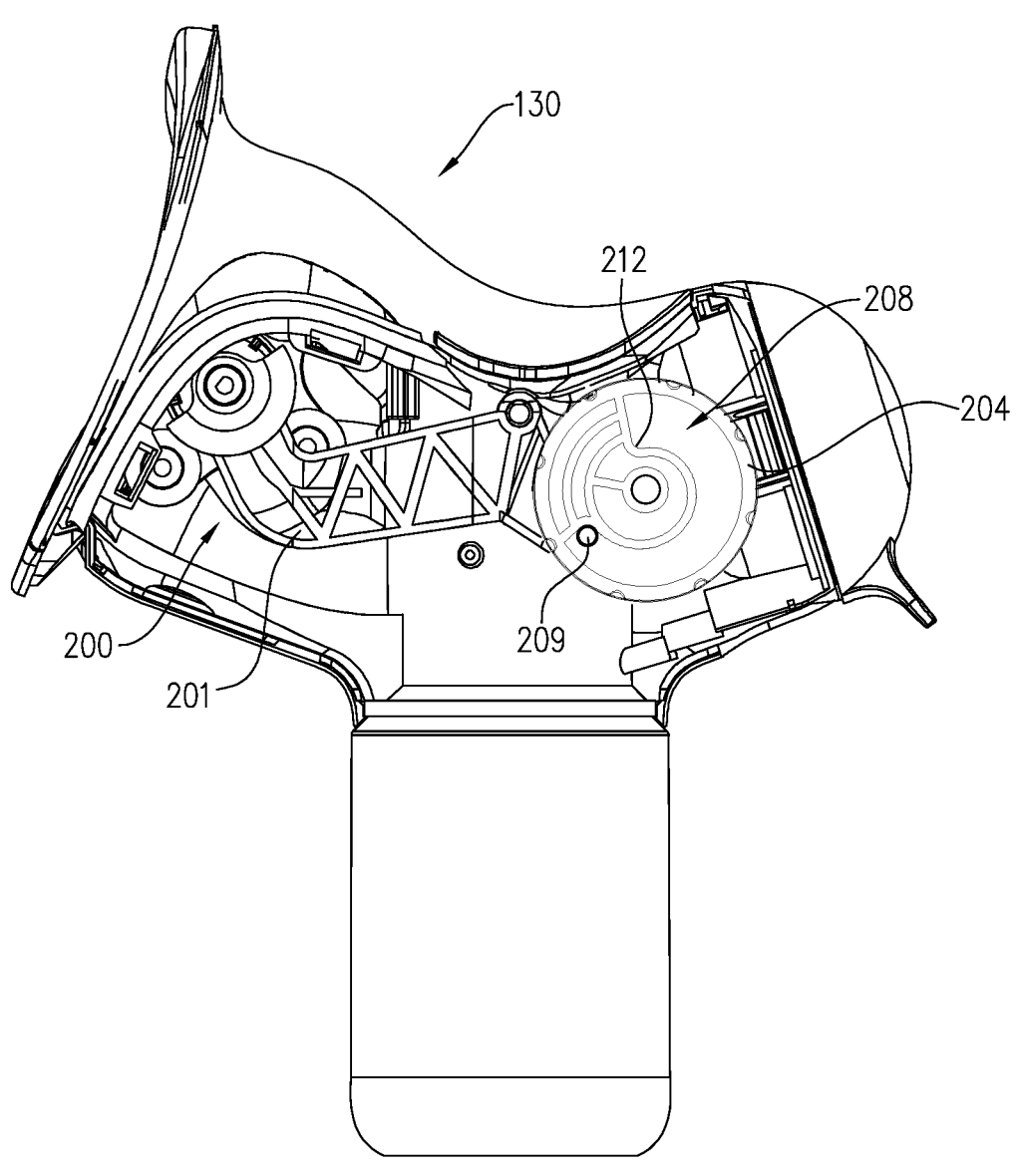
FIG. 3D illustrates a cross section of FIG. 3A depicting the stimulating mechanism in its final position.

The position adjustment mechanism 200 is configured to move the stimulating mechanism 100 between an initial position, as shown in FIG. 3C, at which the stimulating mechanism 100 causes the flexible portion 131A to have a first shape at least prior to operation of the stimulating mechanism 100, and a final position, as shown in FIG. 3D, at which the stimulating mechanism 100 causes the flexible portion 131A to have a second shape different from the first shape at least prior to operation of the stimulating mechanism 100. In some examples, at the initial position, the stimulating mechanism 100 causes a first tension in the flexible portion 131A and at the final position, the stimulating mechanism 100 causes a second tension, greater than the first tension, in the flexible portion 131A. In some examples, the first tension can be zero at least when the stimulating mechanism 100 is not being operated.

The position adjustment mechanism 200 is configured to move the stimulating mechanism from the initial position to the final position thereof at least partially in a direction D1 extending along a height of the user.

In some examples, the position adjustment mechanism can be configured to move the stimulating mechanism in an arcuate path.

As shown in FIGS. 3A-3D, the lever member comprises a lever first portion 202 articulated to the stimulating mechanism 100 and a lever second portion 203. The lever member 201 is configured to be pivoted in response to actuation of the lever second portion 203. In some examples, the lever second portion can be actuated by the user directly or indirectly holding the lever second portion 203, such as in the example described herein below with reference to FIG. 3E.

In the illustrated examples, the position adjustment mechanism 200 comprises an actuator 204 articulated to the lever second portion 203, and configured to pivot the lever member 201.

The breast milk pump 10 comprises the proximal portion 12 configured to be positioned towards the breast, the distal portion 13 configured to be positioned away from the breast, and a main axis MA extending therebetween. As con be seen in FIGS. 3A, 3C, and 3D, the actuator 204 is positioned distant from the stimulating mechanism 100 at least in a direction D2 along the main axis MA. In some of the illustrated examples, the position adjustment mechanism 200 comprises two lever members, one on each side of the breast milk pump 10, and a respective actuator 204 and 204' for each of the two lever members. The user can use any one of the actuators as per the convenience. The two lever members can be connected to each other such that actuating one of them causes the other one to follow the same path. The actuator 204 is configured to move the lever second portion 203. The movement of the second lever portion 203 causes the lever first portion 202 to pivot about the lever pivot axis LPA.

The lever member 201 comprises a lever first arm 205 extending between the lever first portion 202 and the lever pivot axis LPA, and a lever second arm 206 extending between the lever pivot axis LPA and the lever second portion 203. In the illustrated examples, the lever first arm 205 is longer than the lever second arm 206.

The position adjustment mechanism 200 is configured for a coarse adjustment of the position of the stimulating mechanism 100 and for a fine adjustment of the position of the stimulating mechanism 100.

The actuator 204 comprises a rotatable wheel 207. The position adjustment mechanism 200 is configured to convert said rotation of the wheel 207 into said movement of the stimulating mechanism 100 articulated to the lever first portion 202. In other examples, the actuator can comprise a linearly moveable element configured to move the lever second portion.

The actuator 204 and the lever second portion 203 constitute a part of a cam follower arrangement. The actuator 204 can comprise a cam 208 and the second lever portion 203 is articulated to the cam 208 via a follower 209. The follower 209 can be a separate member or can be a part of the lever second portion 203. The cam 208 comprises a spiral path 210 extending between a radially outermost end 211 and a radially innermost end 212 thereof. The follower 209 is biased to retain the spiral path 210 when the cam 208 is rotated, thereby following the variation in radius of the spiral path 210. When the follower 209 is at the radially innermost end 212, the stimulating mechanism 100 is at the initial position as shown in FIG. 3C, and when the follower

209 is at the radially outermost end 211, the stimulating mechanism 100 is at the final position as shown in FIG. 3D.

The spiral path 210 comprises an initial portion 213 including the radially innermost end 212 and a terminating portion 214 including the radially outermost end 211, and a curvature of the spiral path 210 is greater at the initial portion 213 than a curvature of the spiral path 210 at the terminating portion 214. When the follower 209 is at the initial portion 213, the position adjustment mechanism 200 is configured for a coarse adjustment of the position of the stimulating mechanism 100, and when the follower is at the final portion 214, the position adjustment mechanism 200 is configured for a fine adjustment of the position of the stimulating mechanism 100.

The cam 208 is configured to lock the follower 209 at one or more locations between the radially outermost end 211 and the radially innermost end 212. The cam 208 is configured to prevent a movement of the follower 209 by the lever member 201, for example by a force applied at the stimulating mechanism 100. The slope of the spiral path 210 is so configured that the follower 209 can be moved only by the rotation of the cam 208. When the cam 208 is not rotated, the follower 209 retains its location and does not move by a force exerted by the stimulating mechanism 100 via the lever member 201.

Figure 3E:
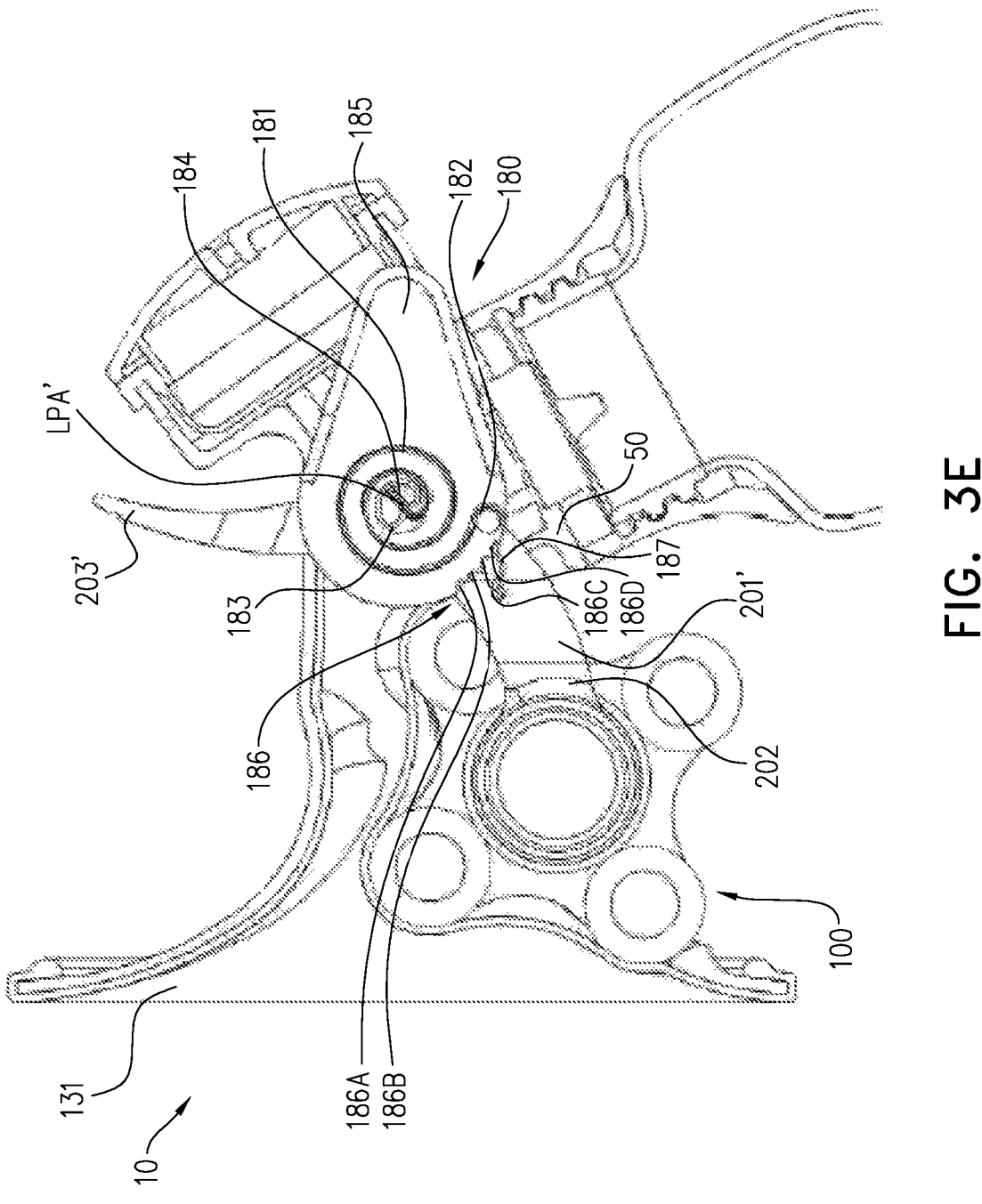
FIG. 3E illustrates a cross-sectional view of the breast milk pump comprising a position adjustment mechanism according to a particular embodiment of the presently disclosed subject matter.
Figure 4A:
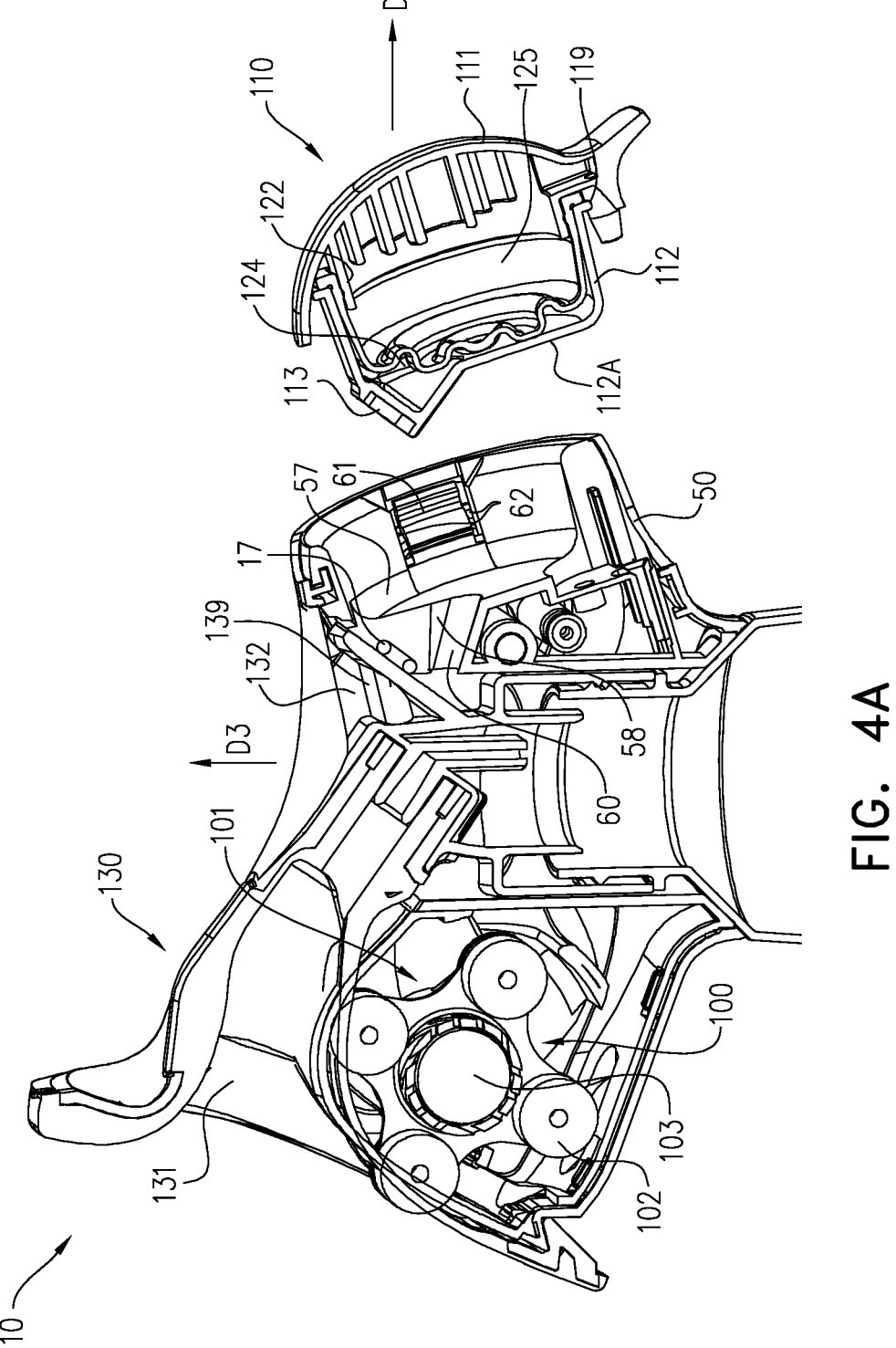
FIG. 4A illustrates a cross-section of a breast milk pump according to certain aspects of the presently disclosed subject matter with its vacuum assembly removed therefrom.
Figure 4B:
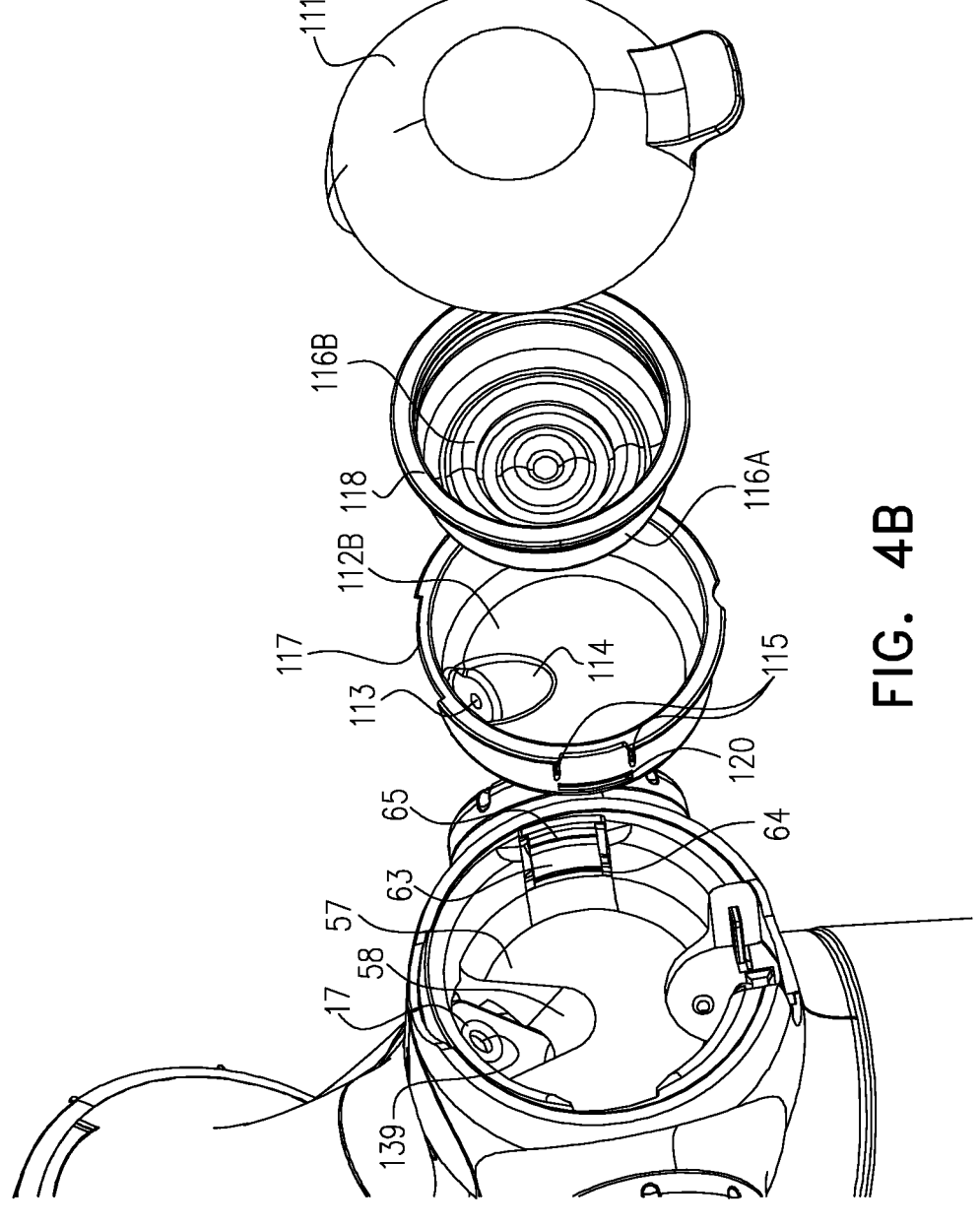
FIG. 4B illustrates a rear perspective partial exploded view of the breast milk pump illustrated in FIG. 4A.
Figure 4C:
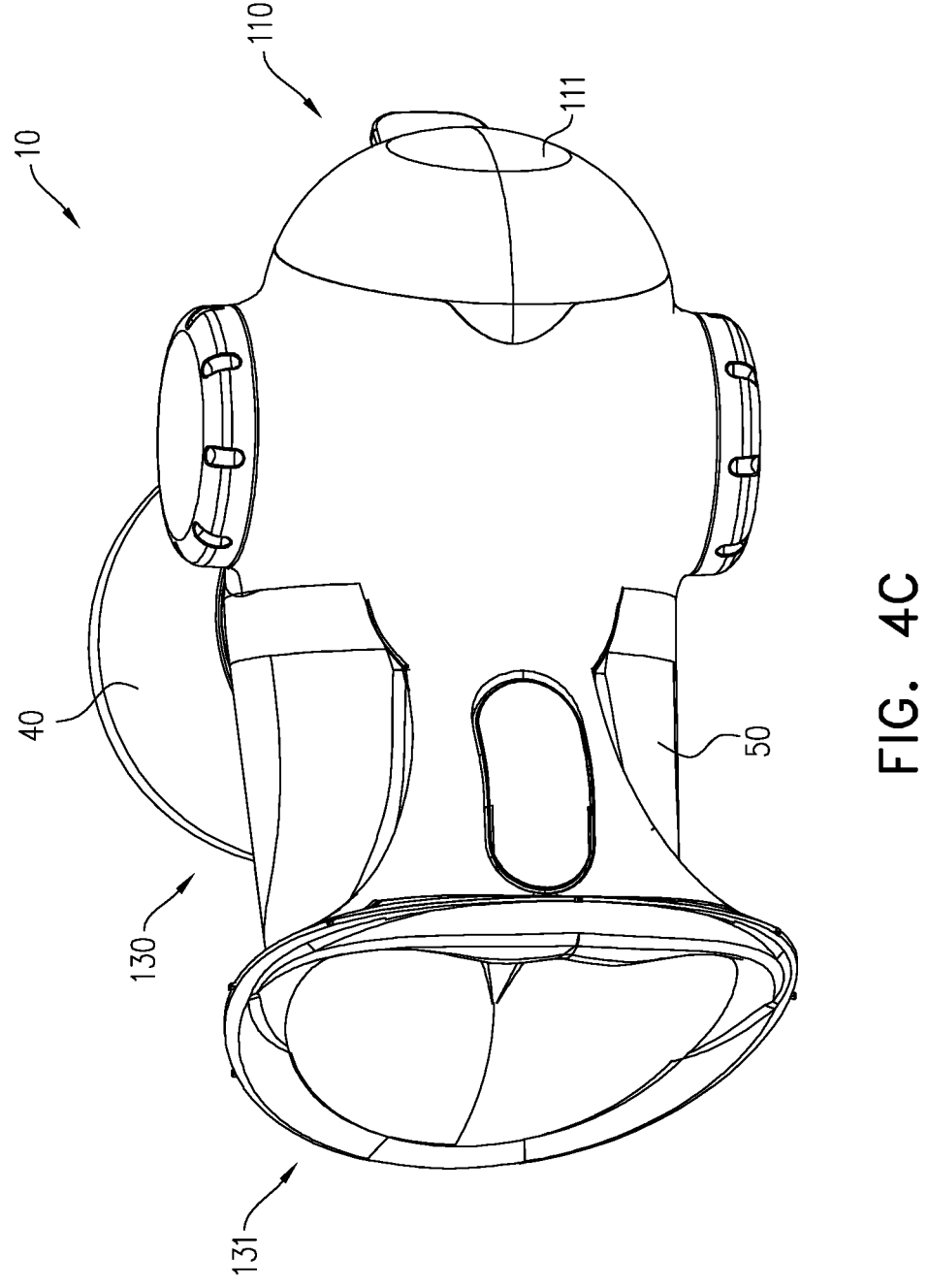
FIG. 4C illustrates a top perspective view of the breast milk pump illustrated in FIG. 4A.
Figure 4D:
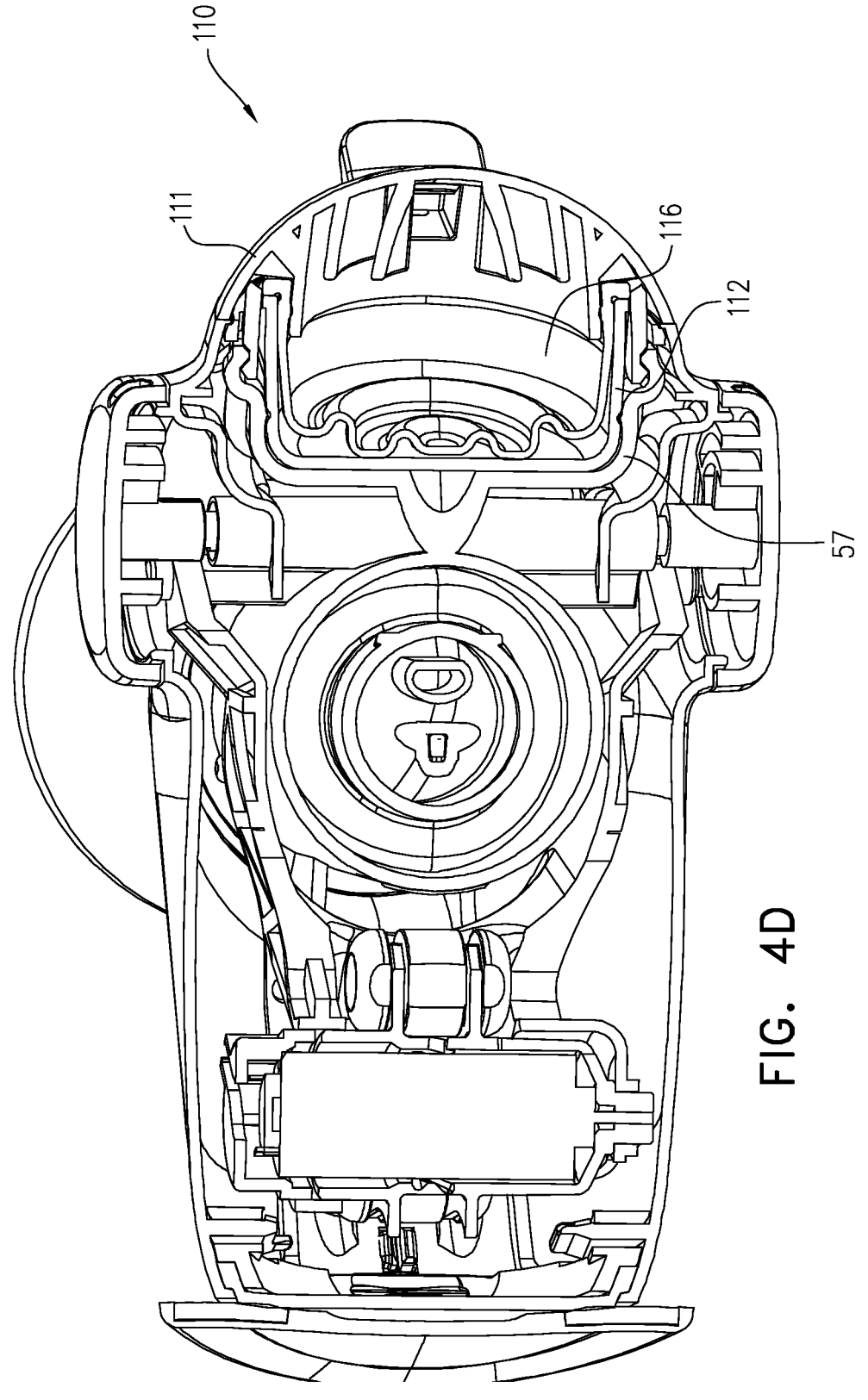
FIG. 4D illustrates a cross section of FIG. 4C.
Figure 4E:
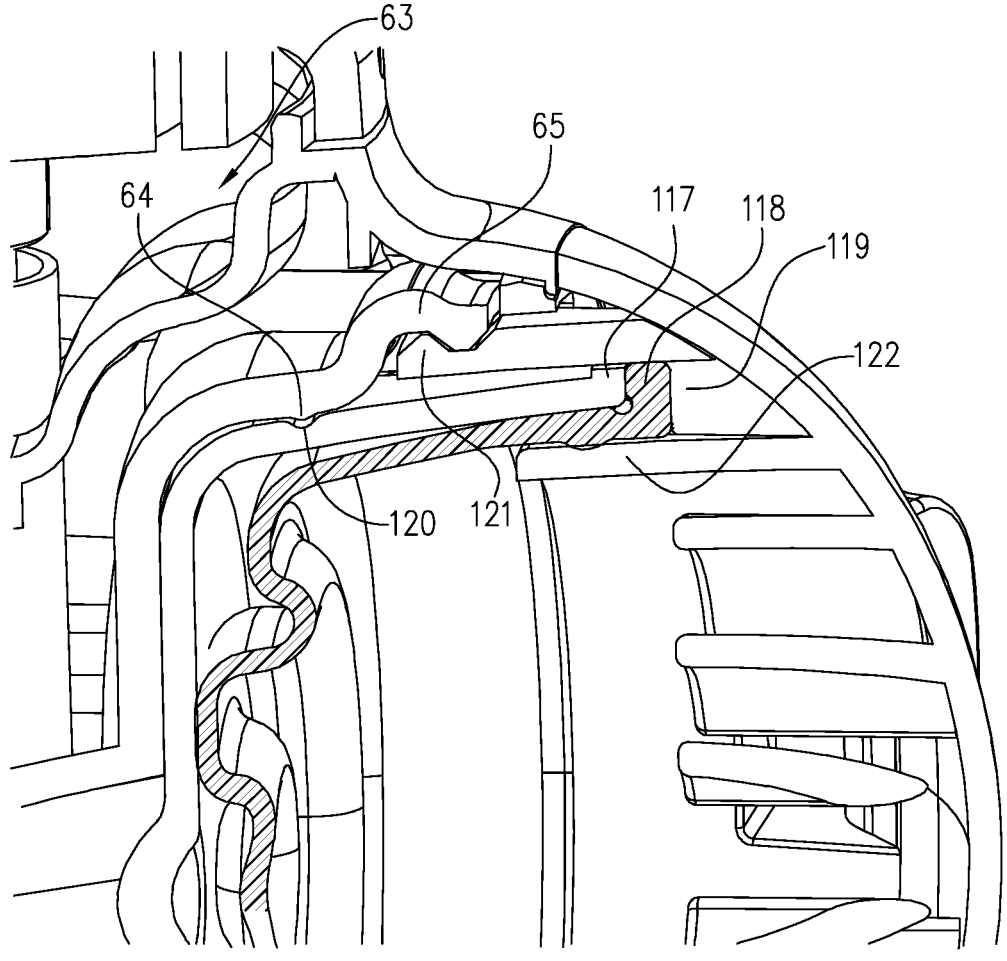
FIG. 4E illustrates an enlarged view of FIG. 4D.

FIG. 3E illustrates the breast milk pump 10 with the position adjustment mechanism 200' comprising a lever member 201' having a lever first portion 202' articulated to the stimulating mechanism 100, and a lever second portion 203', and pivotable about the lever pivot axis LPA'. The lever second portion 203' can be actuated by a user directly to adjust the position of the stimulating mechanism 100 with respect to the funnel 131. The breast milk pump 10, as illustrated in FIG. 3E, further comprises the body 50 and a stabilizing mechanism 180 configured for stabilizing the lever member 201' with respect to the body 50. The stabilizing mechanism 180 comprises a stabilizing biasing member 181 configured for controlling an extent of the stabilization of the lever member 201' with respect to the body 50. The stabilizing biasing member 181 is a spring having a first end 182 connected to a stabilizing cam 185 and a second end 183 connected to an axle 184 of the lever member 201'. Accordingly, the lever member 201' and the stimulating mechanism 100 are suspended with respect to the lever pivot axis LPA' and the stabilizing mechanism 180 which causes the stimulating mechanism 100 to be pushed upwardly. The tension of the spring 181 effects the extent of stabilizing of the lever member 201', i.e., more tense the spring 181 would be, the more stabilized the lever member 201' would be to the body 50, and consequently more stronger would the stabilizing mechanism 180 hold the stimulating mechanism 100 in its position. The stabilizing mechanism 180 comprises a controlling member configured for changing a tension of the stabilizing biasing member 181. The controlling member, in the illustrated example, is a stabilizing cam 185 configured to be rotated about the axle 184 of the lever member 201' to change the tension in the spring 181. The stabilizing cam 185 comprises a teeth member 186 configured to lock the stabilizing cam 185 in a plurality of positions corresponding to the teeth 186A, 186B, 186C, and 186D, each position defining a corresponding tension in the spring 181. In order to increase or decrease the tension in the spring 181, the stabilizing cam 185 can be rotated by the user, which in turn controls the extent of stabilizing of the lever member 201'. The stabilizing mechanism 180 further comprises a cam locking member 187 articulated to the body 50 (not shown in FIG. 3E) and configured to lock the stabilizing cam 185 in one of the plurality of positions. The cam locking member is articulated to the body at one end and the other end engages with the teeth member 186. The teeth to which the cam locking member 187 engages defines the position of the stabilizing cam 185.

FIGS. 4A-4E illustrate the breast milk pump 10 according to certain aspects of the presently disclosed subject matter. The milk extraction assembly 130 comprises a pressure interface passage 139 configured to allow passage of air therethrough. The breast milk pump 10 further comprises a vacuum chamber 112 comprising an orifice 113. The vacuum chamber 112 is configured to be detachably attachable to the breast milk pump 10 for establishing a fluid communication between the orifice 113 and the pressure interface passage 139.

The pressure interface passage 139 constitute a part of the air flow path 135 extending between the milk extraction assembly 130 and the vacuum assembly 110. The vacuum chamber 112 is configured to generate a negative pressure within the milk extraction assembly 130 through the orifice 113 and the pressure interface passage 139. The breast milk pump 10 further comprises a sealing member 17 (best seen in FIGS. 2B, 4A, and 4B) configured to seal the fluid communication between the pressure interface passage 139 and the orifice 113. The sealing member 17 is configured to prevent leakage of air at the connection of the orifice 113 and the pressure interface passage 139.

The milk extraction assembly 130 and the vacuum chamber 112 are configured to be detachably connectable to the body 50. The body 50 comprises the chamber supporting wall 57 configured to support the vacuum chamber 112 when the vacuum chamber 112 is attached to the breast milk pump 10. The orifice 113 and the pressure interface passage 139 are in fluid communication with each other through the chamber supporting wall opening 58 formed in the chamber supporting wall 57.

The chamber supporting wall 57 comprises a guiding element 60 configured to guide the vacuum chamber 112 into its designated position during attachment thereof to the breast milk pump 10. The vacuum chamber 112 comprises a guidable element 114 configured to be guided by the guiding element 60 during attachment of the vacuum chamber 112 to the breast milk pump 10. The guiding element 60 is a depression formed in the chamber supporting wall 57 and the guidable element 114 is a projection formed in the vacuum chamber 112 configured to be received within the depression 60. In some examples, the guiding element can be a projection formed in the chamber supporting wall and the guidable element can be a depression formed in the vacuum chamber configured to receive therewithin the projection. The orifice 113 and the pressure interface passage 139 are configured to be in communication through the guiding element 60.

The chamber supporting wall 57 further comprises chamber locking means 61 (best seen in FIG. 4B) configured to detachably lock the vacuum chamber 112 when connected to the breast milk pump 10 thereby connecting the vacuum chamber 112 with the body 50. The vacuum chamber 112 is configured to be connected to the breast milk pump 10 and to be locked at the chamber locking means 61 simultaneously by a single action. The chamber locking means 61 also acts as an additional guiding element for the vacuum chamber 112 while the vacuum chamber 112 is being connected to the body 50. The chamber locking means comprises recesses 62 configured to guide and receive therewithin corresponding bulges 115 formed on the vacuum chamber 112.

The milk extraction assembly 130 is connectable to and/or detachable from the body 50 irrespective of whether the vacuum chamber 112 is connected to or detached from the body 50. The vacuum chamber 112 is connectable to and/or detachable from the body 50 irrespective of whether the milk extraction assembly 130 is connected to or detached from the body 50. The milk extraction assembly 130 is configured to be at least partially received within the body 50 and can be configured to be extracted in a first extraction direction D3, which in the illustrated example is along a height of the user. The vacuum chamber 112 is configured to be received at least partially within the body 50 and can be configured to be extracted in a second extraction direction D4, which in the illustrated example is perpendicular to the first extraction direction D3. The vacuum chamber 112 and the milk extraction assembly 130 are configured to be attached to each other at a particular angle with respect to each other such that a connecting interface between the two makes a particular angle with the first and second extraction directions, which in the illustrated example is 45 degrees, such that the milk extraction assembly and the vacuum chamber can be detached from the body independently of each other. In other examples, the angle between the first and the second extraction directions can be different than 90 degrees, and the connecting interface can be based on the same.

The vacuum chamber 112 constitutes a part of the vacuum assembly 110 comprising, in addition to the vacuum chamber 112, a membrane 116 configured to be removably articulated to the vacuum chamber 112, and the cap 111 configured to close the vacuum chamber 112 at least with the membrane 116 articulated thereto. The membrane 116 can be a diaphragm configured to deform when a pressure difference is created on two sides of the diaphragm. The vacuum chamber 112 comprises a chamber rim 117 and the membrane 116 can comprise a membrane rim 118 corresponding to the chamber rim 117 and configured to be positioned on the chamber rim 117. The cap 111 comprises a lip 119 and is configured to sealingly close the vacuum chamber 112 while sealing the membrane rim 118 between the lip 119 and the chamber rim 117. The connection of the chamber rim 117, the membrane rim 118, and the lip 119 is leakage proof, i.e., does not allow any leakage of air therefrom.

The cap 111 is configured to be removably locked to the chamber supporting wall 57. The cap 111 can be configured to be removably locked to the chamber supporting wall 57 via the at least one chamber locking means 61. The vacuum assembly 110 is configured to be connected to the body 50 while locking the vacuum chamber 112 and the cap 111 to the chamber locking means 61 simultaneously in a single action. The vacuum chamber 112 comprise a chamber locking portion 120 and the cap 111 comprises a cap locking portion 121, wherein the at least one chamber locking means 61 comprises a snap connector 63 configured to receive the chamber locking portion 120 and the cap locking portion 121. The snap connector 63 can comprise a first snapping portion 64 configured to engage with and to lock the chamber locking portion 120, and a second snapping portion 65 configured to engage with and to lock the cap locking portion 121. The cap 111 can be configured to be detached from the chamber supporting wall 57 together with the vacuum chamber 112. The cap 111 can be configured to be connected to the chamber supporting wall 57 independently of the vacuum chamber 112. When the cap 111 is extracted from the chamber supporting wall 57, the detachment of the cap 111 from the chamber supporting wall 57 causes detachment of the cap locking portion 121 from the second snapping portion 65, which in turn displaces the snap connector 63 and causes disengagement of the chamber locking portion 120 from the first snapping portion 64.

The cap 111 can further comprise a flange 122 configured to engage with the membrane 116, wherein the cap 111 is configured to tightly receive a portion 123 of the membrane 116 between the flange 122 and the vacuum chamber 112 when closed. The frictional association between the flange 122, the membrane 116, and the vacuum chamber 112 causes the vacuum chamber 112, the membrane 116, and the cap 111 to be extracted from the body together in a single action.

The vacuum chamber 112 has a chamber outer surface 112A configured to face the breast milk pump 10 and an opposite chamber inner surface 112B, and the membrane 116 can have a membrane first surface 116A configured to face the chamber inner surface 112B and an opposite membrane second surface 116B configured to face the cap 111. The vacuum chamber 112 can comprise a chamber first region 124 defined by the chamber inner surface 112B and the membrane first surface 116A, and a chamber second region 125 defined by the membrane second surface 116B and the cap 111. The chamber first region 124 is configured to be in fluid communication with the milk extraction assembly 130 through the orifice 113 and the pressure interface passage 139 when the vacuum chamber 112 is connected to the breast milk pump 10. The chamber second region 125 is configured to be fluidly connected, via the cap 111, to the pumping device 20 configured to generate a vacuum at the chamber second region 125. In response to the vacuum, the membrane 116 deforms towards the chamber second region 125 and generate a negative pressure in the chamber first region 124, and consequently in the milk extraction assembly 130 via the orifice 113 and the pressure interface passage 132.

Attention is now directed towards FIGS. 5A-5E illustrating a breast milk pump 10' according to certain aspects of the presently disclosed subject matter. The breast milk pump 10' may include one or more features similar to the features of breast milk pump 10 described herein according to certain aspects of the presently disclosed subject matter.

The breast milk pump 10' is a manually operable breast milk pump that can include the stimulating mechanism, the vacuum assembly, the body, the milk extraction assembly, etc. similar to those of the breast milk pump 10, but instead operable manually rather than electrically as in the breast milk pump 10. The breast milk pump 10' comprises a milk extraction assembly 130' comprising a funnel 131' configured to engage a breast of a user. The funnel 131' comprises a flexible portion 131'A. The breast milk pump 10' comprises a stimulating mechanism 100' and a vacuum assembly 110'. The stimulating mechanism 100' is configured to manipulate the flexible portion 131'A. The vacuum assembly 110' is configured to generate a negative air pressure within the funnel 131'.

In some examples, stimulating mechanism 100', the vacuum assembly 110', and the milk extraction assembly 130' include one or more features similar to the stimulating mechanism 100, the milk extraction assembly 130, and the vacuum assembly 110 described herein according to certain aspects of the presently disclosed subject matter. For instance, the flexible portion 131'A of the funnel 131' may be of a substantially similar configuration as the flexible portion 131A of the funnel 131 as shown in FIG. 2A-2C.

Figure 5A:
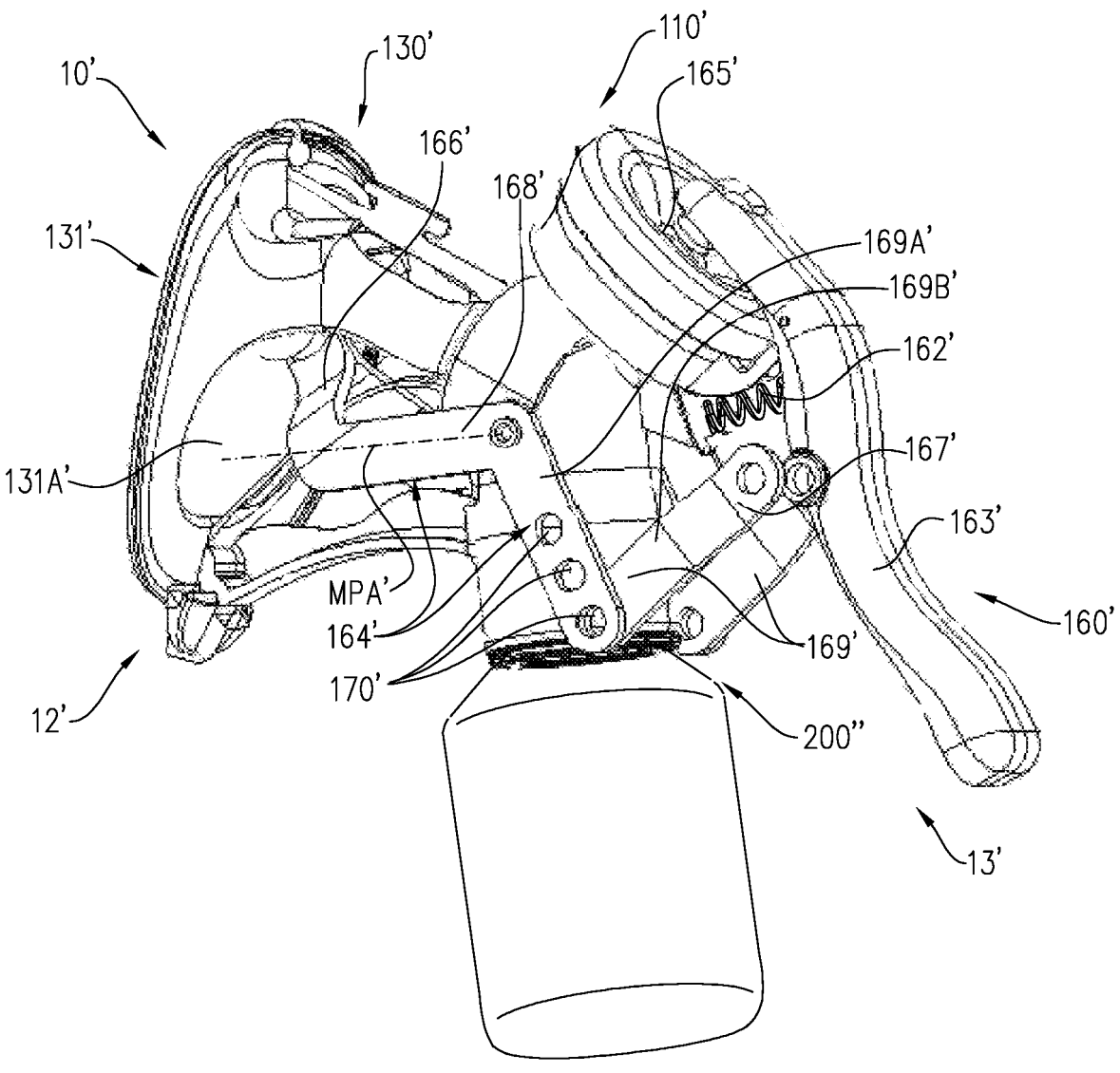
FIG. 5A illustrates a rear perspective view of a breast milk pump according to certain aspects of the presently disclosed subject matter.

As can be seen in FIG. 5A, the breast milk pump 10' comprises a manually operable trigger mechanism 160' articulated to the stimulating mechanism 100' and to the vacuum assembly 110'. The manually operable trigger mechanism 160' is configured to simultaneously operate the stimulating mechanism 100' and the vacuum assembly 110'.

Figure 5B:
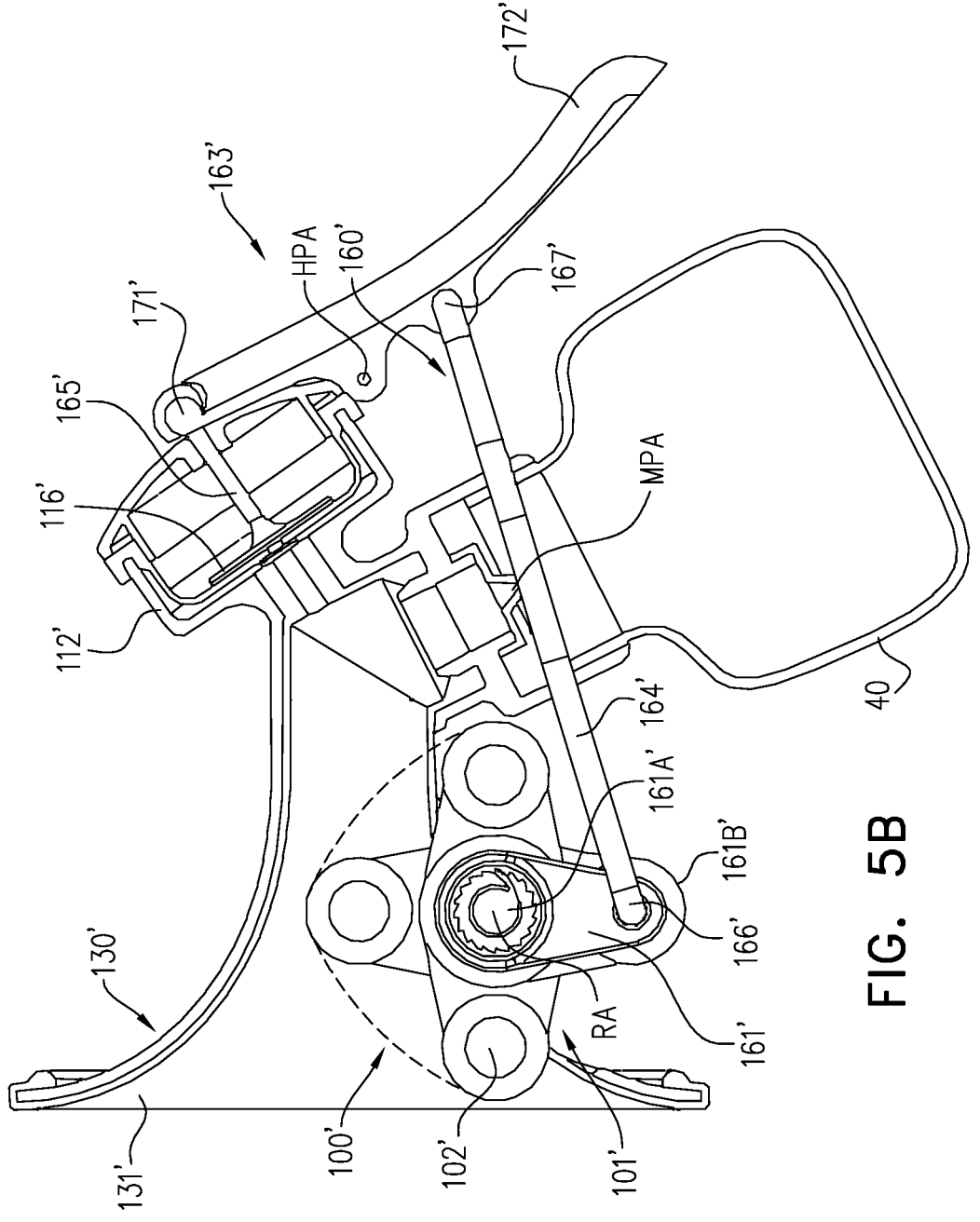
FIG. 5B illustrates a cross-sectional view of a breast milk pump according to a particular embodiment of the presently disclosed subject matter.

FIG. 5B illustrates the breast milk pump 10', according to a particular embodiment, comprising the stimulating mechanism 100' including a rotational assembly 101' comprising at least one roller 102' configured to rotate about a roller axis RA passing through a plane of the paper to stimulate the flexible portion 131'A. In the example illustrated in FIG. 5B, the trigger mechanism 160' is configured to cause the rotation of the roller 102' via ratchet mechanism 161'. The ratchet mechanism having a first ratchet end 161A' connected to the rotational assembly 101' and a second ratchet end 161B' connected to the trigger mechanism 160'. In other examples, the stimulating mechanism 100' can comprise stationary members configured to move up and down by the trigger mechanism 160', for example in the examples illustrated in FIGS. 5A and 5C-5E.

The stimulating mechanism 100' has an operative state at which the stimulating mechanism 100' manipulates the flexible portion 131'A and an inoperative state, wherein the vacuum assembly 110' can have a negative pressure state at which the vacuum assembly 110' generates the negative air pressure within the funnel and a normal pressure state, wherein the trigger mechanism 160' has a triggered state associated with the final position and the negative pressure state, and a resting state associated with the initial position and the normal pressure state.

The trigger mechanism 160' is configured to displace the stimulating mechanism 100' into its operative state and the vacuum assembly 110' into its negative pressure state when the trigger mechanism is 160' displaced into its triggered state.

The trigger mechanism 160' is configured to displace from the resting state to the triggered state upon application of a force by a user. The trigger mechanism 160' can be configured to return to its resting state upon removal of said force. The trigger mechanism 160' comprises a biasing member 162' configured to displace the trigger mechanism 160' into its resting state upon removal of said force. In the illustrated example, the biasing member is a spring.

The trigger mechanism 160' comprises a handle 163', a stimulation trigger member 164' connecting the handle 163' and the stimulating mechanism 100', and a vacuum trigger connector 165' connecting the handle 163' and the vacuum assembly 110'.

The breast milk pump 10' can comprise a proximal portion 12' configured to be positioned towards the breast and a distal portion 13' configured to be positioned away from the breast. The stimulating mechanism 100' is positioned at the proximal portion 12', and the handle 163' and the vacuum assembly 110' are positioned at the distal portion 13'.

The stimulation trigger member 164' comprises a member first end 166' articulated to the stimulating mechanism 100' and a member second end 167' articulated to the handle 163'. The stimulation trigger member 164' is pivotable by the handle 163' about a member pivot axis MPA' located between the member first end 166' and the member second end 167', so as to operate the stimulating mechanism 100' articulated to the member first end 166'. The handle 163' is configured to pivot the stimulation trigger member 164' to displace the stimulating mechanism 100' from its inoperative state to its operative state.

The breast milk pump 10' further comprises a position adjustment mechanism 200" configured to adjust a position of the stimulating mechanism 100' with respect to the funnel 131'. The position adjustment mechanism 200'' includes one or more features similar to the features of position adjustment mechanism 200 described above with respect to FIGS. 3A-3D.

The stimulation trigger member 164' comprises a member first arm 168' and a member second arm 169'. The member first arm 168' extends between the member pivot axis MPA' and the member first end 166'. The member second arm 169' extends between the member pivot axis MPA' and the member second end 167'. The member second arm 169' comprises an arm first portion 169A' extending from the member pivot axis MPA' and an arm second portion 169B' extending from the member second end 167'.

In some examples, at least one of the arm first portion 169A' and the arm second portion 169B' comprises a plurality of connecting points 170' positioned along a length thereof, the arm first portion 169A' and the arm second portion 169B' being connectable to each other at any one of the plurality of connecting points 170'. In some examples, the connecting points 170' constitute at least a part of a position adjustment mechanism 200'', according to a specific example of the presently disclosed subject matter, whereas the connection point at which the arm first portion 169A' and the arm second portion 169B' are connected, effect the position of the stimulating mechanism 100' with respect to the funnel 131'.

Figure 5C:
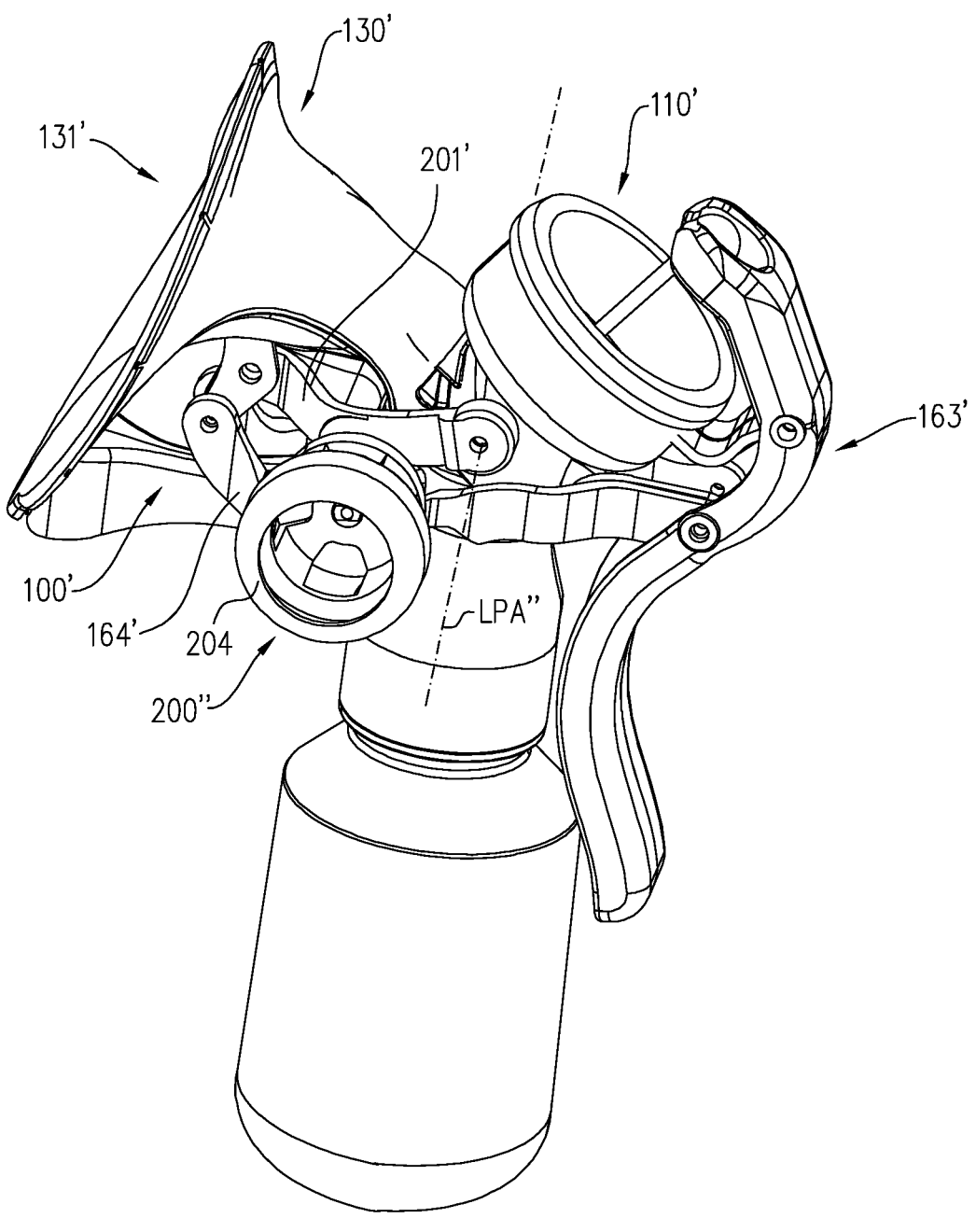
FIG. 5C illustrates a side perspective view a breast milk pump according to another particular embodiment of the presently disclosed subject matter.
Figure 5D:
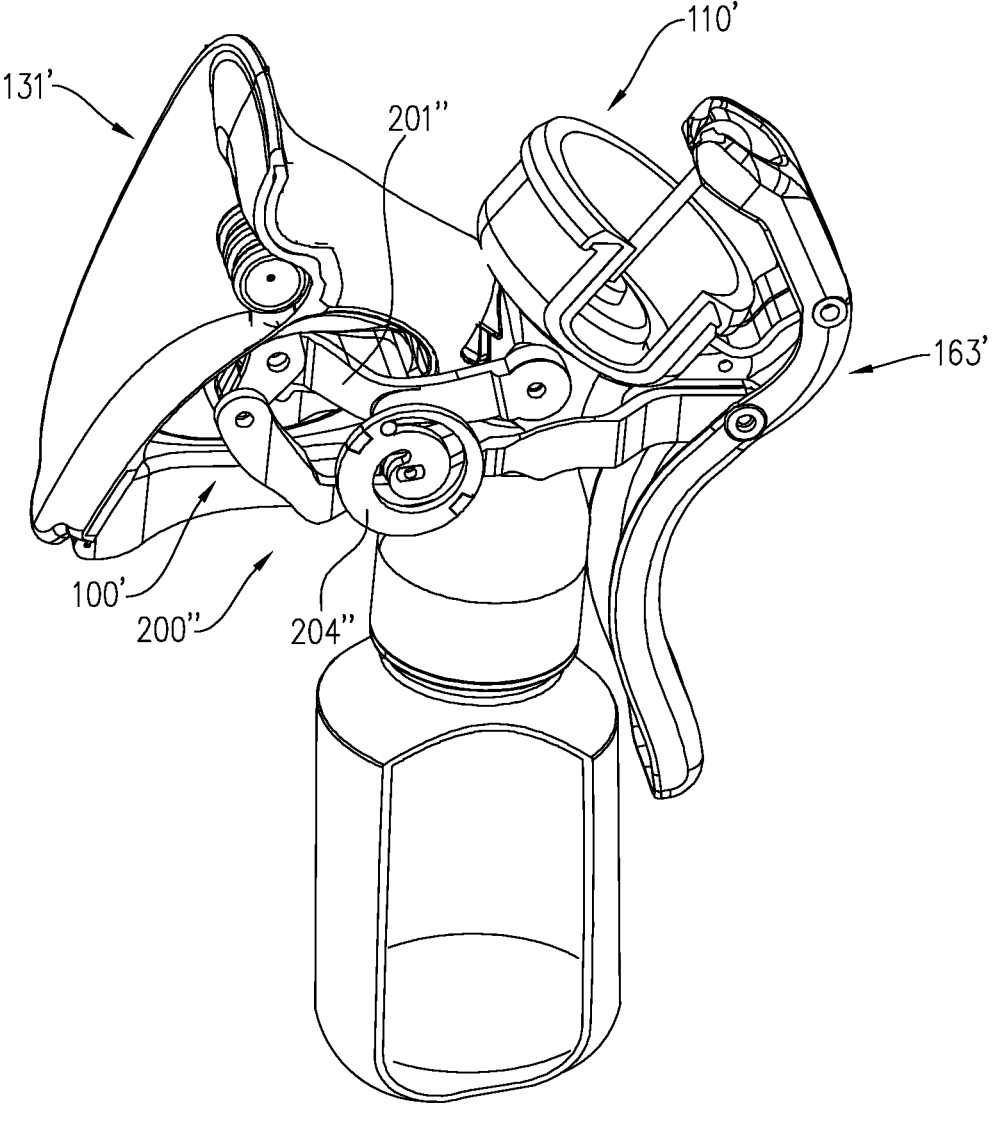
FIG. 5D illustrates a cross section of FIG. 5C.
Figure 5E:
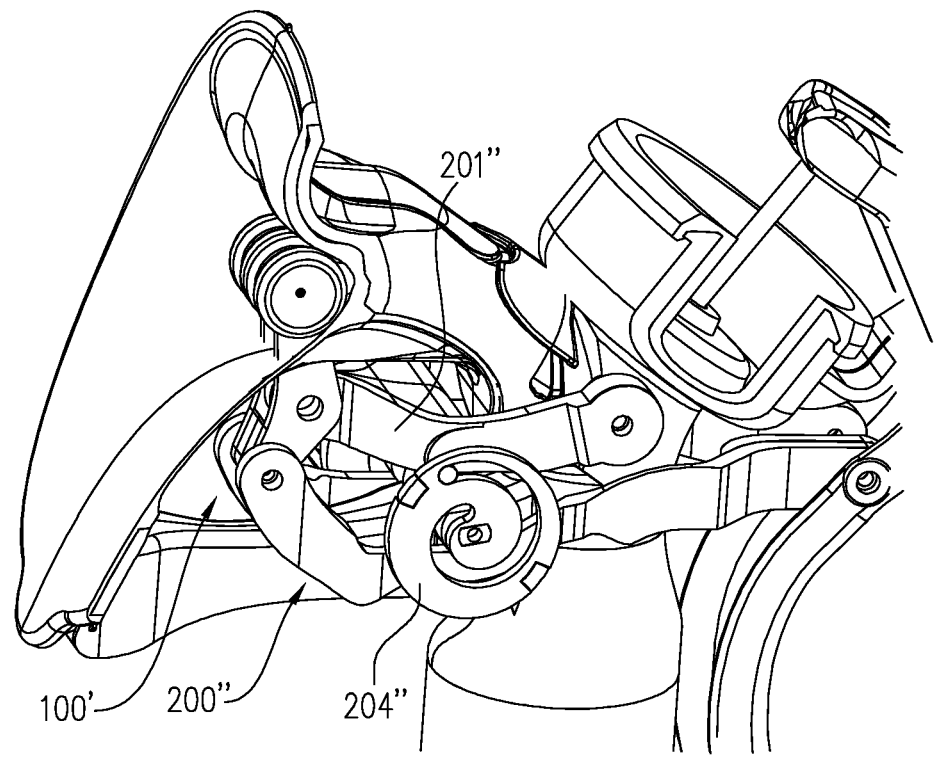
FIG. 5E illustrates an enlarged view of FIG. 5D.

The position adjustment mechanism 200'', in the example illustrated in FIGS. 5C-5E, comprises an actuator 204'' and at least one lever member 201''. The lever member 201'' includes a lever first portion 202'' articulated to the stimulating mechanism 100' and a lever second portion 203'' articulated to the actuator 204'', the lever member 201'' being pivotable by the actuator 204'' about a lever pivot axis LPA'', thereby moving the stimulating mechanism 100' articulated to the lever first portion 202''. The position adjustment mechanism 200'' is configured to move the stimulating mechanism 100' between an initial position at which the stimulating mechanism 100' causes the flexible portion 131'A to have a first shape at least prior to operation of the stimulating mechanism 100', and a final position at which the stimulating mechanism 100' causes the flexible portion 131'A to have a second shape different from the first shape at least prior to operation of the stimulating mechanism 100'. The position adjustment mechanism 200'', the lever member 201'', the actuator 204'' and their parts can correspond to the position adjustment mechanism 200, the lever member 201, the actuator 204, and parts thereof and can be configured to operate in a corresponding manner.

The vacuum assembly 110' comprises a vacuum chamber 112' having a chamber inner surface 112B', and a membrane 116' configured to be sealingly articulated to the vacuum chamber 112'. The membrane 116' comprises a membrane first surface 116A' configured to face the chamber inner surface 112B' and an opposite membrane second surface 116B'. The vacuum chamber 112' comprises a chamber first region 124' defined by the chamber inner surface 112B' and the membrane first surface 116A', the membrane being configured to be deformed by the trigger mechanism 160' away from the chamber inner surface 112B', thereby generating the negative pressure in the chamber first region 124' and consequently in the milk extraction assembly 130'.

The handle 163' is connected to the membrane second surface 116B' and is configured to pull the membrane second surface 116B' so as to deform the membrane 116' away from the chamber inner surface 112B'. The membrane 116' is configured to remain sealingly articulated to the vacuum chamber 112' when pulled by the handle 163'.

The trigger mechanism 160' can be configured to return to its resting state by virtue of the membrane 116' returning to its original shape upon removal of said force. The membrane 116' is configured to be elastically deformable, and the elasticity of the membrane 116' tends to displace the handle 163' into its initial state.

The handle 163' can comprise a handle first portion 171' articulated to the vacuum assembly 110' via the vacuum trigger connector 165' and a handle second portion 172' articulated to the stimulating mechanism 100' via the stimulation trigger member 164'. The handle 163' is pivotable about a handle pivot axis HPA located between the handle first portion 171' and the handle second portion 172'. The handle 163' is pivotable about the handle pivot axis HPA to displace the trigger mechanism 160' between the resting state and the triggered state.

Figure 6A:
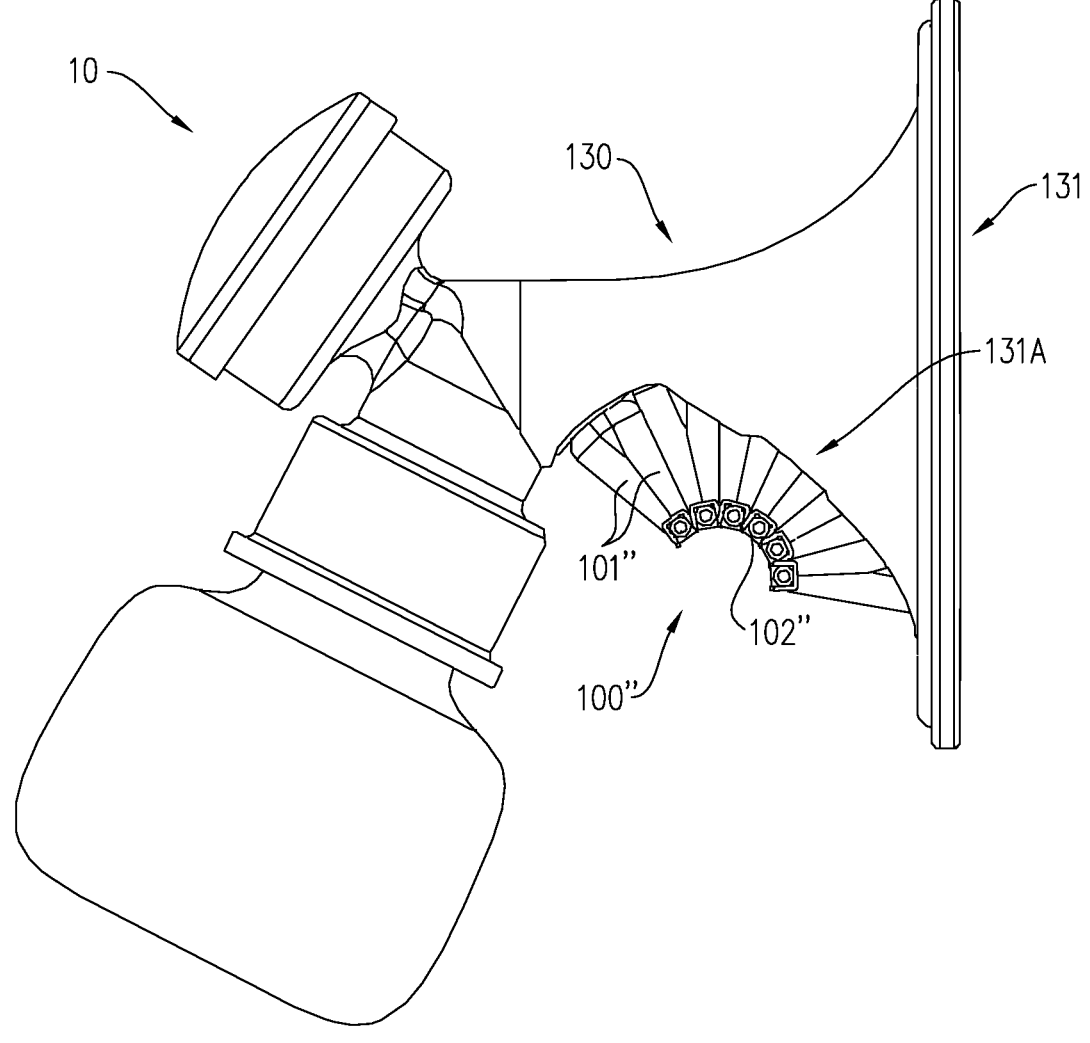
FIG. 6A illustrates a side view of a breast milk pump according to certain aspects of the presently disclosed subject matter.
Figure 6B:
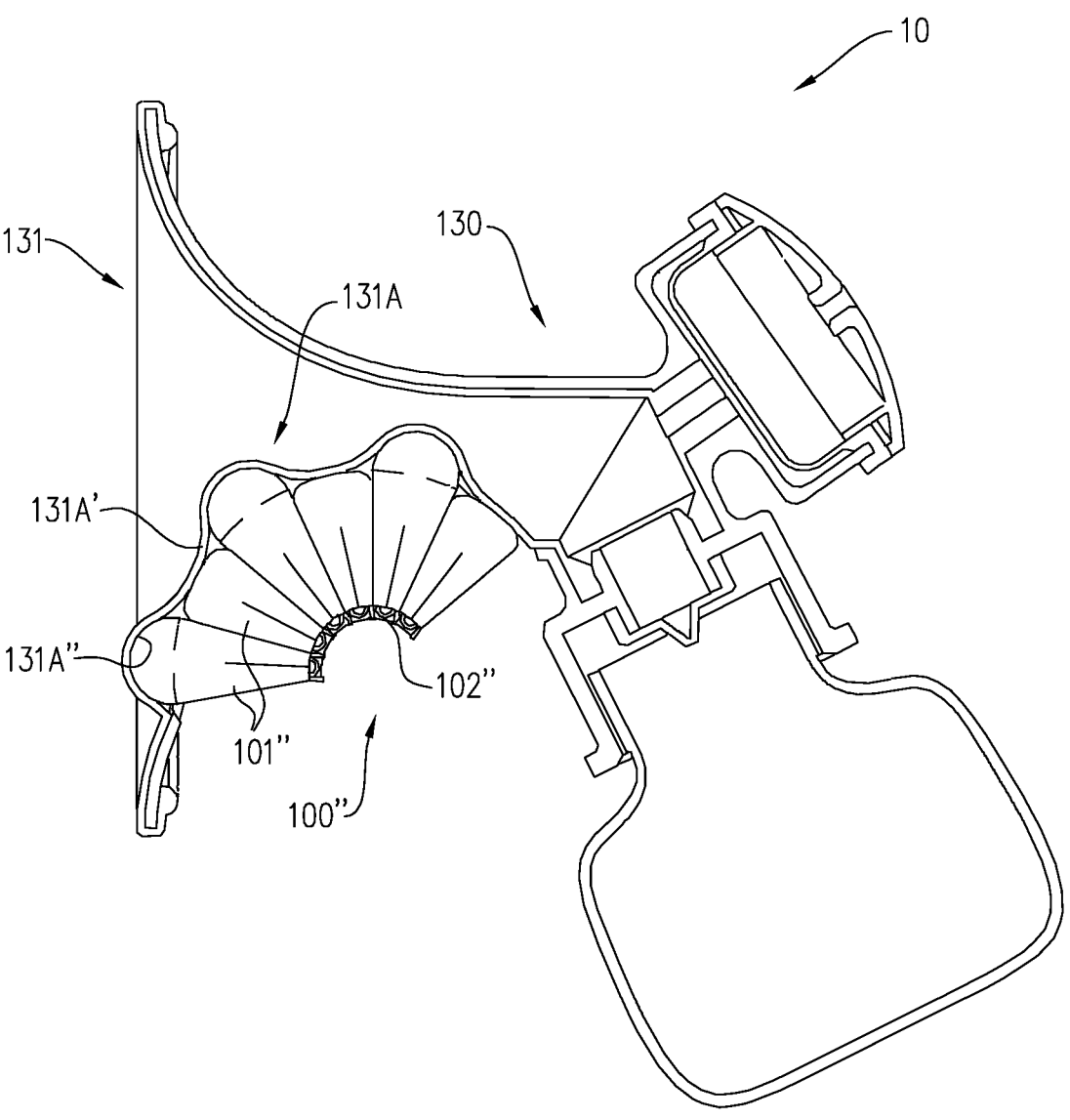
FIG. 6B illustrates a cross-sectional view of the breast milk pump illustrated in FIG. 6A.
Figure 6C:
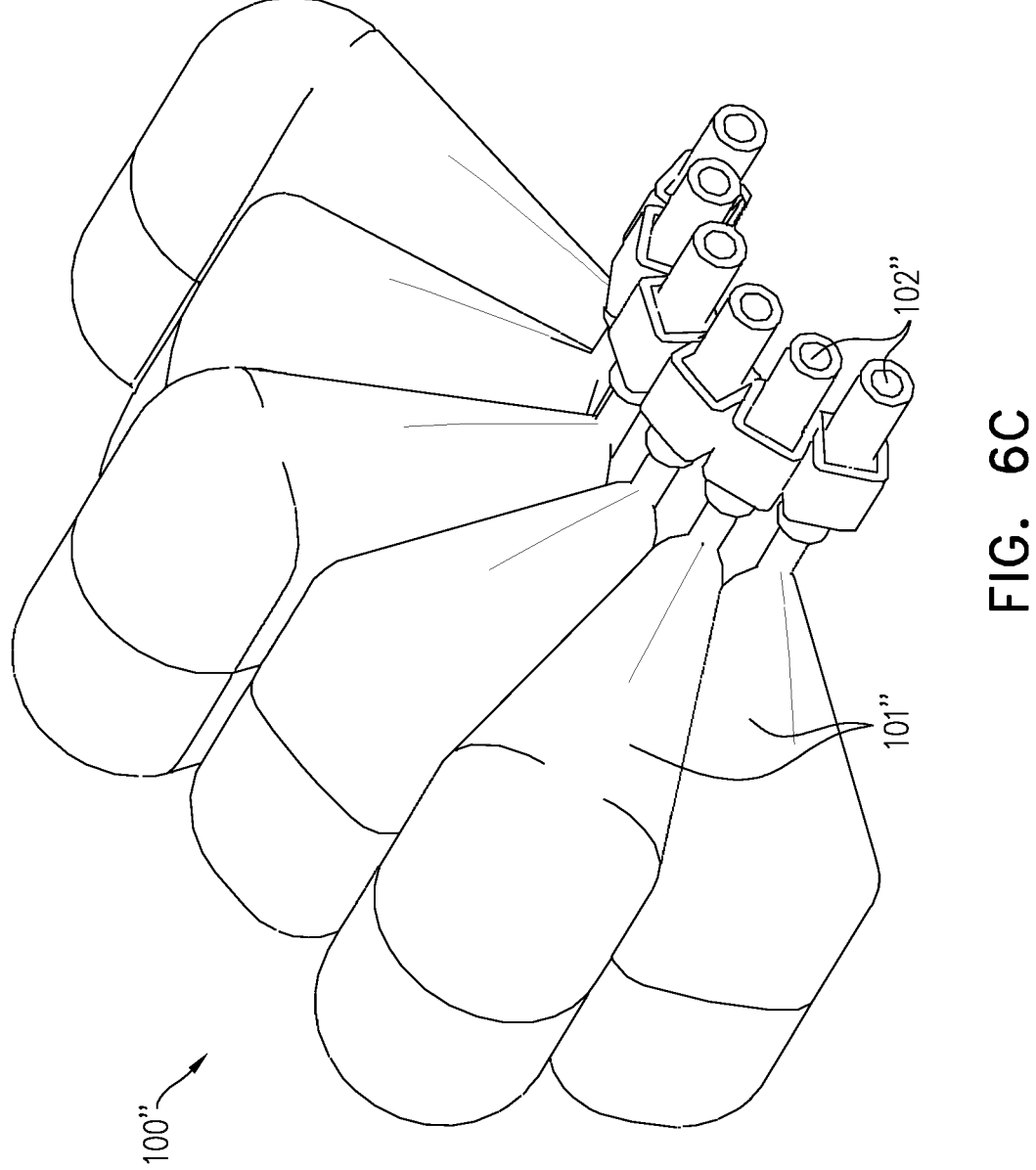
FIG. 6C illustrates a stimulating mechanism of the breast milk pump illustrated in FIG. 6A.

Attention is now directed to FIGS. 6A-6C, which illustrate a breast milk pump 10 comprising a stimulating mechanism 100'' according to a particular example of the presently disclosed subject matter. The breast milk pump 10 can be or can include one or more features of the breast milk pumps described herein with respect to various aspects, while comprising the stimulating mechanism 100'' as detailed herein below.

The breastmilk pump 10 comprises the milk extraction assembly 130 comprising the funnel 131 configured to engage a breast of a user. The funnel 131 comprises the flexible portion 131A. The breastmilk pump 10 comprises a stimulating mechanism 100'' configured to manipulate the flexible portion 131A. The stimulating mechanism 100'' comprises selectively inflatable and deflatable elements 101'' configured to manipulate the flexible portion upon being inflated and deflated.

The flexible portion 131A comprises the flexible portion inner surface 131A' for facing the breast and the opposite flexible portion outer surface 131A'' for facing the stimulating mechanism 100''. The stimulating mechanism 100'' is configured to manipulate the flexible portion outer surface 131A''.

The inflatable and deflatable elements 101'' are configured to cause the flexible portion 131A to have a first shape when deflated and a second shape when inflated. In some examples, in the first shape, the flexible portion 131A has a first tension therewithin and in the second shape, the flexible portion 131A has a second tension, greater than the first tension, therewithin. In some examples, the first shape is an original shape of the flexible portion 131A, i.e., when deflated, the stimulating mechanism 100'' may not deform the flexible portion 131A at all.

The stimulating mechanism 100'' comprises a fluid port 102'' configured to be connected to a fluid pump (not shown). In some examples, the fluid pump can be same as or configured as a part of the pumping device 20. The fluid port 102'' is configured to establish a fluid interface between the fluid pump and each one of the inflatable and deflatable elements 101''. The inflatable and deflatable elements 101'' are configured to be inflated and deflated by a fluid pumped by the fluid pump via the fluid port 102''.

The inflatable and deflatable elements 101'' are configured to be inflated and deflated according to a predetermined pattern that can be implemented by a controller of the fluid pump or of the breast milk pump 10.

Figure 7A:
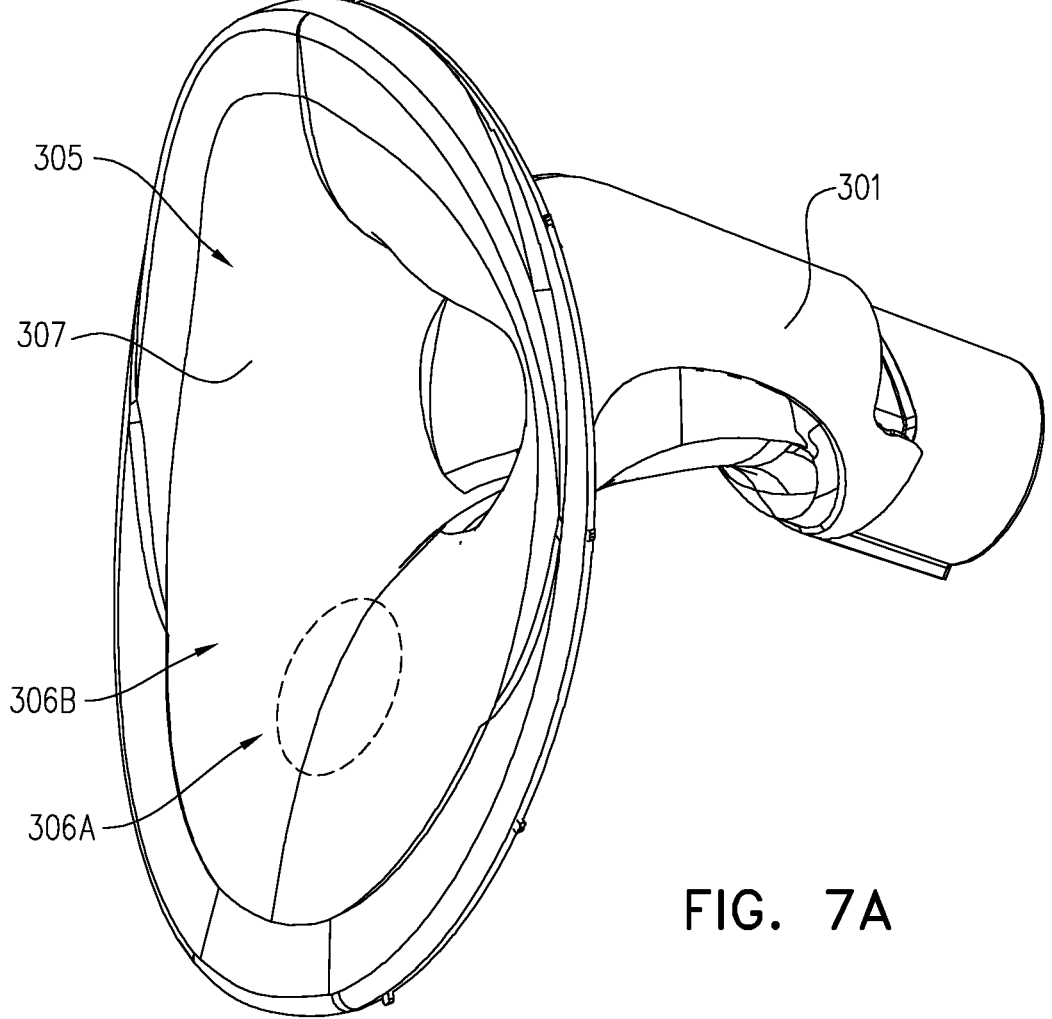
FIG. 7A illustrates a side perspective view of a funnel according to certain aspects of the presently disclosed subject matter.
Figure 7B:
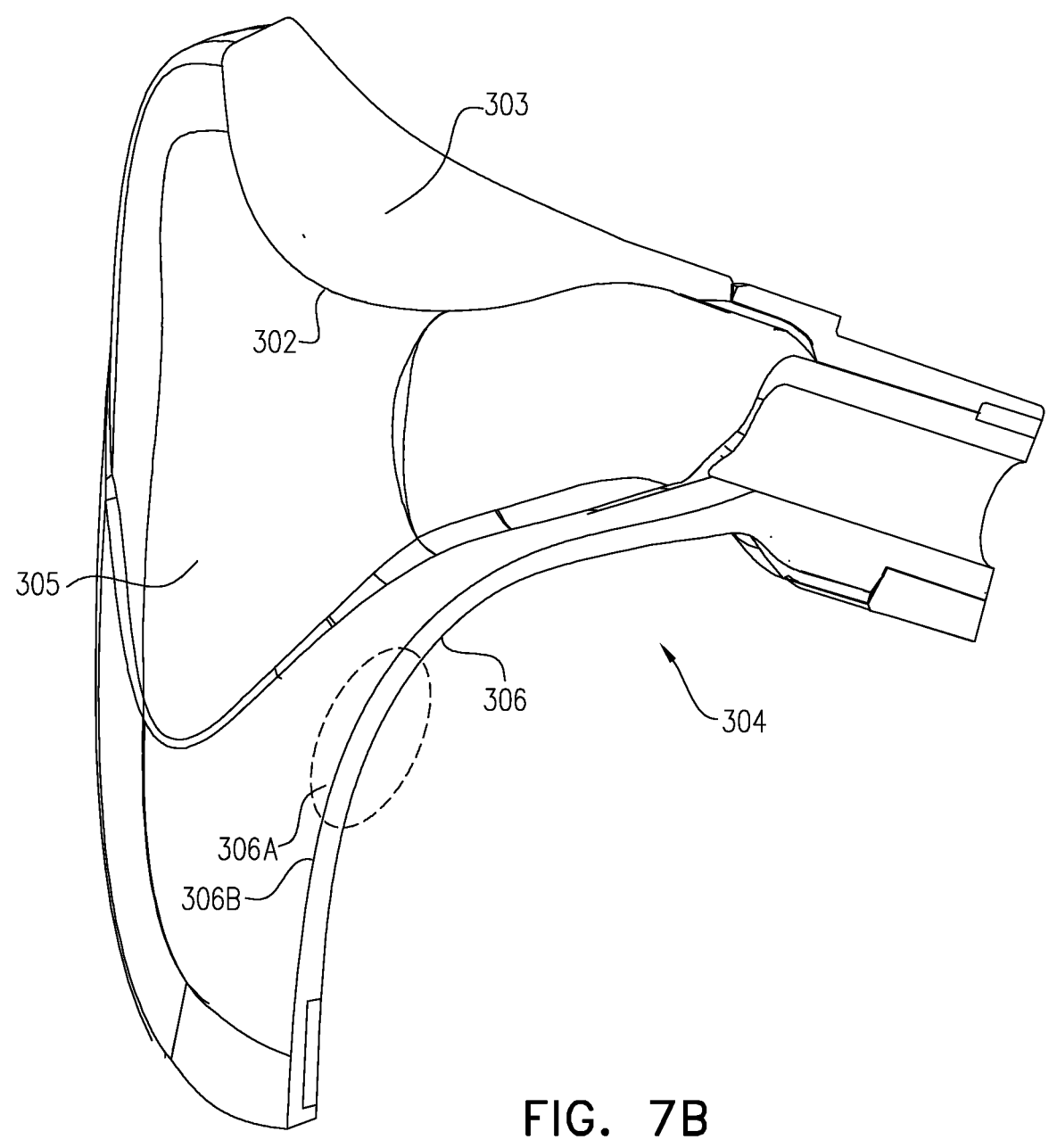
FIG. 7B illustrates a cross-section of FIG. 7A.
Figure 7C:
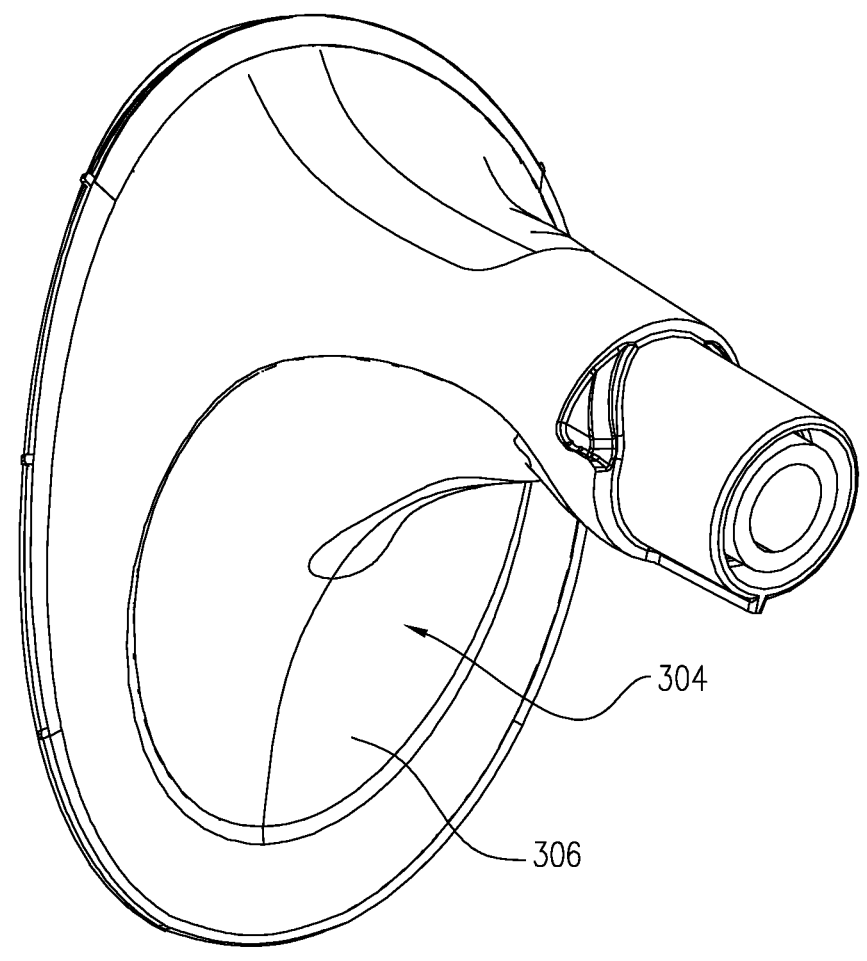
FIG. 7C illustrates a rear perspective view of the funnel illustrated in FIG. 7A.

Attention is now directed towards FIGS. 7A-7C illustrating a funnel 300 according to certain aspects of the presently disclosed subject matter. The funnel 300 can be used in any of the milk extraction assemblies described herein with respect to various aspects of the presently disclosed subject matter. For instance, the funnel 300 can replace the funnel 131 in the breast milk pump 10 described herein according to various aspects.

The funnel 300 is configured to be used with the breast milk pump 10 or any other breast milk pump generally known to be usable to extract milk from the breast of a user. The funnel 300 comprises a rigid portion 301 having an internal surface 302 facing an interior of the funnel 300 and an opposite external surface 303. The rigid portion 301 includes at least one opening 304 formed therewithin.

The funnel 300 comprises a flexible layer 305 over-molded over the internal surface 302 of the rigid portion 301. In some examples, the flexible layer 305 can be over-molded over the external surface 303 of the rigid member 301. The flexible layer 305 comprises a manipulable portion 306 extending over the at least one opening 304 and configured to be manipulated by a stimulating mechanism (for example, the stimulating mechanism 100). The flexible layer 305 is over-molded over a majority of the internal surface 302 of the rigid portion 301.

The flexible layer 305 is configured to be manipulated by the stimulating mechanism and hence requires to be strongly connected to the rigid portion 301. The over-molding of the flexible layer 305 imparts more strength to the connection of the flexible layer 305 and the rigid portion 301 than a connection on the edges only. The surface area of the connection of the flexible layer 305 and the rigid portion 301 increases substantially thereby providing enhanced strength to the funnel, especially to the flexible layer 305.

The manipulable portion 306 is configured to be manipulated via the at least one opening 304. The opening 304 is positioned in the rigid portion 301 so as to be located towards a lower part of the breast of the user when the breast milk pump is in use. The manipulable portion 306 is configured to engage at least a part of the breast at least when manipulated. The part of the breast can be nipple or areola.

The flexible layer 305 further comprises a remaining flexible portion 307 at least partially surrounding the manipulable portion 306. The manipulable portion 306 is more flexible than at least a part of the remaining flexible portion 307. A thickness of at least a part of the manipulable portion 306 is lesser than that of at least a part of remaining flexible portion 307. The manipulable portion 306 comprises a thinnest portion 306A and a remaining manipulable portion 306B surrounding the thinnest portion 306A, and a thickness of the manipulable portion 306 increases from the thinnest portion 306A towards the remaining manipulable portion 306B.

The rigid portion 301 is formed of a first material having first level of rigidity and the flexible layer 305 is formed of a second material having a second level of rigidity lesser than the first level of rigidity. In some examples, the rigid portion 301 can be made up of material comprising plastic and the flexible layer 305 can be made up of a material comprising silicon.

Figure 8A:
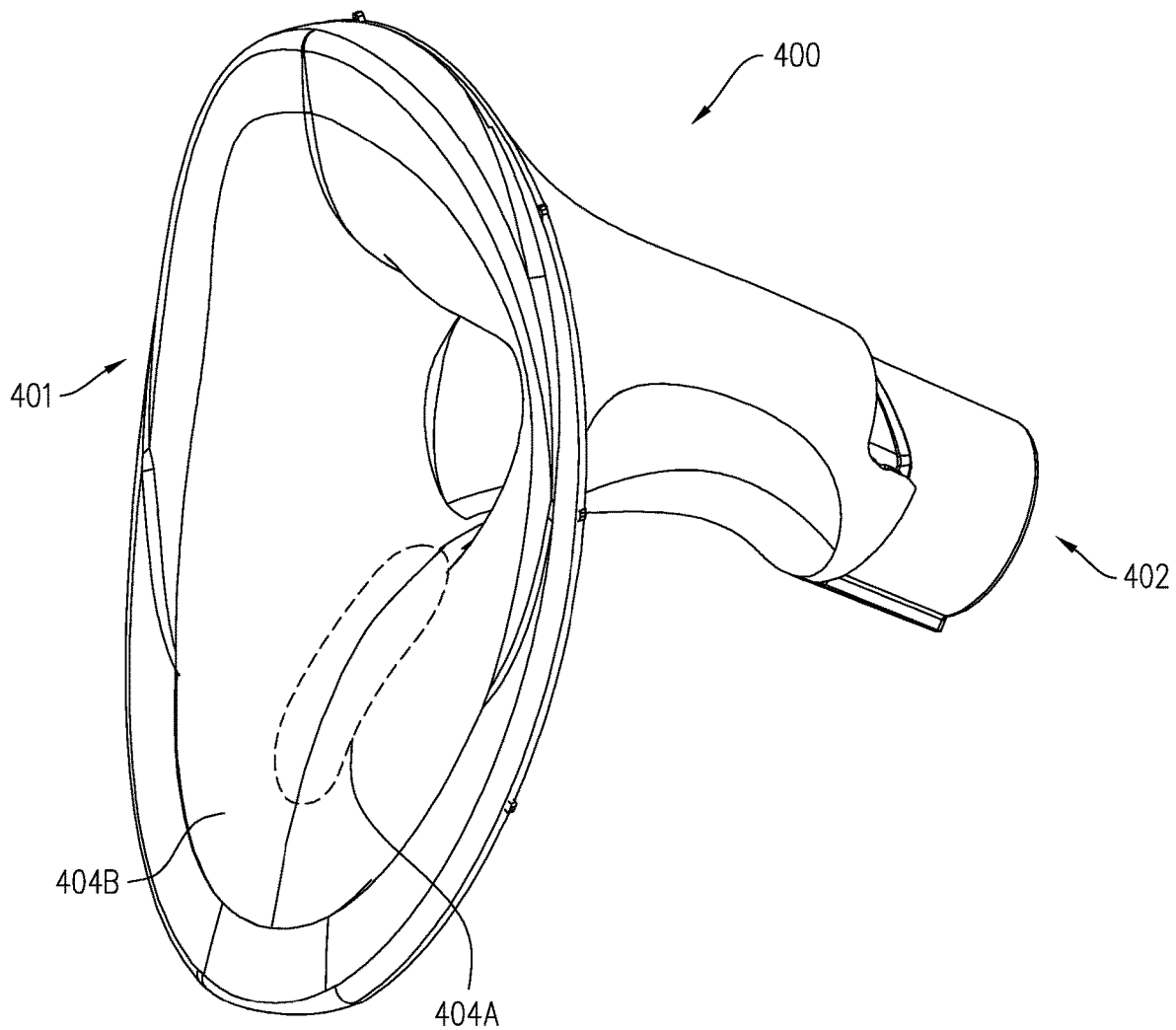
FIG. 8A illustrates a side perspective view of a funnel according to certain aspects of the presently disclosed subject matter.
Figure 8B:
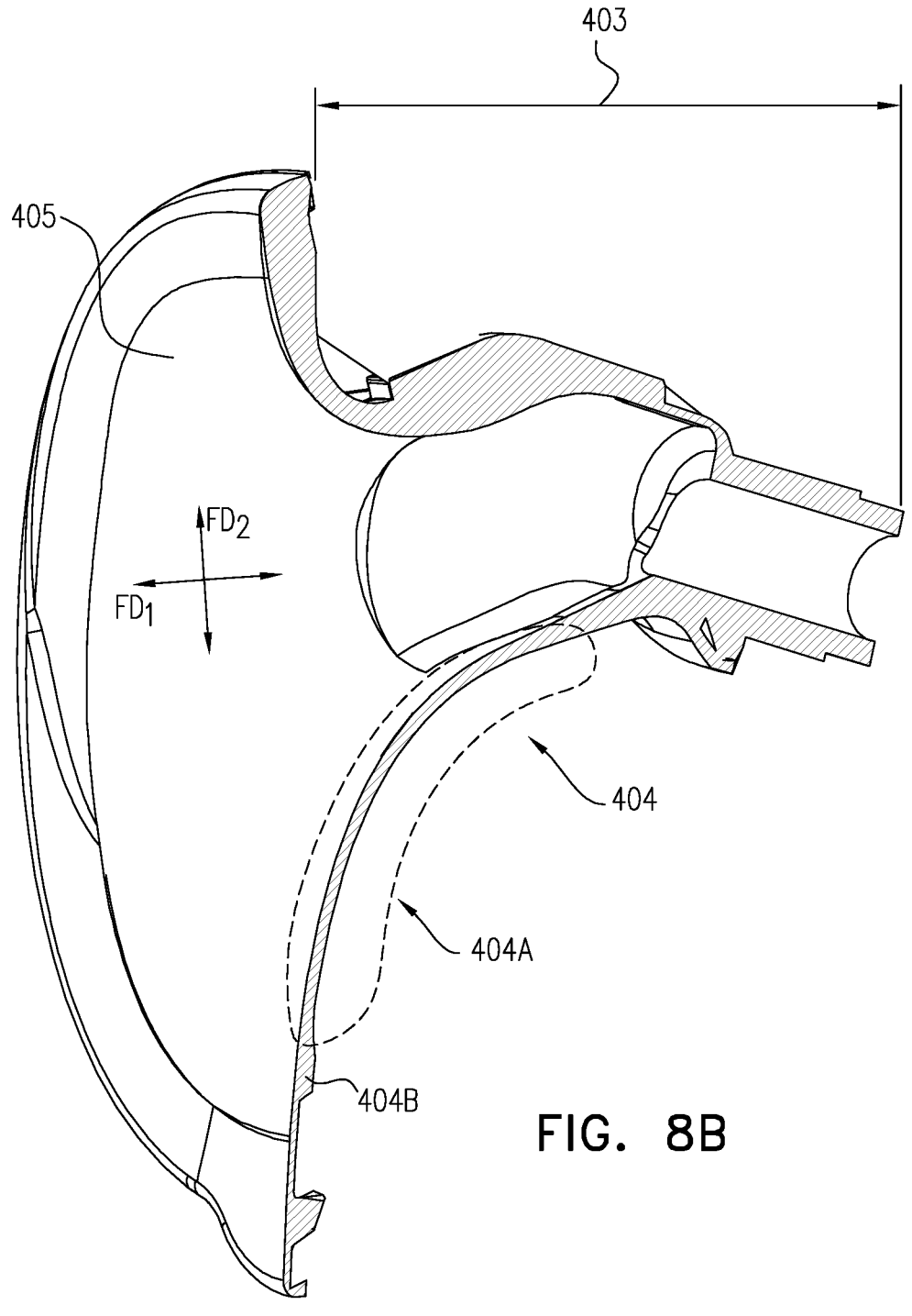
FIG. 8B illustrates a cross-section of FIG. 8A.

Attention is now directed towards FIGS. 8A-8B illustrating a funnel 400 according to certain aspects of the presently disclosed subject matter. The funnel 400 can be used in any of the milk extraction assemblies described herein with respect to various aspects of the presently disclosed subject matter. For instance, the funnel 400 can replace the funnel 131 in the breast milk assembly 10 described herein according to various aspects. The funnel 400 can be made up of a single material, which can be silicon.

The funnel 400 is configured to be used with the breast milk pump 10 or any other breast milk pump generally known to be usable to extract milk from the breast of a user. The funnel 400 comprises a funnel first open end 401 configured to engage a breast of a user and a funnel second open end 402 opposite to the funnel first open end 401. The funnel 400 comprises a funnel intermediate portion 403 extending between the funnel first open end 401 and the funnel second open end 402.

The funnel intermediate portion 403 comprises a manipulable portion 404 configured to deform upon being manipulated by a stimulating mechanism (for example, the stimulating mechanism 100) of a breast milk pump. The funnel intermediate portion 403 comprises a remaining portion 405 at least partially surrounding the manipulable portion 404 and configured to retain its shape upon operation of the stimulating mechanism, the manipulable portion 404 having a thinnest portion 404A and a remaining manipulable portion 404B, and a thickness of the manipulable portion 404 increases from the thinnest portion 404A towards at least a part of the remaining manipulable portion 404B.

The thickness of the manipulable portion 404 increases from the thinnest portion 404A towards at least one of: (i) a first direction FD1 extending between the funnel first open end 401 and the funnel second open end 402, (ii) a second direction FD2 perpendicular to the first direction, and (iii) a third direction being a combination of the first FD1 and the second direction FD2.

The manipulable portion 404 is flexible. The thinnest portion 404A is more flexible than the remaining manipulable portion 404B. The first open end 401 is configured to retain its shape upon operation of the stimulating mechanism. The second open end 402 is configured to retain its shape upon operation of the stimulating mechanism. The funnel 400 can made up of a material comprising silicon.

The invention claimed is:

1. A pumping device configured to be used in conjunction with a breast milk pump, said breast milk pump including at least one electrically operable component and a vacuum assembly, the pumping device being connectable to the breast milk pump via a cable including a cable first end connectable to the breast milk pump, an opposite cable second end connectable to the pumping device, and an electrical wiring and an air flow conduit extending between the cable first end and the opposite cable second end, the pumping device comprising:

an air pump configured to create a vacuum in the vacuum assembly via the air flow conduit;

a pumping device hybrid connection port configured to be connected to the opposite cable second end, the pumping device hybrid connection port comprising a pumping device electrical connection sub-port configured to provide an electrical interface between the electrical wiring and the pumping device, and a pumping device air flow connection sub-port configured to establish an air flow interface between the air flow conduit and the air pump, the pumping device being configured to provide an electrical power to the at least one electrically operable component via the electrical wiring; and wherein the pumping device hybrid connection port comprises a common recess formed in the pumping device, and wherein the pumping device electrical connection sub-port and the pumping device air flow connection sub-port are integrally formed within the common recess.

2. The pumping device of claim 1, wherein the pumping device comprises an electrical power source.

3. The pumping device of claim 1, wherein the pumping device is connectable to an external electrical power source and is configured to relay the electrical power to the electrical wiring.

4. The pumping device of claim 1, wherein the pumping device comprises a controller configured to control the air pump and/or a flow of the electrical power to the electrical wiring.

5. The pumping device of claim 1, wherein the pumping device comprises an input interface configured to receive commands related to operation of the pumping device.

6. The pumping device of claim 1, wherein the pumping device comprises a display interface configured to display a data related to operation of the pumping device.

7. A breast milk extraction kit, comprising:

a pumping device;

a breast milk pump including at least one electrically operable component and a vacuum assembly;

a cable comprising a cable first end connectable to the breast milk pump, an opposite cable second end connectable to the pumping device, and an electrical wiring and an air flow conduit extending between the cable first end and the opposite cable second end;

the pumping device comprising an air pump and a pumping device hybrid connection port, the pumping device hybrid connection port configured to be connected to the opposite cable second end, the pumping device hybrid connection port comprising a pumping device electrical connection sub-port configured to provide an electrical interface between the electrical wiring and the pumping device, and a pumping device air flow connection sub-port configured to establish an air flow interface between the air flow conduit and the air pump, the pumping device being configured to provide an electrical power to the at least one electrically operable component via the electrical wiring; and wherein the pumping device hybrid connection port comprises a common recess formed in the pumping device, and wherein the pumping device electrical connection sub-port and the pumping device air flow connection sub-port are integrally formed within the common recess.

8. The breast milk extraction kit of claim 7, wherein the cable comprises a first hybrid connector constituting the cable first end, said first hybrid connector comprising a first sub connector constituting a first end of the electrical wiring and a second sub connector constituting a first end of the air conduit.

9. The breast milk extraction kit of claim 7, wherein the cable comprises a second hybrid connector constituting the opposite cable second end, said second hybrid connector comprising a first sub connector constituting a second end of the electrical wiring and a second sub connector constituting a second end of the air conduit.

* * * * *